US010717755B2

(12) United States Patent
Jiang et al.

(10) Patent No.: US 10,717,755 B2
(45) Date of Patent: Jul. 21, 2020

(54) CO-CRYSTAL FORMS OF A NOVOBIOCIN ANALOG AND PROLINE

(71) Applicant: Reata Pharmaceuticals, Inc., Irving, TX (US)

(72) Inventors: Xin Jiang, Coppell, TX (US); John Allen Walling, Cisco, TX (US); Melanie J. Bevill, West Lafayette, IN (US); Christopher S. Seadeek, West Lafayette, IN (US); Jared P. Smit, Lafayette, IN (US)

(73) Assignee: Reata Pharmaceuticals, Inc., Irving, TX (US)

( * ) Notice: Subject to any disclaimer, the term of this patent is extended or adjusted under 35 U.S.C. 154(b) by 0 days.

(21) Appl. No.: 16/265,256

(22) Filed: Feb. 1, 2019

(65) Prior Publication Data

US 2019/0241599 A1 Aug. 8, 2019

Related U.S. Application Data

(60) Provisional application No. 62/627,570, filed on Feb. 7, 2018.

(51) Int. Cl.
| | | |
|---|---|---|
| *A01N 43/04* | (2006.01) | |
| *A61K 31/70* | (2006.01) | |
| *C07H 15/207* | (2006.01) | |
| *A61P 3/10* | (2006.01) | |
| *C07H 1/06* | (2006.01) | |
| *A61P 25/02* | (2006.01) | |
| *A61K 31/7048* | (2006.01) | |

(52) U.S. Cl.
CPC ....... *C07H 15/207* (2013.01); *A61K 31/7048* (2013.01); *A61P 3/10* (2018.01); *A61P 25/02* (2018.01); *C07H 1/06* (2013.01); *C07B 2200/13* (2013.01)

(58) Field of Classification Search
None
See application file for complete search history.

(56) References Cited

U.S. PATENT DOCUMENTS 9,422,320 B2   8/2016   Blagg et al.

FOREIGN PATENT DOCUMENTS

| TW | 201945381 | 12/2019 |
| WO | WO-2015/200514 A2 | 12/2015 |
| WO | 2019156907 | 8/2019 |

OTHER PUBLICATIONS

Brittain, H. G. (2003). X-ray diffraction of pharmaceutical materials. Profiles of Drug Substances, Excipients and Related Methodology, 30, 271-319.*
"International Application Serial No. PCT/US2019/016304, International Search Report dated Apr. 24, 2019", 7 pgs.
"International Application Serial No. PCT/US2019/016304, Written Opinion dated Apr. 24, 2019", 8 pgs.
Bhaskar, Reddy Kusuma, et al., "Synthesis and Evaluation of Novologues as C-Terminal Hsp90 Inhibitors with Cytoprotective Activity against Sensory Neuron Glucotoxicity", Journal of Medicinal Chemistry, vol. 55, No. 12, (Jun. 28, 2012), 5797-5812.
Claira, "Crystalline Polymorphism of Organic Compounds", Topics in Chemistry, vol. 198, (Jan. 1, 1998), 163-208.
Geraldine, Springuel, et al., "Innovative Chiral Resolution Using Enantiospecific Co-Crystallization in Solution", Crystal Growth & Design., vol. 12, No. 7, (Jun. 18, 2012), 3374-3378.
Hancock, Bruno, et al., "Characteristics and Significance of Amorphous State in Pharmaceutical Systems", J. Pharm Sci, 86(1), (Jan. 1997), 1-12.
Hancock, Bruno, et al., "What is the true solubility advantage for amorphous pharmaceuticals?", Pharmac. Res. 17(4), (2000), 397-404.
Liu, Mingyu, et al., "Development of a pharmaceutical cocrystal with solution crystallization technology: Preparation, characterization, and evaluation of myricetin-proline cocrystals", European Journal of Pharmaceutics and Biopharmaceutics, Elsevier Science Publishers B.V., Amsterdam, NL, vol. 107, (Jul. 6, 2016), 151-159.
Ma, Jiacheng, et al., "Modulating Molecular Chaperones Improves Mitochondrial Bioenergetics and Decreases the Inflammatory Transcriptome in Diabetic Sensory Neurons, pp. 1637-1648", ACS Chem Neurosci, 6(9), (Sep. 16, 2015), 27 pgs.
P, Vishweshwar, et al., "Pharmaceutical co-crystals", Journal of Pharmaceutical Sciences, American Pharmaceutical Association, US, vol. 95, No. 3, (Mar. 1, 2006), 499-516.
Roy, L, et al., "Chapter 11. Co-crystal Solubility and Thermodynamic Stability", In: Pharmaceutical salts and co-crystals, (Jan. 1, 2011), 247-279.
Shan, N, et al,. "The role of cocrystals in pharmaceutical science", Drug Discovery Today, Elsevier, Amsterdam, NL, vol. 13, No. 9-10, (May 1, 2008), 440-446.

* cited by examiner

*Primary Examiner* — Patrick T Lewis
(74) *Attorney, Agent, or Firm* — Schwegman Lundberg & Woessner, P.A.

(57) ABSTRACT

Disclosed are co-crystal forms of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline or D-proline, their pharmaceutical compositions, processes of manufacture, and methods of use for treating neurodegenerative disorders such as diabetic peripheral neuropathy.

43 Claims, 25 Drawing Sheets

CO-CRYSTAL FORMS OF A NOVOBIOCIN ANALOG AND PROLINE

CLAIM OF PRIORITY

This patent application claims the benefit of priority to U.S. Application Ser. No. 62/627,570, filed Feb. 7, 2018, which is incorporated by reference herein in its entirety.

BACKGROUND

Approximately 26 million Americans are afflicted with either Type 1 or Type 2 diabetes. Despite the use of insulin and oral anti-diabetic medications to help maintain euglycemia, about 60-70% of these individuals develop diabetic peripheral neuropathy (DPN). See Veves, A.; Backonja, M.; Malik, R. A., *Pain Med.* 9 (2008) 660-674. A number of small molecules based upon the novobiocin scaffold are reported to inhibit heat shock protein 90 (Hsp90), and are reported to have significant neuroprotective properties and to be useful for reversing symptoms of DPN in animal models. See B. R. Kusuma et at., *J. Med. Chem.* 55 (2012) 5797-5812; U.S. Pat. No. 9,422,320.

One novobiocin analog ("novologue") of this type is N-(2-(5-(((3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4) which is reported to exhibit high neuronal protective activity. Kusuma (2012). Novologue 4 is further reported to have effects that are dependent upon the presence of another heat shock protein, Hsp70, while other effects are independent of Hsp70. The precise role of Hsp70 in the mechanism of action of novologue 4 and related compounds has not been fully characterized. J. Ma et at., *ACS Chem. Neurosci.* 6(9) (2015) 1637-1648.

The synthesis of novologue 4 is reported to follow a procedure that results in an amorphous solid, and its physico-chemical characterization omits definitive assignment of stereochemistry at the 2-position (Kusuma (2012); U.S. Pat. No. 9,422,320), thereby allowing in principle for the existence of two possible anomers 4a and 4b as shown below:

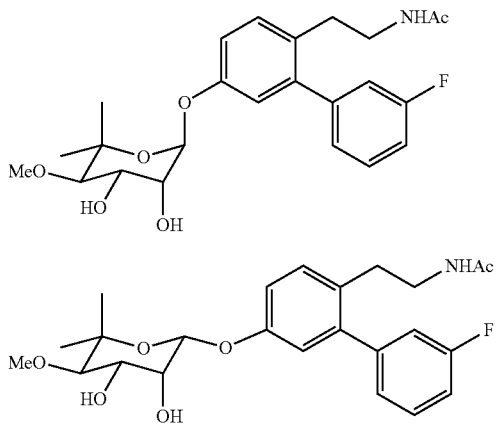

The published synthesis of 4 (also known as KU-596), while indicating an HPLC purity of 95.6%, does not indicate anomeric purity of the amorphous solid, as evidenced by the fact that only the noviose 2-position lacks definitive assignment of stereochemistry. (Kusuma (2012).

SUMMARY

The present disclosure is premised upon the surprising discovery that co-crystal forms of novologue 4a and L-proline or D-proline are realized in high yield, purity, and anomeric purity. The inventive forms moreover demonstrate significant improvements in bioavailability, relative to the known amorphous form 4.

Thus, one embodiment of the disclosure is a co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline (1:2). The co-crystal is characterized by an X-ray powder diffractogram comprising the following peaks: 14.76, 16.86, 19.00, and 21.05 °2θ±0.20 °2θ as determined on a diffractometer using Cu-Kα radiation at a wavelength of 1.54178 Å. This co-crystal is referred to herein as "Form B."

Another embodiment is a co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline (1:2). The co-crystal is characterized by an X-ray powder diffractogram comprising the following peaks: 9.20, 16.19, 18.45, and 24.51 °2θ±0.2 °2θ as determined on a diffractometer using Cu-Kα radiation at a wavelength of 1.54178 Å. This co-crystal is referred to herein as "Form D."

Additionally, an embodiment is a co-crystal of N-(2-(5-(((2R,3R,4S,5R)-3,4-dihydroxy-5-methoxy-6,6-dimethyl-tetra-hydro-2H-pyran-2-yl)oxy)-3'-fluoro-[1,1'-biphenyl]-2-yl)ethyl)-acetamide and L-proline that is present as an acetone solvate (1:1:1). This co-crystal is characterized by an X-ray powder diffractogram comprising the following peaks: 14.64, 17.53, 18.91, and 21.33 °2θ±0.20 °2θ as determined on a diffractometer using Cu-Kα radiation at a wavelength of 1.54178 Å. This co-crystal is referred to herein as "Form C."

In a further embodiment, the present disclosure is drawn to a co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline as a solvate of methyl ethyl ketone and pyrazine in a molar ratio of about 1:1.2:0.6:0.1, respectively. The co-crystal is characterized by an X-ray powder diffractogram comprising the following peaks: 10.42, 14.62, 19.28, and 21.14 °2θ±0.20 °2θ as determined on a diffractometer using Cu-Kα radiation at a wavelength of 1.54178 Å. This co-crystal is referred to herein as "Form G."

The disclosure also provides a co-crystal of N-(2-(5-(((2R,3R,4S,5R)-3,4-dihydroxy-5-methoxy-6,6-dimethyl-tetra-hydro-2H-pyran-2-yl)oxy)-3'-fluoro-[1,1'-biphenyl]-2-yl)ethyl)-acetamide and D-proline (1:1), characterized by an X-ray powder diffractogram comprising the following peaks: 11.77, 14.52, 19.54, and 21.23 °2θ±0.20 °2θ as determined on a diffractometer using Cu-$K_{\alpha 1}$ radiation at a wavelength of 1.5405929 Å.

The disclosure further provides a co-crystal of N-(2-(5-(((2R,3R,4S,5R)-3,4-dihydroxy-5-methoxy-6,6-dimethyl-tetra-hydro-2H-pyran-2-yl)oxy)-3'-fluoro-[1,1'-biphenyl]-2-yl)ethyl)-acetamide and L-proline (1:1), characterized by an X-ray powder diffractogram comprising the following peaks: 8.52, 16.33, 19.50, and 21.22 °2θ±0.20 °2θ as determined on a diffractometer using Cu-$K_{\alpha 1}$ radiation at a wavelength of 1.5405929 Å.

In accordance with another embodiment, the disclosure is drawn to a pharmaceutical composition that comprises any one of the co-crystal forms described herein. The composition further comprises a pharmaceutically acceptable solid carrier. In some embodiments, the composition further comprises one or more additional co-crystal forms.

Another embodiment of the disclosure is a method for inhibiting heat shock protein 90 (Hsp90) in a subject. The method comprises administering to the subject a therapeutically effective amount of a co-crystal described herein.

The disclosure also is embodied in a method for treating or preventing a neurodegenerative disorder in a subject suffering therefrom. The method comprises administering to the subject a therapeutically effective amount of a co-crystal described herein. In some embodiments, the neurodegenerative disorder is diabetic peripheral neuropathy (DPN).

Alternatively, according to other embodiments, the disclosure provides a method for preventing or reducing the likelihood of diabetic peripheral neuropathy from developing in a subject who suffers from Type 1 or Type 2 diabetes. The method comprises administering to the subject a therapeutically effective amount of a co-crystal described herein.

In accordance with another embodiment, the disclosure provides a process for making the Form B co-crystal. The process comprises the step of heating to a first temperature a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in about a 1:1 to about a 1:2 molar ratio in a $C_{1-6}$-alkyl alcohol to yield a solution. The solution is then cooled to a second temperature no higher than about 30° C. to thereby yield a slurry of the co-crystal, and the slurry is then stirred at the second temperature for a duration of about 72 hours or less.

Another embodiment is a process of making the Form D co-crystal. The process comprises heating to a first temperature a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in about a 1:1 molar ratio in EtOH or acetonitrile, then cooling the solution to a second temperature no higher than about 30° C. to thereby yield a suspension of the co-crystal. The suspension is then stirred at the second temperature for a duration of about 72 hours or less.

The disclosure is embodied in yet another process drawn to making the Form C co-crystal. The process comprises (a) optionally refluxing equimolar amounts of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in EtOH to yield a solution, and cooling the solution to a temperature no higher than about 30° C. to thereby yield a solid product. The product of step (a), or otherwise a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in about a 1:1 molar ratio, is then stirred in acetone at a temperature no higher than about 30° C. for a duration of about 72 hours or less to thereby yield the co-crystal.

In accordance with another embodiment, the disclosure provides a process for making the Form G co-crystal. The process comprises combining N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a), L-proline, and pyrazine in molar ratios of about 1:1:20, respectively, in a mixed solvent of methyl ethyl ketone (MEK) and MeOH to yield a solution, and then stirring the solution to thereby yield the co-crystal.

The disclosure additionally provides a process for making the co-crystal of 4a/D-proline as described herein, comprising heating to a first temperature a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and D-proline in about a 1:1 molar ratio in a $C_{1-6}$-alkyl alcohol to yield a solution; and cooling the solution to a second temperature no higher than about 30° C. to thereby yield a suspension of the co-crystal.

In an additional embodiment, the disclosure provides a method of increasing the concentration of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) relative to N-(2-(5-(((2S,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4b) in a composition comprising 4a and 4b. The method comprises contacting the composition with proline in a solvent, and subjecting the composition, proline, and solvent to crystallization conditions, whereby a co-crystal of 4a and proline is produced. The bulk co-crystal exhibits a concentration of 4a that is higher than in the composition comprising 4a and 4b.

DETAILED DESCRIPTION

Definitions

Figure 1:
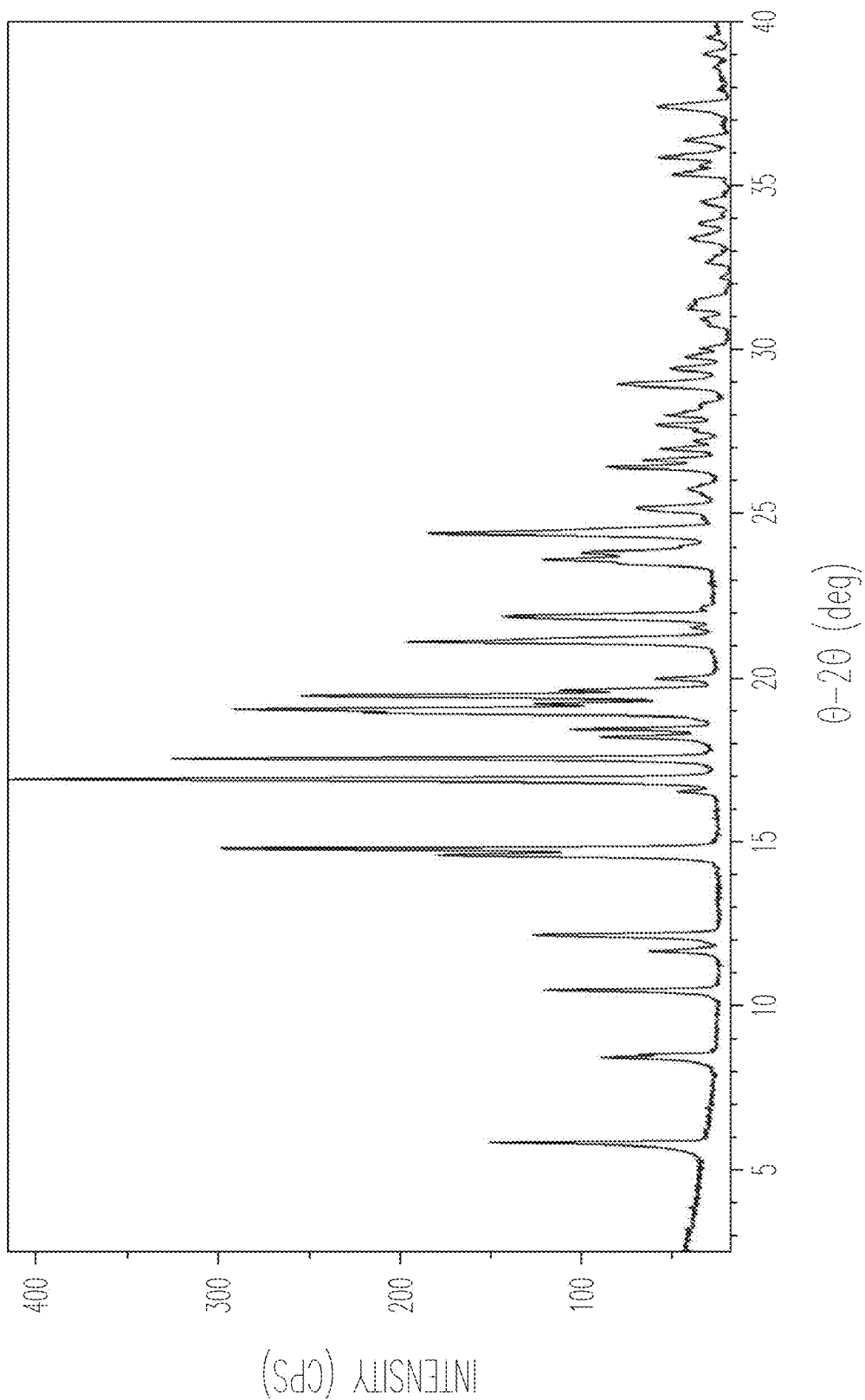
FIG. 1 presents an X-ray powder diffraction (XRPD) pattern of Form B.

Abbreviations, acronyms, and terms as used throughout the disclosure have the following meanings.

| | |
|---|---|
| NMR | Nuclear magnetic resonance spectroscopy |
| OM | Optical microscopy |
| XRPD | X-ray powder diffraction |
| CP | Crash precipitation |
| FE | Fast evaporation |
| RC | Reaction crystallization |
| SC | Slow cooling |
| SE | Slow evaporation |
| amt | Amount |
| API | Active pharmaceutical ingredient |
| B/E | Birefringence and extinction |
| eq | Equivalent |
| min. | Minute(s) |
| mol. | Molar |
| Obs | Observation |
| ppt | Precipitate or precipitation |
| ref. | Refrigerator |
| RT | Room temperature |
| Soln/soln | Solution |
| vac | Vacuum |
| ACN | Acetonitrile |
| 2-BuOH | 2-Butanol |
| EtOH | Ethanol |
| EtOAc | Ethyl acetate |
| IPA or 2-PrOH | Isopropyl alcohol, 2-propanol |
| IPE | Isopropyl ether |
| MEK | Methyl ethyl ketone |
| MeOH | Methanol |
| MTBE or TBME | Methyl-tertiary-butyl ether |
| THF | Tetrahydrofuran |
| TMP | 2,3,5,6-Tetramethyl-pyrazine |
| w/w | weight/weight. The weight percentage of 4a in a 4a/proline co-crystal is calculated by excluding the proline content, i.e. w/w = (weight 4a)/(weight of all non-proline species in the co-crystal). |

Introduction

As summarized above, studies of novologue 4 highlighted excellent potency of the compound in the Hsp70-independent inhibition of Hsp90 (Kusuma (2012) and Ma (2015)). The studies revealed potential drawbacks to the synthesis of the compound, including its tendency to result in a mixture of α-anomer 4a and β-anomer 4b and a low overall yield. Additionally, while the reported column chromatography purification method of 4 is appropriate for small scale study, and even then the compound was about 95% pure (HPLC), the method is impractical for generating large and pharmaceutically pure quantities of α-anomer 4a for drug development.

The present inventors therefore undertook various crystallization strategies to isolate 4a. However, the inventors discovered no conditions under which 4a could be separated from 4b by crystallization.

The inventors subjected amorphous 4a to a co-crystal screen comprised of 28 co-formers, and surprisingly discovered that L-proline and D-proline selectively co-crystallized with α-anomer 4a. The inventors moreover discovered that L-proline and D-proline are the only tested co-formers that yielded any crystalline material amenable to definitive characterization (see Example 3).

Co-Crystal Forms

Contacting compound 4 with the co-former L-proline or D-proline surprisingly results in the selective co-crystallization of 4a with either co-former (see Examples 2 and 10). In this manner, co-crystallization achieves quantities of 4 that are highly enriched in 4a, relative to 4b, as determined by HPLC, for example. Thus, in an embodiment, selective co-crystallization of 4a with L-proline reduces the concentration of the β-anomer and it facilitates removal of minor impurities. Consequently, formation of the 4a/L-proline co-crystal improves the purity of 4a (HPLC) from about 90% to at least 95%, 96%, 97% or 98%. Subsequent recrystallization of 4a/L-proline co-crystal further improves purity of 4a to at least 97%, 98%, or 99%.

Similarly, in other embodiments, co-crystallization of a starting composition of 4a and 4b with D-proline, such as in about equimolar amounts of 4a/4b and D-proline, results in a 4a/D-proline co-crystal wherein the purity (i.e., concentration) of 4a, relative to the concentration of 4a in the starting composition, improves by at least 15%, 10%, 5%, or 3% as determined by HPLC. Thus, for example, a starting composition of 4a/4b contains 4a in a concentration of about 93%, and following co-crystallization with D-proline the resulting co-crystal contains 4a in concentration of about 98%. In some embodiments, a 4a/D-proline co-crystal contains 4a in a final purity of at least 85%, 90%, 95%, 97%, 98%, or 99%.

In other embodiments, a quantity of the α-anomer 4a is purified by contacting it with D-proline, such as in equimolar amounts, whereby 4a/D-proline co-crystal is produced. The resultant concentration of the 4a in the bulk co-crystal is higher, for instance by at least 1%, 2%, 3%, 4%, or 5% (HPLC) than the concentration of 4a in the starting quantity of 4a. Each of these embodiments contemplates the optional step of one or more re-crystallizations to even further increase the purity of 4a in a given co-crystal.

The co-crystallization also produced a variety of co-crystal forms as summarized hereinabove. The various forms are identified and distinguished from one another by one or more analytical techniques including X-ray powder diffraction (XRPD), differential scanning calorimetry (DSC), and thermogravimetric analysis (TGA).

Form B

Thus, one embodiment denoted Form B is a co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in a 1:2 molar ratio, respectively. The X-ray powder diffractogram comprises characterizing peaks at 14.76, 16.86, 19.00, and 21.05 °2θ±0.2 °2θ as determined on a diffractometer using Cu-Kα radiation at a wavelength of 1.54178 Å. In an embodiment, the X-ray powder diffractogram further comprises peaks at 12.14, 17.51, 18.89, and 19.41 °2θ±0.2 °2θ. In accordance with yet another embodiment, Form B is additionally characterized substantially by its entire X-ray powder diffractogram (see FIG. 1).

The DSC curve of Form B is characteristic of this co-crystal in that it exhibits an exotherm at about 211° C. According to one embodiment, Form B is characterized by the entire DSC thermogram as substantially shown in FIG. 2.

The disclosure is further embodied in a process for making Form B (see Example 4). The process comprises heating a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in about a 1:1 to about a 1:2 molar ratio in a $C_{1-6}$-alkyl alcohol to yield a solution. In some embodiments, 4a is present as pure 4a, while in other embodiments 4a is present in combination with the β-anomer 4b, such as the combination resulting from the published synthesis of 4 (Kusuma 2012, supra). For instance, 4a is present in 95%, 96%, 97%, 98%, or 99% (w/w). The combination is heated to a first temperature ranging from about 50° C. to about 80° C. Illustrative $C_{1-6}$-alkyl alcohols include methanol, ethanol, and n- and i-propanol. In one embodiment, the alcohol is ethanol. In accordance with an embodiment, a convenient first temperature is the boiling point of the alcohol under standard pressure. Thus, for instance, when ethanol is the alcohol, the first temperature is the boiling point, i.e., about 78° C.

The process further comprises the step of cooling the solution of 4a and L-proline to a second temperature that is no higher than about 30° C. to thereby yield a slurry of the co-crystal. The slurry is stirred at the second temperature for a duration of about 72 hours or less. In an embodiment, the slurry is filtered to isolate Form B.

Form D

The disclosure is further embodied in a co-crystal of 4a and L-proline present in a 1:2 molar ratio, respectively, and it is denoted as Form D. Form D is characterized by an X-ray powder diffractogram comprising the following peaks: 9.20, 16.19, 18.45, and 24.51 °2θ±0.2 °2θ as determined on a diffractometer using Cu-Kα radiation at a wavelength of 1.54178 Å. A further embodiment is drawn to additional characterizing peaks occurring at 11.83, 17.16, 20.15, and 25.34 °2θ±0.2 °2°. Form D is additionally characterized by its X-ray powder diffractogram as substantially shown in FIG. 14.

The DSC curve of Form D also is characteristic of this co-crystal in that it exhibits an endotherm at about 212.2° C., with an onset temperature of about 211.2° C. According to an embodiment, Form D is characterized by the entire DSC thermogram as substantially shown in FIG. 15.

An embodiment of the disclosure also relates to a process for making Form D. The process comprises the step of heating to a first temperature a combination of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in about a 1:1 molar ratio in EtOH or acetonitrile. In some embodiments, 4a is present as pure 4a, while in other embodiments 4a is present in combination with the β-anomer 4b, such as the combination resulting from the published synthesis of 4 (Kusuma 2012, supra). For instance, 4a is present in 95%, 96%, 97%, 98%, or 99% (w/w). The first temperature is one selected in the range of about 70° C. to about 85° C. A convenient temperature, for example, is achieved by refluxing the combination, i.e., at the boiling point of acetonitrile of about 82° C.

The process further comprises the steps of cooling the solution to a second temperature no higher than about 30° C. to thereby yield a suspension of the co-crystal, and then stirring the suspension at the second temperature for a duration of about 72 hours or less. According to an embodiment, the suspension is filtered, for example, to isolate Form D.

Form C

The disclosure is further embodied in an acetone solvate of a co-crystal of 4a and L-proline present in 1:1:1 molar ratios, respectively, and it is denoted as Form C (see Example 6). The co-crystal is characterized by an X-ray powder diffractogram comprising the following peaks: 14.64, 17.53, 18.91, and 21.33 °2θ±0.2 °2θ as determined on a diffractometer using Cu-Kα radiation at a wavelength of 1.54178 Å. More specifically, in accordance with another embodiment, the X-ray powder diffractogram comprises additional peaks at 12.10, 15.14, 18.26, and 19.56 °2θ±0.2 °2θ. These and additional peaks that are characteristic of Form C are exhibited in its X-ray powder diffractogram as substantially shown in FIG. 10.

Form C is additionally characterized by reference to its TGA thermogram that comprises weight loss steps concluding at about 150° C. and about 220° C. An embodiment is drawn to the TGA thermogram of Form C, as substantially shown in FIG. 11.

Form C is made by a process in accordance with various embodiments of the disclosure. Thus, in one embodiment, the process comprises refluxing equimolar amounts of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a) and L-proline in EtOH to yield a solution, and then cooling the solution to a temperature no higher than about 30° C. to thereby yield a solid product. The solid product is then stirred in acetone at a temperature no higher than about 30° C. for a duration of about 72 hours or less to thereby yield Form C.

Alternatively, a combination of 4a and L-proline in about a 1:1 molar ratio is stirred in acetone at a temperature no higher than about 30° C. for a duration of about 72 hours or less to thereby yield Form C. In either of these embodiments, 4a is present as pure 4a or as a combination with the β-anomer 4b, such as that produced by the published synthesis of 4. In a further embodiment, Form C is isolated, such as by filtration.

Form G

The disclosure further relates to a co-crystal of 4a and L-proline that exists as a solvate of methyl ethyl ketone and pyrazine and it is denoted as Form G (see Example 9). As explained in the examples, XRPD indexing of Form G is consistent with a 4a:L-proline molar ratio of 1:1, but the indexing does not distinguish between the comparably sized MEK and pyrazine molecules, making definitive amounts of the solvents difficult to establish by this analytical technique. Proton NMR analysis of Form G, however, established molar ratios of 4a, L-proline, MEK, and pyrazine at about 1:1.2:0.6:0.1, respectively. Form G is thus characterized by its XRPD diffractogram having characterizing peaks at 10.42, 14.62, 19.28, and 21.14 °2θ±0.2 °2θ as determined on a diffractometer using Cu-Kα radiation at a wavelength of 1.54178 Å. A further embodiment provides additional peaks at 11.85, 14.93, 17.40, and 19.28 °2θ±0.2 °2θ. Form G can also be characterized by its full XRPD diffractogram as substantially shown in FIG. 17.

XRPD analysis of Form G further established unit cell parameters that characterize the co-crystal, according to another embodiment. Thus, the parameters are a=10.975 Å, b=10.310 Å, c=15.704 Å, α=90°, β=108.56°, and γ=90°.

The disclosure further relates to a process for making Form G. The process comprises combining N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4a), L-proline, and pyrazine in molar ratios of about 1:1:20, respectively, in a mixed solvent of methyl ethyl ketone (MEK) and MeOH to yield a solution. In some embodiments, 4a is present as pure 4a, while in other embodiments 4a is present in combination with the β-anomer 4b, such as the combination resulting from the published synthesis of 4 (Kusuma 2012, supra). For instance, 4a is present in 95%, 96%, 97%, 98%, or 99% (w/w). In general, the mixed solvent is embodied by an excess of MEK over MeOH. Thus, an illustrative ratio of MEK to MeOH is about 9:1 (v/v). The solution is then stirred to thereby yield Form G.

Material A

Another embodiment of the present disclosure is a co-crystal of 4a and L-proline present in a 1:1 molar ratio, respectively, and it is denoted as Material A. Material A is characterized by an X-ray powder diffractogram comprising the following peaks: 8.52, 16.33, 19.50, and 21.22 °2θ±0.20 °2θ as determined on a diffractometer using Cu-K$_{\alpha 1}$ radiation at a wavelength of 1.5405929 Å. A further embodiment is drawn to additional characterizing peaks occurring at 9.19, 13.22, 14.75, and 17.57 °2θ±0.2 °2θ. Material A is additionally characterized by its X-ray powder diffractogram as substantially shown in FIG. 23.

XRPD analysis of Material A further established unit cell parameters that characterize the co-crystal, according to another embodiment. Thus, the parameters are a=10.126 Å, b=11.021 Å, c=30.259 Å, α=90°, β=90°, and γ=90°.

The DSC curve of Material A also is characteristic of this co-crystal in that it exhibits an endotherm at about 145° C. According to an embodiment, Material A is characterized by the entire DSC thermogram as substantially shown in FIG. 24.

Material A is additionally characterized by reference to its TGA thermogram that comprises weight loss steps concluding at about 160° C. and about 230° C. An embodiment is drawn to the TGA thermogram of Material A, as substantially shown in FIG. 24.

4a/D-Proline Co-Crystal

The disclosure also provides in another embodiment a co-crystal of 4a and D-proline present in a 1:1 molar ratio (see Example 11). The co-crystal is characterized by its XRPD diffractogram having characterizing peaks at 11.77, 14.52, 19.54, and 21.23 °2θ±0.20 °2θ as determined on a diffractometer using Cu-K$_{\alpha 1}$ radiation at a wavelength of 1.5405929 Å. Additional characterizing peaks occur at 8.45, 13.18, 16.95, and 19.12 °2θ±0.2 °2θ. These and even additional peaks that are characteristic of the co-crystal are exhibited in its X-ray powder diffractogram as substantially shown in FIG. 18.

The DSC curve of the 4a/D-proline crystal also is characteristic of this co-crystal in that it exhibits an endotherm at about 130° C. According to an embodiment, the co-crystal is characterized by the entire DSC thermogram as substantially shown in FIG. 19.

The co-crystal is additionally characterized by reference to its TGA thermogram that comprises two weight loss steps concluding at about 150-160° C. and about 230° C., respectively. An embodiment is drawn to the TGA thermogram of the co-crystal, as substantially shown in FIG. 19.

The disclosure further provides a process for making the 4a/D-proline crystal. The process comprises the steps of (a) heating to a first temperature a combination of N-(2-(5-(((2R,3R,4S,5R)-3,4-dihydroxy-5-methoxy-6,6-dimethyl-tetra-hydro-2H-pyran-2-yl)oxy)-3'-fluoro-[1,1'-biphenyl]-2-yl)ethyl)-acetamide (4a) and D-proline in about a 1:1 molar ratio in a C$_{1-6}$-alkyl alcohol to yield a solution; and (b) cooling the solution to a second temperature no higher than about 30° C. to thereby yield a suspension of the co-crystal.

In some embodiments, 4a is present as pure 4a, while in other embodiments 4a is present in combination with the β-anomer 4b, such as the combination resulting from the published synthesis of 4 (Kusuma 2012, supra). For instance, 4a is present in 95%, 96%, 97%, 98%, or 99% (w/w).

Methods of Purifying

The surprising discovery that 4a selectively co-crystallizes with L- and D-proline engenders, according to an embodiment, a method for purifying 4a from bulk quantities of 4. That is to say, the co-crystallization of 4a with proline enriches the concentration of 4a relative to 4b in a resulting bulk sample of a 4a/proline co-crystal. A method to increase the concentration of 4a first contemplates a starting composition of 4a and 4b. The starting composition can be the bulk solid that results from the published synthesis of 4, or by one of a number of alternative synthetic pathways, known or reasonably contemplated by those skilled in the art of organic synthesis, that lead to 4. Additionally, the starting composition can be a bulk solid of predominantly 4a that resulted from other means of purification, such as column chromatography. The inventors surprisingly discovered in this regard that 4a defied all attempts at crystallization; in fact, under no conditions was 4a observed to exist in crystalline form. In any of these examples, the starting composition contains at least some amount of 4b, such as 0.5 to about 10% (w/w).

A molar excess of proline, such as one to about two equivalents, is combined with the starting composition in a solvent. In some embodiments, the proline is L-proline, and in other embodiments the proline is D-proline. It is possible to use mixtures of L- and D-proline. Any solvent capable of substantially dissolving proline and starting composition is suitable for this purpose. Exemplary solvents, such as any solvent described herein, include C$_1$-C$_6$-alkyl alcohols, such as methanol and ethanol. In some embodiments of the method, it is advantageous to promote dissolution by heating the starting composition, proline, and solvent mixture. A convenient temperature for this purpose is the reflux temperature of the solvent.

The combination of starting composition, proline, and solvent is then subjected to crystallization conditions to achieve co-crystallization of 4a and proline. Various crystallization techniques are useful in this context, such as any of those described herein. In exemplary embodiments, a warm solution of the starting composition and proline is allowed to cool to room temperature. External cooling measures can be implemented to cool the solution below room temperature to facilitate co-crystallization. Alternatively, or in combination, the solvent is allowed to slowly evaporate. Any of these means, alone or in combination with each other, disturb solution equilibrium toward crystallization.

The resulting bulk co-crystal of 4a and proline is thereby enriched in 4a, relative to the concentration of 4a in the starting composition. The corresponding concentration of 4b is decreased. In addition, the method purifies 4a from other impurities. A convenient method for quantifying the concentration of 4a is by HPLC, although any analytical technique capable of resolving and quantifying the components present in the mixture would be suitable for this purpose, including gas chromatography (GC) conducted on chiral stationary phases. Thus, for instance, the concentration of 4a in the bulk co-crystal is about 3 to about 20%, or about 5 to about 15% (w/w) higher than in the starting composition. Alternatively, the increase in 4a in the bulk co-crystal, relative to the concentration of 4a in the bulk starting composition, is at least about 5%, about 10%, or about 15% (w/w). Thus, for example, a starting composition of 4 contains about 93% 4a and about 6% 4b, as determined by HPLC (see Example 10(A)). Following co-crystallization with L-proline as prescribed by the inventive method, the amount of 4b in the resulting bulk co-crystal decreases to about 2.5%. In any of these embodiments, subsequent recrystallization of the 4a/proline co-crystal can further decrease the amount of 4b in the bulk material.

This disclosure refers to patterns, such as XRPD patterns, in terms of their characteristic peaks. The assemblage of such peaks is unique to a given co-crystal form within the uncertainties attributable to individual instruments and to experimental conditions. Thus, for instance, each XRPD peak is disclosed in terms of an angle 2θ that has an acceptable uncertainty of ±0.2 °2θ, it being therefore understood that variances of characteristic peaks within this uncertainty in no way undercut the identity of a co-crystal form with a corresponding assemblage of its characteristic peaks.

Pharmaceutical Composition

The disclosure also contemplates as another embodiment a pharmaceutical composition that comprises a co-crystal as described herein. As explained in the examples, the inventive co-crystal surprisingly exhibits much greater bioavailability than 4a alone, i.e., as the amorphous solid. Therefore, the pharmaceutical composition can be formulated to contain a lower concentration of co-crystal to achieve therapeutically the same effects, relative to formulations that contain amorphous 4a. By this benefit of the inventive co-crystal, therapeutically effective amounts of a co-crystal in a pharmaceutical composition provide a dose of about 0.1 mg to about 1000 mg, adjusted as necessary according to the weight of a subject. Typical dosages can vary from about 0.01 mg/kg to about 100 mg/kg per day.

The pharmaceutical composition further comprises, in accordance with accepted practices of pharmaceutical compounding, one or more pharmaceutically acceptable excipients, diluents, adjuvants, stabilizers, emulsifiers, preservatives, colorants, buffers, or flavor imparting agents, that in aggregate constitute a pharmaceutically acceptable carrier. In general, the pharmaceutical composition is prepared with conventional materials and techniques, such as mixing, blending, and the like. In principle, the pharmaceutically acceptable carrier can be a liquid so long as the co-crystal maintains constitutive and structural stability, such as by not dissolving in the carrier. In general, however, the pharmaceutically acceptable carrier and, hence, the composition as a whole are solids.

In accordance with some embodiments, the pharmaceutical composition further comprises one or more additional co-crystals as disclosed herein. For example, the composition comprises two forms, three forms, or four forms. An exemplary composition comprises Form B and Form D. Binary compositions, i.e., those containing just two forms, provide the forms in various weight ratios ranging from about 0.05:1 to about 1:0.05. Intermediate ratios and ranges also are contemplated, such as 0.2:1 to about 1:0.2, and 0.5:1 to about 1:0.5.

For tablet compositions, an inventive co-crystal in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. These formulations, and all other liquid formulations described herein, are subject to the limitations delineated above for preserving constitutive and structural integrity of the solid co-crystal.

The pharmaceutical composition is presented as a suspension in accordance with embodiments described below. The embodiments refer to a "stable suspension," meaning that a given co-crystal or combination of co-crystals maintains its characteristic features, e.g., XRPD peaks, even while in contact with other components of the suspension, i.e., by not dissolving in the liquid excipients of a suspension, not converting to another co-crystal or amorphous form, or both.

For aqueous suspensions the inventive co-crystal is admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin, or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth naturally-occurring phosphatides, for example soy bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs can be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic, parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The inventive co-crystals may also be administered in the form of suppositories for rectal administration of the co-crystal. These compositions can be prepared by mixing the co-crystal with a suitable non-irritating excipient which is solid at ordinary temperatures but liquid at the rectal temperature and will therefore melt in the rectum to release the co-crystal. Examples of such materials are cocoa butter and polyethylene glycols.

Compositions for parenteral administrations are administered in a sterile medium. Depending on the vehicle used and the concentration of the co-crystal in the formulation, the parenteral formulation can be a suspension of the co-crystal provided that particle size distribution of the co-crystal is appropriate for this mode of administration. Adjuvants such as local anesthetics, preservatives and buffering agents can also be added to parenteral compositions.

Methods of Use

One surprising advantage conferred by the inventive co-crystals, as evidenced by the appended examples, is the ability to manufacture large quantities of 4a in very high diastereomeric and chemical purities. This is especially important for the development of 4a in compliance, for example, with Good Manufacturing Practice (GMP) regulations promulgated by the U.S. Food and Drug Administration. By contrast, synthesis of amorphous 4a requires subsequent and laborious separation techniques, such as chromatography—and all crystallization attempts were unsuccessful as mentioned above—that are still inefficient at isolating 4a in high chemical and diastereomeric purities for GMP purposes. For these reasons, the inventive co-crystals and processes for making them provide large quantities of 4a that are useful in clinical trials and commercialization efforts.

Another advantage of the inventive co-crystals resides in the unexpectedly high bioavailability of 4a from the co-crystals in comparison to amorphous 4a. More specifically, in vivo administration of a co-crystal increased the bioavailability of 4a by a factor of about 1.5-2, relative to the same dose of amorphous 4a (see Examples 12 and 13). This feature of the inventive co-crystals is all the more surprising in view of, and in fact it stands in contrast to, the general observation that amorphous forms of pharmaceuticals are markedly more soluble and, hence, more bioavailable, than their crystalline counterparts. See, B. C. Hancock et at., *Pharm. Res.* 17(4) (2000) 397-404; B. C. Hancock et al., *J. Pharm. Sci.* 86(1) (1997) 1-12.

In light of these advantages, the present disclosure is further drawn to the use of any of the co-crystal forms, including pharmaceutical compositions thereof, for treating or preventing a neurodegenerative disorder in a subject that suffers from the disorder. Non-limiting examples of such neurodegenerative disorders include Alzheimer's disease, Parkinson's disease, amyotrophic lateral sclerosis (ALS), Huntington's disease, spinal muscular atrophy, spinocerebellar ataxia and forms of ataxia, and demyelinating nerve disorders including motor neuron diseases. In addition, the co-crystal forms and their pharmaceutical compositions are useful in the treatment of diabetic neuropathy (including both the painful and insensate forms thereof) and other forms of neuropathy, including neuropathic pain that is not due to diabetes.

The co-crystal forms and their pharmaceutical compositions are also useful in treating neurological disorders involving mitochondrial dysfunction, oxidative stress, or inflammation, in light of the reported use of compound 4a to improve impaired mitochondrial function in neurons and to reduce the expression of inflammatory markers in diabetic neurons (Ma (2015)). Because diabetic tissues undergo significant oxidative stress, these results indicate that the inventive co-crystal forms and their pharmaceutical compositions are useful in treating other neurological disorders that involve oxidative stress and chronic inflammation, including epilepsy, multiple sclerosis, spinal cord injury, and psychiatric disorders including schizophrenia, depression, bipolar disorder, autism and related disorders, and post-traumatic stress disorders. The compositions and co-crystal forms can be used in combination with other therapies, particularly therapies that reduce oxidative stress, inflammation, and mitochondrial dysfunction by other mechanisms.

As the term is used herein, "neurodegenerative disorder" refers to a disorder in which progressive loss of neurons occurs either in the peripheral nervous system or in the central nervous system. Thus, in one embodiment, the disclosure provides a method for inhibiting Hsp90 in a subject, such as during or pursuant to the treatment of the neurodegenerative disorder, by inhibiting the progressive deterioration of neurons that leads to cell death.

A method as described herein comprises administering to the subject a therapeutically effective amount of an inventive co-crystal. Within the dosing guidelines set forth above, a "therapeutically effective amount" is an amount of a co-crystal that inhibits, totally or partially, the progression of the disorder or alleviates, at least partially, one or more symptoms of the disorder. A therapeutically effective amount can also be an amount that is prophylactically effective. The amount that is therapeutically effective will depend upon the patient's size and gender, the disorder to be treated, the severity of the disorder and the result sought. For a given patient and disorder, a therapeutically effective amount can be determined by methods known to those of skill in the art.

In various embodiments, a method entails prevention of a neurological disorder. The term "preventing" or "prevention" as used herein means that an inventive co-crystal is useful when administered to a subject who has not been diagnosed as possibly having the disorder at the time of administration, but who would normally be expected to develop the disorder or be at increased risk for the disorder. An inventive co-crystal slows the development of the disorder symptoms, delays the onset of the disorder, or prevents the subject from developing the disorder at all. Prevention also contemplates the administration of a co-crystal to a subject who is thought to be predisposed to the disorder due to age, familial history, genetic or chromosomal abnormalities, and/or due to the presence of one or more biological markers for the disorder.

In other embodiments, an inventive method entails "treatment" or "treating," meaning that a co-crystal is used in a subject with at least a tentative diagnosis of the disorder. Hence, the co-crystal of the invention delays or slows the progression of the disorder. In addition, the term "treatment" embraces at least an amelioration of the symptoms associated with the disorder, where amelioration is used in a broad sense to refer to at least a reduction in the magnitude of a parameter, e.g. symptom, associated with the condition being treated. As such, "treatment" also includes situations where the disorder, or at least symptoms associated therewith, are completely inhibited, e.g. prevented from happening, or stopped, e.g. terminated, such that the subject no longer suffers from the disorder, or at least the symptoms that characterize the disorder.

In one embodiment, the neurodegenerative disorder is sensory neuron glucotoxicity resultant from, e.g., hyperglycemia associated with a diabetic condition. For example, a subject suffers from Type 1 or Type 2 diabetes. More specifically, in accordance with an embodiment, the neurodegenerative disorder is diabetic peripheral neuropathy. Thus, in an embodiment, an inventive method comprises preventing or reducing the likelihood of diabetic peripheral neuropathy from developing in a subject who suffers from Type 1 or Type 2 diabetes.

In the context of the inventive methods and uses, the "subject" to be treated with an inventive co-crystal is an animal and is preferably a mammal, e.g., dogs, cats, mice, monkeys, rats, rabbits, horses, cows, guinea pigs, sheep. In an embodiment, the subject is a human.

EXAMPLES

The following non-limiting examples are provided to illustrate additional embodiments of the present disclosure.

Amorphous 4a in about 95% purity (HPLC) is obtained, for example, in accordance with published procedures (Kusuma (2012) and U.S. Pat. No. 9,422,320).

I. General Crystallization Experimental Methods

Crash Precipitation (CP): Solutions of 4a were prepared in various solvents or solvent systems with various coformers in given molar ratios with agitation. Aliquots of various antisolvents were dispensed with stirring until precipitation occurred. Mixtures were allowed to stir for a specified period of time. Where stated, additional crystallization techniques were employed.

Fast Evaporation (FE): Solutions of 4a were prepared in various solvents with various coformers in given molar ratios with agitation. Each solution was allowed to evaporate from an open vial at ambient conditions unless otherwise stated. Solutions were allowed to evaporate to dryness unless designated as partial evaporations (solid present with a small amount of solvent remaining), in which case solids were isolated by the stated method or additional crystallization techniques were employed as stated.

Manual Grinding: Weighed amounts of 4a and various coformers were transferred to an agate mortar. A small amount of a given solvent was added to the solids, and the mixtures were manually ground with an agate pestle for a given amount of time.

Milling: Weighed amounts of 4a and given coformers were transferred to agate milling containers. A small amount of given solvent and an agate milling ball were added to the containers, which were then attached to a Retsch mill. The mixtures were milled at 30 $s^{-1}$ for the stated duration. The solids were scraped down the walls of the jar between cycles.

Reaction Crystallization (RC): Mixtures of 4a with various coformers were prepared in a given solvent by adding solids of one component to a solution of the second component. When enough solids were added such that the solution contained differing concentrations of each component (generally a 10- to 20-fold difference in molarity of one component vs. the other), the solution was allowed to stir for an extended period of time. When specified, additional solids of the more concentrated component were added if no precipitation occurred, and the mixture was again allowed to stir for an extended period of time. Any precipitated solids were isolated and analyzed.

Slow Cool (SC): Concentrated solutions of 4a were prepared in various solvent systems with various coformers in given molar ratios at elevated temperatures with stirring. Each vial was capped and left on the hot plate, and the hot plate was turned off to allow the sample to slowly cool to ambient temperature. If no solids were present after cooling to ambient temperature, the sample was placed in the refrigerator (approximately 2 to 8° C.) and/or the freezer (approximately −10 to −25° C.) for further cooling. If no solids were present, additional crystallization techniques were employed, as specified.

Slow Evaporation (SE): Solutions of 4a were prepared in various solvent systems with various coformers in given molar ratios. Each solution was allowed to evaporate at ambient conditions in a vial covered with aluminum foil perforated with pinholes. Solutions were allowed to evaporate to dryness unless designated as partial slow evaporations, in which a portion of the solvent evaporated. Resulting solids were isolated by the stated technique or additional crystallization techniques were employed, where stated.

Slurry Experiments: Suspensions of 4a with various coformers in stated molar ratios were prepared by adding enough solids to a given solvent system at ambient conditions such that undissolved solids were present. The mixtures were then agitated (typically by stirring) in a sealed vial at the stated conditions for an extended period of time. Solids were collected by the stated technique or additional crystallization techniques were employed where stated.

Vapor Diffusion (VD): Concentrated solutions of given starting materials (either a given form of 4a/L-proline or stated stoichiometric mixtures of 4a and L-proline) were prepared in various solvents. In some cases, solutions were filtered through a 0.2-μm nylon filter. Each solution was dispensed into a small vial, which was then placed inside a larger vial containing a given antisolvent. Where stated, seeds of a given 4a/L-proline form were added to the solutions. The small vial was left uncapped and the larger vial was capped to allow vapor diffusion to occur. Where stated, additional crystallization techniques were attempted.

Vacuum Filtration: Solids were collected on paper or nylon filters by vacuum filtration and air dried on the filters under reduced pressure briefly before transferring to a vial.

Interconversion Slurries: Solutions of given starting materials (either a given 4a/L-proline form or stated stoichiometric mixtures of 4a and L-proline) were prepared by adding solids to a given solvent system at a stated temperature. If a saturated solution was specified, the suspension was agitated at ambient temperature for an extended period of time to ensure saturation of the liquid phase. Seed crystals of each of the given 4a/L-proline forms of interest were added to the prepared solutions (or to the filtered liquid phase from a saturated solution) such that undissolved solids were present. Each mixture was then agitated (typically by stirring) in a sealed vial at a stated temperature for a given duration. The solids were isolated by vacuum filtration and analyzed.

II. X-ray Powder Diffraction (XRPD) Peak Identification

Throughout this disclosure are x-ray diffraction patterns and tables with peak lists. Peaks within the range of up to about 30° 2θ were selected. Rounding algorithms were used to round each peak to the nearest 0.01° 2θ. The location of the peaks along the x-axis (°2θ) in both the figures and the lists were determined using proprietary software (TRIADS™ v2.0) and rounded to two significant figures after the decimal point. Peak position variabilities are given to within ±0.2° 2θ based upon recommendations outlined in the USP discussion of variability in x-ray powder diffraction (United States Pharmacopeia, USP 38-NF 33 through S2, <941> Dec. 1, 2015). The accuracy and precision associated with any particular measurement disclosed herein has not been determined. Moreover, third party measurements on independently prepared samples on different instruments may lead to variability which is greater than ±0.2° 2θ. The wavelength used to calculate d-spacings was 1.5405929 Å, the Cu-$K_{\alpha 1}$ wavelength (Holzer, G.; Fritsch, M.; Deutsch, M.; Hartwig, J.; Forster, E. Phys. Rev. 1997, A56 (6), 4554-4568). Variability associated with d-spacing estimates was calculated from the USP recommendation, at each d-spacing, and provided in the respective data tables.

Per USP guidelines, variable hydrates and solvates may display peak variances greater than 0.2° 2θ and therefore peak variances of 0.2° 2θ are not applicable to these materials.

For samples with only one XRPD pattern and no other means to evaluate whether the sample provides a good approximation of the powder average, peak tables contain data identified only as "Prominent Peaks". These peaks are a subset of the entire observed peak list. Prominent peaks are selected from observed peaks by identifying preferably non-overlapping, low-angle peaks, with strong intensity.

Where multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

Instrumental Techniques

Differential Scanning Calorimetry (DSC): DSC was performed using a TA Instruments Q2000 differential scanning calorimeter. Temperature calibration was performed using NIST-traceable indium metal. A sample was placed into an aluminum Tzero crimped DSC pan, covered with a lid, and the weight was accurately recorded. A weighed aluminum pan configured as the sample pan was placed on the reference side of the cell.

Dynamic Vapor Sorption (DVS): Dynamic vapor sorption data were collected on a VTI SGA-100 Vapor Sorption Analyzer. NaCl and polyvinypyrrolidone (PVP) were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

EasyMax™ Reactor: Crystallization experiments were performed using the Mettler Toledo EasyMax™ 102 with Julabo F26 chiller/circulator. Crystallizations were performed in 20 mL glass tubes (capped) with magnetic stirring. The temperature was controlled using the jacket temperature (Tj) setting.

Elemental Analysis: Elemental analyses were carried out by Galbraith Laboratories, Knoxville, Tenn.

Infrared Spectroscopy: IR spectra were acquired on Nicolet 6700 Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 $cm^{-1}$. A background data set was acquired with a clean Ge crystal. A Log 1/R (R=reflectance) spectrum was obtained by taking a ratio of these two data sets against each other.

Raman Spectroscopy: Raman spectra were acquired on a FT-Raman module interfaced to a Nexus 670 FT-IR spectrophotometer (Thermo Nicolet) equipped with an indium gallium arsenide (InGaAs) detector. Wavelength verification was performed using sulfur and cyclohexane. Each sample was prepared for analysis by placing the sample into a pellet holder. Approximately 0.514 W of Nd:$YVO_4$ laser power (1064 nm excitation wavelength) was used to irradiate the sample. Each spectrum represents 256 co-added scans collected at a spectral resolution of 4 $cm^{-1}$.

Single Crystal X-Ray Diffraction (SCXRD): The single crystal structures of 4a/L-proline Form B and Form C were determined at the Crystallography Laboratory at Purdue University.

Thermogravimetry (TGA): TG analyses were performed using a TA Instruments 2050 or a Discovery thermogravimetric analyzer. Temperature calibration was performed using nickel and Alumel™. Each sample was placed in an aluminum or platinum pan and inserted into the TG furnace. The furnace was heated under a nitrogen purge from ambient temperature to 350° C. at a heating rate of 10° C./min.

Optical Microscopy: Samples were observed under a Wolfe optical microscope with crossed polarizers at either 2× or 4× objectives or under a Leica stereomicroscope with a first order red compensator with crossed polarizers at 0.8× to 10× objectives.

Solution $^1$H NMR Spectroscopy: The solution $^1$H NMR spectra were acquired by Spectral Data Services of Champaign, Ill. at 25° C. with a Varian $^{UNITY}$INOVA-400 spectrometer. The samples were dissolved in DMSO-$d_6$. The residual peak from incompletely deuterated DMSO is at approximately 2.5 ppm, and a relatively broad peak at approximately 3.3 ppm is due to water.

X-Ray Powder Diffraction (XRPD)

PANalytical X'PERT Pro MPD Diffractometer—Transmission Geometry (Most Samples): XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

PANalytical X'PERT Pro MPD Diffractometer—Reflection Geometry (Samples in Limited Quantity): XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

HPLC Procedures

The following table presents parameters and conditions for HPLC described herein. Reported HPLC purities of 4a and 4b do not take into account a peak for proline.

| Column | Thames Restek Raptor C18 150 × 4.6 mm, 2.7 μm |
|---|---|
| Mobile phase A | Water |
| Mobile phase B | Acetonitrile |
| Flow rate | 1.0 mL/min |
| UV Wavelength | 215 nm |
| Column Temperature | 40° C. |
| Injection Volume | 10 μL |
| Runtime | 40 minutes |

| Gradient | | |
|---|---|---|
| Time (mins) | Mobile Phase A (%) | Mobile Phase B (%) |
| 0 | 90 | 10 |
| 3 | 90 | 10 |
| 33 | 10 | 90 |
| 35 | 10 | 90 |
| 37 | 90 | 10 |
| 40 | 90 | 10 |

Example 1

Synthesis of 4a/L-Proline Co-crystal (Material A)

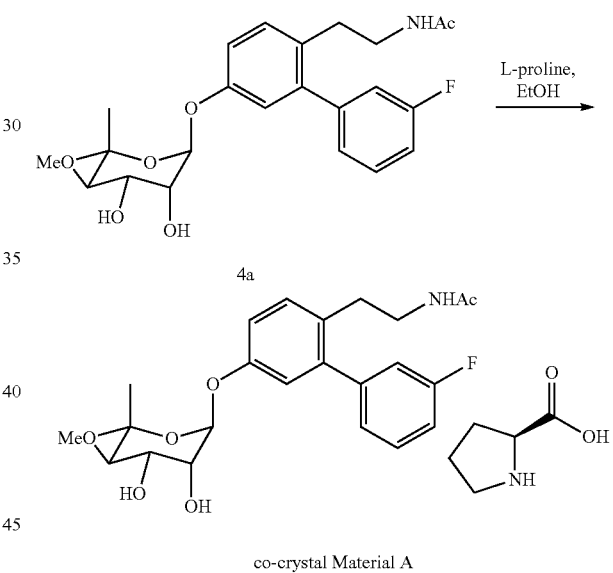

co-crystal Material A

Compound 4a was obtained by chromatographic separation (HPLC: 4a 96.4% and 4b 1.2%, 500 mg) and was mixed with L-proline (128 mg, 1 eq.) in EtOH (4 mL). The mixture was heated at reflux for 15 min. The hot solution was filtered through a cotton plug. The resulting clear filtrate was cooled slowly and kept at room temperature for 16 h. The precipitated solid was collected by filtration, and dried in air at room temperature to give a 4a/L-proline co-crystal that was designated as Material A (456 mg, 73% yield) as a white solid. M.P. 203-205° C. $^1$H NMR indicated a ratio of 4a to L-proline as 1:1.1.

Material A is a 1:1 4a/L-proline cocrystal and it is likely an isostructural solvate. Material A contains a minor L-proline component based on the XRPD pattern (FIG. 23), which was successfully indexed (Table A1). XRPD indexing is typically successful for samples consisting primarily or exclusively of a single crystalline phase. However, an indexing solution was obtained for this mixture with the understanding that the minor peaks/shoulders present in the XRPD pattern at 8.7°, 15.0°, and 18.0° 2θ are not consistent with the indexing solution and are likely attributable to L-proline. Select unit cell parameters obtained from the indexing solution are presented in Table A2.

TABLE A1

Observed peaks for 4a/L-proline Material A

| °2θ | d space (Å) | Intensity (%) |
|---|---|---|
| 5.81 ± 0.20 | 15.189 ± 0.522 | 6 |
| 8.52 ± 0.20 | 10.369 ± 0.243 | 100 |
| 9.19 ± 0.20 | 9.613 ± 0.209 | 63 |
| 9.92 ± 0.20 | 8.913 ± 0.179 | 23 |
| 10.49 ± 0.20 | 8.426 ± 0.160 | 7 |
| 11.68 ± 0.20 | 7.568 ± 0.129 | 57 |
| 11.87 ± 0.20 | 7.451 ± 0.125 | 65 |
| 12.21 ± 0.20 | 7.244 ± 0.118 | 29 |
| 13.22 ± 0.20 | 6.691 ± 0.101 | 67 |
| 14.75 ± 0.20 | 5.999 ± 0.081 | 73 |
| 16.07 ± 0.20 | 5.510 ± 0.068 | 18 |
| 16.33 ± 0.20 | 5.422 ± 0.066 | 78 |
| 16.68 ± 0.20 | 5.312 ± 0.063 | 20 |
| 17.10 ± 0.20 | 5.181 ± 0.060 | 45 |
| 17.57 ± 0.20 | 5.044 ± 0.057 | 54 |
| 18.32 ± 0.20 | 4.839 ± 0.052 | 29 |
| 18.54 ± 0.20 | 4.783 ± 0.051 | 27 |
| 18.87 ± 0.20 | 4.698 ± 0.049 | 30 |
| 19.26 ± 0.20 | 4.605 ± 0.047 | 39 |
| 19.50 ± 0.20 | 4.548 ± 0.046 | 75 |
| 19.65 ± 0.20 | 4.514 ± 0.045 | 35 |
| 20.17 ± 0.20 | 4.399 ± 0.043 | 27 |
| 20.34 ± 0.20 | 4.363 ± 0.042 | 46 |
| 21.22 ± 0.20 | 4.183 ± 0.039 | 70 |
| 21.79 ± 0.20 | 4.076 ± 0.037 | 21 |
| 22.08 ± 0.20 | 4.023 ± 0.036 | 8 |
| 22.34 ± 0.20 | 3.976 ± 0.035 | 8 |
| 22.61 ± 0.20 | 3.930 ± 0.034 | 6 |
| 23.51 ± 0.20 | 3.781 ± 0.032 | 35 |
| 23.79 ± 0.20 | 3.738 ± 0.031 | 50 |
| 24.58 ± 0.20 | 3.619 ± 0.029 | 26 |
| 24.88 ± 0.20 | 3.576 ± 0.028 | 15 |
| 25.12 ± 0.20 | 3.542 ± 0.028 | 13 |
| 25.48 ± 0.20 | 3.493 ± 0.027 | 24 |
| 25.96 ± 0.20 | 3.430 ± 0.026 | 8 |
| 26.20 ± 0.20 | 3.398 ± 0.025 | 16 |
| 26.45 ± 0.20 | 3.367 ± 0.025 | 9 |
| 27.28 ± 0.20 | 3.266 ± 0.023 | 6 |
| 27.63 ± 0.20 | 3.225 ± 0.023 | 14 |
| 27.85 ± 0.20 | 3.201 ± 0.023 | 11 |
| 28.27 ± 0.20 | 3.154 ± 0.022 | 11 |
| 28.40 ± 0.20 | 3.140 ± 0.022 | 14 |
| 29.04 ± 0.20 | 3.072 ± 0.021 | 6 |
| 29.46 ± 0.20 | 3.029 ± 0.020 | 5 |
| 29.78 ± 0.20 | 2.998 ± 0.020 | 14 |

TABLE A2

Unit Cell Parameters for 4a/L-proline Material A

| Bravais Type | Primitive Orthorhombic |
|---|---|
| a [Å] | 10.126 |
| b [Å] | 11.021 |
| c [Å] | 30.259 |
| α [deg] | 90 |
| β [deg] | 90 |
| γ [deg] | 90 |
| Volume [Å$^3$/cell] | 3,376.9 |
| Chiral Contents? | Chiral |
| Extinction Symbol | P $2_1$ $2_1$ – |
| Space Group(s) | P$2_1$$2_1$2 (18) |

The unit cell volume is large enough to accommodate a solvated 1:1 4a/L-proline cocrystal. The free volume (or the unit cell volume remaining after the cocrystal is accounted for) could possibly fit water and/or any of the solvents from which Material A was produced, including EtOH, IPA, and THF.

Figure 24:
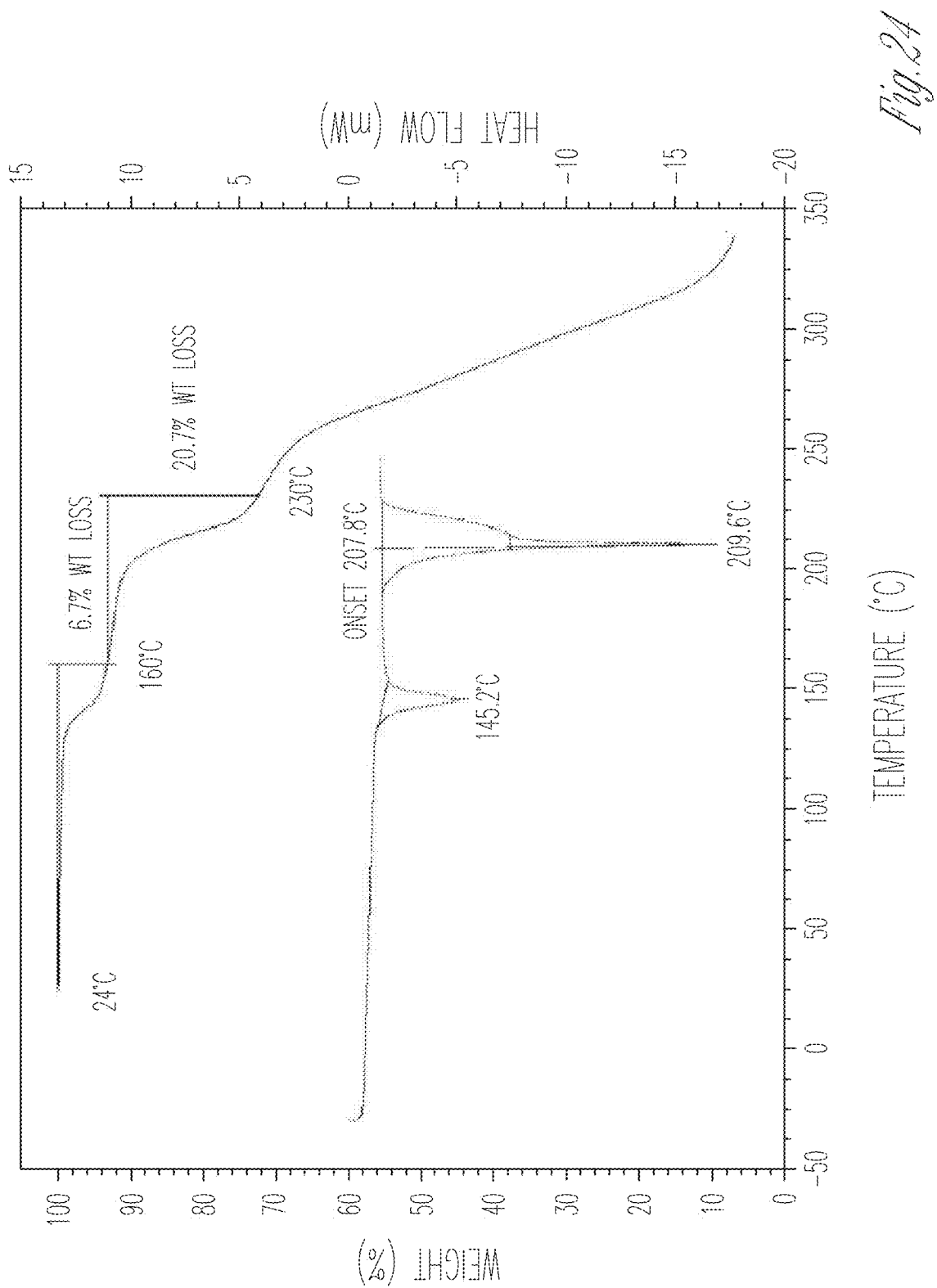
FIG. 24 shows DSC (bottom trace) and TGA (top trace) curves of 4a/L-proline co-crystal Material A.

Material A as described above was additionally characterized by DSC, TGA, and DVS. An overlay of DSC and TGA thermograms for the material is shown in FIG. 24. The TGA thermogram exhibits two distinct weight loss steps, the first occurring between ~100 and 160° C. (7 wt %) and the second between 160 and 230° C. (21 wt %). A broad endotherm is observed by DSC with a peak maximum at 145° C., which corresponds to the first TGA weight loss step. The relatively high temperatures at which these events occur as well as the stepwise nature of the weight loss likely indicate the loss of bound solvent/water. Overlapping endothermic events between ~170 and ~240° C. by DSC correspond to the second weight loss step in the TGA thermogram, likely corresponding with concurrent melting of the cocrystal and volatilization of the L-proline component. The steep drop in the TGA thermogram above ~250° C. likely corresponds with decomposition.

Figure 25:
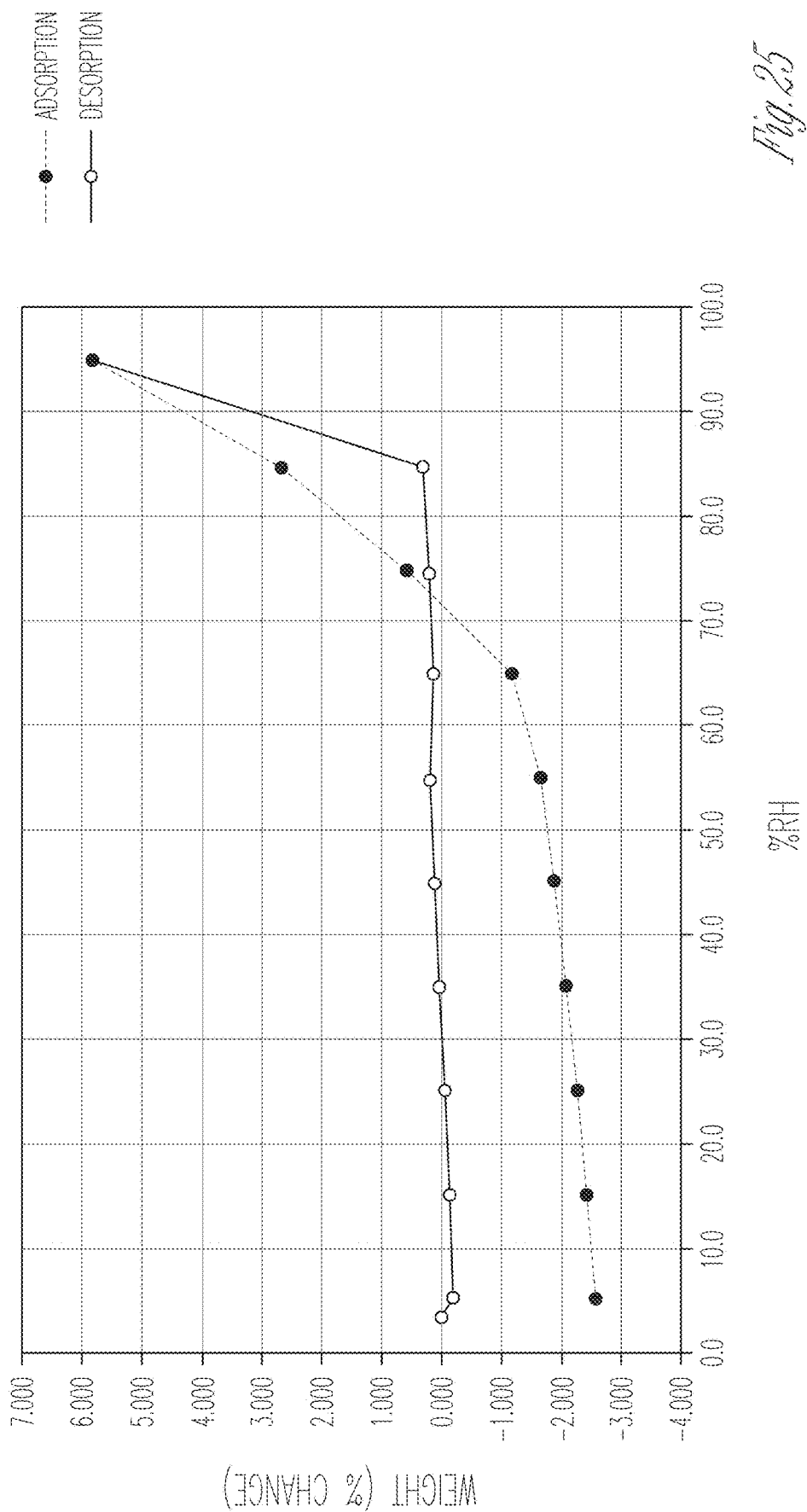
FIG. 25 is a dynamic vapor sorption (DVS) curve of 4a/L-proline co-crystal Material A.

A DVS isotherm for Material A as described above is presented in FIG. 25. Because the material was characterized as a mixture with unreacted L-proline, it is unknown what effect, if any, the excess L-proline might have had on the vapor sorption behavior. The material exhibits significant hygroscopicity at or above 85% RH, taking up ~6 wt % water vapor between 85% and 95% RH. The vapor sorption kinetic equilibration timed out at 85%-95% RH, indicating that the cocrystal could potentially pick up more moisture than what was measured if it was allowed a longer equilibration time. Relatively steady weight loss was noted upon desorption between 95% and 5% RH. The weight lost upon desorption (~8 wt %) was significantly higher than that gained during sorption, indicating the material was likely solvated/hydrated at the start of the analysis. Analysis of the post-DVS material by XRPD showed a decrease in crystallinity, although the solid form remained intact. The presence or absence of excess L-proline in the post-DVS sample could not be confirmed due to the disorder in the XRPD pattern.

Example 2

Purification of 4a by Co-Crystallization with L-Proline

A 500 mg mixture of 4 consisting of compounds 4a and 4b (HPLC: 92.0% of 4a and 7.1% 4b) and L-proline (128 mg, 1 eq) in ethanol (4 mL) was refluxed for 15 min. The mixture was seeded with a co-crystal obtained in Example 1, and the mixture was allowed to cool and then kept at room temperature for 18 h. A white solid was filtered off, while residual solid was transferred out of the reaction flask with the mother liquor. The collected quantity of 4a/L-proline co-crystal (1:1 ratio as determined by $^1$H-NMR, 497 mg, 79% yield) consisted of 98.0% 4a and 1.49% 4b (analyzed by HPLC).

Example 3

Co-Crystal Screen

Amorphous 4a was utilized in approximately 50 co-crystal screen experiments with 26 co-formers other than L- and D-proline, as summarized in Table 1 below. A variety of crystallization techniques amenable to co-crystal formation was employed, including solvent-assisted milling and manual grinding, cooling, evaporation, slurry, crash precipitation, and reaction crystallization, in which a solution containing a high molar excess of one component is combined with another component to encourage the reaction equilibrium to favor co-crystal formation. A variety of coformers possessing functional groups capable of forming hydrogen bonds was utilized, including carboxylic acids, amino acids, sugars, amides, amines, and numerous functional aromatic compounds. Under the variety of conditions and coformers explored in this screen, however, 4a did not form any confirmed co-crystals with these common coformers.

TABLE 1

| Coformer | 4a/Coformer Molar Ratio | Conditions | Technique | Results |
|---|---|---|---|---|
| acetic acid | ~1:66 | 1) add glacial acetic acid to 4a solids w/stirring<br>2) RC (stir), RT, 3 days<br>3) ref., 73 days | Obs | 1) solids turned light blue and then dissolved, clear light bluish soln.<br>2) clear soln.<br>3) clear soln. |
| L-arginine | 1:5 | 1) dissolve L-arginine in water, add to 4a<br>2) RC (stir), RT, 3 days<br>3) add 5 mol. eq. L-arginine | Obs | 1) undissolved solids present<br>2) clear liquid phase, off-white gummy solids on stir bar<br>3) undissolved solids present |
| | 1:10 | 4) RC (stir), RT, 4 days | | 4) clear liquid phase, gummy solids stuck to stir bar |
| L-arginine | 1:1 | 1) mill 4a w/MeOH at 30 Hz for 3 × 10-min. cycles<br>2) dry under $N_2$ 1 day | Obs | 1) sticky goo<br>2) sticky goo |
| caffeine | 1:2 | 1) add MEK to 4a and coformer solids w/stirring at ~74° C.<br>2) SC, ~74° C. to RT, stand at RT, 1 day<br>3) poke w/spatula<br>4) vac. filter | Obs<br><br><br><br><br>OM<br>XRPD | 1) clear soln.<br>2) large mass of off-white solids, small amt. liquid visible<br>3) liquid released from solids<br>4) white solids<br>needles, B/E<br>caffeine |
| caffeine | 1:1 | manually grind 4a w/ acetone 4 min. | Obs<br>OM<br>XRPD | free-flowing off-white solids<br>fines and aggregates, partial B/E<br>caffeine + amorphous |
| carbamazepine | 1:1 | 1) add EtOAc to 4a and coformer solids w/stirring at ~75° C.<br>2) SC, ~75° C. to RT, stir at RT 3 days<br>3) vac. filter | Obs<br><br><br><br>OM<br>XRPD | 1) clear soln.<br>2) opaque white suspension, white solids on walls<br>3) white solids<br>fines and aggregates, B/E<br>carbamazepine |
| citric acid | 1:5 | 1) dissolve citric acid in EtOH, add to 4a<br>2) RC (stir), RT, 3 days<br>3) add 5 mol. eq. citric acid | Obs | 1) clear soln.<br>2) clear soln.<br>3) clear soln.<br>4) clear soln. |
| | 1:10 | 4) RC (stir), RT, 4 days<br>5) add 10 mol. eq. citric acid | | 5) clear soln.<br>6) clear soln. |
| | 1:20 | 6) RC (stir), RT, 46 days | | |
| D-fructose | 1:5 | 1) dissolve D-fructose in MeOH, add to 4a<br>2) RC (stir), RT, 3 days<br>3) add 5 mol. eq. fructose | Obs | 1) clear soln.<br>2) clear soln.<br>3) undissolved solids present<br>4) clear soln. |
| | 1:10 | 4) RC (stir), RT, 4 days<br>5) add 10 mol. eq. fructose | | 5) undissolved solids present<br>6) clear liquid phase, white solids |
| | 1:20 | 6) RC (stir), RT, 16 days<br>7) vac. filter | <br>OM<br>XRPD | 7) white solids<br>fines and aggregates, B/E<br>D-fructose |
| fumaric acid | 1:2 | 1) add EtOH to 4a and acid solids w/stirring at ~74° C.<br>2) SC, ~74° C. to RT, stir at RT 1 day<br>3) vac. filter | Obs<br><br><br>OM<br>XRPD | 1) clear soln.<br>2) cloudy white suspension<br>3) white solids<br>fines and aggregates, B/E<br>fumaric acid |
| fumaric acid | 1:10 | 1) dissolve acid in THF, add to 4a<br>2) RC (stir), RT, 3 days<br>3) add 10 mol. eq. fumaric acid | Obs | 1) clear soln.<br>2) clear soln.<br>3) undissolved solids present<br>4) clear liquid phase, white solids<br>5) white solids |
| | 1:20 | 4) RC (stir), RT, 12 days<br>5) vac. filter | <br>OM<br>XRPD | <br>fines and aggregates, B/E<br>fumaric acid |

TABLE 1-continued

| Coformer | 4a/Coformer Molar Ratio | Conditions | Technique | Results |
|---|---|---|---|---|
| gentisic acid | 1:3 | 1) dissolve 4a and acid in ACN<br>2) stir, RT, 1 day<br>3) add MTBE w/stirring (ACN/MTBE 1:3)<br>4) stir, RT, 3 days<br>5) SE<br>6) vac. oven, RT, 3 days | Obs<br><br><br><br><br><br><br>OM (after step 5)<br>OM (after step 6)<br>XRPD | 1) clear soln.<br>2) clear soln.<br>3) soln. became very slightly cloudy, then cleared<br>4) clear, slightly amber soln.<br>5) large crystals embedded in sticky amber oil<br>6) bubbly off-white solids<br>numerous plates (likely singles), B/E; oil, no B/E<br>unknown morphology, no B/E; plates, B/E<br>gentisic acid |
| L-glutamic acid | 1:2 | 1) add EtOH and water (1:2) to 4a w/stirring at ~75° C.<br>2) hot filter<br>3) SC, ~75° C. to RT, stand at RT 4 days<br>4) ref., 6 days<br>5) decant liquid, dry solids briefly under N$_2$ | Obs<br><br><br><br><br><br>OM<br><br>XRPD | 1) slightly hazy soln.<br>2) clear soln.<br>3) clear soln.<br>4) clear liquid phase, white solids on bottom<br>5) damp white solids<br>irregular plates and agglomerates, B/E<br>L-glutamic acid |
| glycine | 1:2<br><br><br><br>1:1<br><br>1.5:1 | 1) dissolve 4a in EtOH<br>2) add 4a soln. to glycine<br>3) slurry, RT, 4 days<br>4) add 4a to 1:1<br>5) stir, RT, 3 days<br>6) add 4a to 1.5:1<br>7) stir, RT, days<br>8) vac. filter | Obs<br><br><br><br><br><br><br><br><br><br><br><br>OM<br>XRPD | 1) clear soln.<br>2) undissolved solids present<br>3) cloudy suspension, large crystals on bottom (likely glycine)<br>4) cloudy<br>5) cloudy suspension, few large crystals (likely glycine) present<br>6) cloudy<br>7) cloudy suspension, minimal large crystals on bottom<br>8) white solids<br>fines, aggregates, and tablets, B/E<br>glycine |
| glycine | 1:2 | 1) mill 4a w/toluene at 30 Hz for 3 × 10-min. cycles<br>2) dry under N$_2$ 1 day | Obs | 1) sticky goo and white solids<br>2) off-white sticky goo |
| hippuric acid | 1:1 | 1) add MEK to 4a and acid solids w/stirring at ~74° C.<br>2) SC, ~74° C. to RT, stand at RT, 1 day<br>3) decant liquid, dry solids briefly under N$_2$ | Obs<br><br><br><br><br>OM<br><br>XRPD | 1) clear soln.<br>2) clear liquid phase, white solids coating bottom<br>3) white solids<br>rectangular plates and aggregates, B/E<br>hippuric acid |
| trans-4-hydroxy-L-proline | 5:1 | 1) dissolve 4a in EtOH<br>2) add 4a soln. to coformer solids w/stirring<br>3) RC (stir), RT, 6 days<br>4) vac. filter | Obs<br><br><br><br><br>OM<br>XRPD | 1) slightly hazy light yellow soln.<br>2) small amt. undissolved solids present<br>3) opaque off-white suspension<br>4) white solids<br>fines and aggregates, no B/E<br>trans-4-hydroxy-L-proline |
| D-(−)-isoascorbic acid | 1:2 | 1) add EtOH to 4a and acid solids w/stirring at ~75° C.<br>2) SC, ~75° C. to RT, stir at RT 3 days<br>3) vac. filter | Obs<br><br><br><br>OM<br>XRPD | 1) clear soln.<br>2) opaque white suspension, white solids on walls<br>3) white solids<br>fines and aggregates, B/E<br>D-isoascorbic acid |
| lactic acid | ~1:48 | 1) add conc. lactic acid to 4a solids w/stirring<br>2) RC (stir), RT, 3 days<br>3) ref., 73 days | Obs | 1) thick suspension, undissolved solids present<br>2) clear soln.<br>3) clear soln. |
| nicotinamide | 1:3 | 1) dissolve 4a and acid in MEK<br>2) stir, RT, 1 day<br>3) partial SE<br>4) decant liquid, dry solids briefly under N$_2$ | Obs<br><br><br><br><br><br>OM<br>XRPD | 1) clear soln.<br>2) clear soln.<br>3) small amt. clear liquid phase, off-white solids on bottom and sides<br>4) sticky white solids<br>thin needles, B/E<br>nicotinamide |

TABLE 1-continued

| Coformer | 4a/Coformer Molar Ratio | Conditions | Technique | Results |
|---|---|---|---|---|
| nicotinamide | 1:20 | 1) dissolve nicotinamide in MeOH, add to 4a<br>2) RC (stir), RT, 1 day<br>3) vac. filter | Obs<br><br>OM<br>XRPD | 1) clear soln.<br>2) clear liquid phase, white solids present<br>3) white solids<br>needles and aggregates, B/E nicotinamide |
| oxalic acid | 1:10<br><br><br>1:20 | 1) add ACN to 4a and acid solids w/sonication<br>2) RC (stir), RT, 2 days<br>3) add 10 mol. eq. acid<br>4) RC (stir), RT, 11 days<br>5) decant liquid phase, dry solids under $N_2$ | Obs<br><br><br><br><br><br>OM<br>XRPD | 1) slightly hazy soln.<br>2) clear soln.<br>3) undissolved solids present<br>4) clear amber liquid phase, white solids present<br>5) white solids<br>fines and aggregates, B/E oxalic acid |
| L-phenylalanine | 1:2 | 1) add EtOH to 4a and coformer solids w/stirring at ~73° C.<br>2) add water to EtOH/water 50:50<br>3) SC, ~73° C. to RT, stir at RT 1 day<br>4) vac. filter | Obs<br><br><br><br>OM<br><br>XRPD | 1) undissolved solids<br>2) slightly hazy suspension<br>3) cloudy suspension (opaque)<br>4) white solids<br>fine needles and aggregates, B/E<br>L-phenylalanine hemihydrate |
| piperazine | 1:1 | 1) manually grind 4a w/acetone 4 min.<br>2) dry under $N_2$ gas for 2 min. | Obs | 1) sticky film<br>2) sticky film, could not be scraped from mortar and pestle |
| piracetam | 1:2 | 1) add EtOH to 4 a and coformer solids w/stirring at ~75° C.<br>2) SC, ~75° C. to RT, stir at RT 3 days | Obs<br><br><br>OM<br>XRPD | 1) clear soln.<br>2) opaque off-white suspension<br>3) white solids<br>fines and aggregates, B/E piracetam |
| L-prolinamide | 1:2 | 1) add EtOH to 4a and coformer solids w/stirring at ~75° C.<br>2) SC, ~75° C. to RT, stir at RT 3 days<br>3) freezer, 7 days<br>4) SE<br>5) add diethyl ether<br>6) slurry (stir), RT, 22 days | Obs | 1) clear yellow soln.<br>2) clear yellow soln.<br>3) clear yellow soln.<br>4) sticky yellow oil<br>5) clear liquid phase, yellow oil<br>6) clear liquid phase, yellow oil on bottom |
| L-prolinamide | 1:2 | 1) add ACN to 4a and coformer solids w/stirring at ~73° C.<br>2) SC, ~73° C. to RT, stir at RT 1 day<br>3) freezer, 16 days<br>4) SE<br>5) add IPE w/stirring<br>6) stir, RT, 3 days | Obs | 1) clear yellow soln.<br>2) clear yellow soln., translucent film on walls<br>3) yellow liquid phase, small amt. solids<br>4) stick yellow oil<br>5) clear liquid, yellow oil<br>6) clear liquid phase, yellow oil on bottom |
| propyl gallate | 1:1 | 1) mill 4a w/toluene at 30 Hz for 3 × 10-min. cycles<br>2) dry under $N_2$ 1 day | Obs | 1) sticky goo<br>2) white sticky goo |
| propyl gallate | 1:1 | 1) add EtOH to 4a w/stirring at ~75° C.<br>2) SC, ~75° C. to RT, stand at RT 4 days<br>3) freezer, 2 days<br>4) partial SE<br>5) freezer (capped), 3 days<br>6) SE<br>7) add MTBE w/stirring<br>8) stir, RT, 30 days<br>9) SE | Obs | 1) clear soln.<br>2) clear soln.<br>3) clear soln.<br>4) clear soln.<br>5) clear soln.<br>6) sticky goo<br>7) clear soln.<br>8) clear soln.<br>9) sticky amber oil |
| pyrazine | 1:5<br><br><br><br>1:10<br><br>1:20 | 1) dissolve pyrazine in acetone, add to 4a<br>2) RC (stir), RT, 3 days<br>3) add 5 mol. eq. pyrazine<br>4) RC (stir), RT, 4 days<br>5) add 10 mol. eq. pyrazine<br>6) RC (stir), RT, 46 days | Obs | 1) clear soln.<br>2) clear yellow soln.<br>3) clear soln.<br>4) clear soln.<br>5) clear light yellow soln.<br>6) clear soln. |
| pyrazine | 1:2 | 1) add EtOH to 4a w/stirring at ~75° C.<br>2) SC, ~75° C. to RT, stand at RT 4 days | Obs | 1) clear soln.<br>2) clear soln.<br>3) clear soln.<br>4) clear soln. |

TABLE 1-continued

| Coformer | 4a/Coformer Molar Ratio | Conditions | Technique | Results |
|---|---|---|---|---|
| | | 3) freezer, 2 days<br>4) partial SE<br>5) freezer (capped), 3 days<br>6) SE<br>7) add heptane w/stirring<br>8) stir, RT, 30 days | | 5) clear soln.<br>6) sticky goo<br>7) clear liquid phase, light yellow goo<br>8) clear liquid phase, oil on bottom |
| L-pyroglutamic acid | 1:1 | 1) mill 4a w/MeOH at 30 Hz for 3 × 10-min. cycles<br>2) dry under $N_2$ 1 day | Obs | 1) sticky goo<br>2) sticky goo |
| L-pyroglutamic acid | 1:2 | 1) add EtOH to 4a w/stirring at ~75° C.<br>2) SC, ~75° C. to RT, stand at RT 4 days<br>3) freezer, 2 days<br>4) partial SE<br>5) freezer (capped), 3 days<br>6) SE<br>7) add diethyl ether w/ stirring<br>8) stir, RT, 5 days<br>9) decant liquid phase, dry solids under $N_2$ | Obs<br><br><br><br><br><br><br><br><br>OM<br>XRPD | 1) clear soln.<br>2) clear soln.<br>3) clear soln.<br>4) clear soln.<br>5) clear soln.<br>6) sticky goo<br>7) clear liquid phase, white goo<br>8) clear liquid phase, white solids<br>9) white solids<br>fines and aggregates, B/E<br>Pyroglutamic Material A + pyroglutamic acid |
| L-pyroglutamic acid | 1:1 | 1) add EtOH to 4a and acid solids w/sonication<br>2) partial FE, 1 day<br>3) evaporate under stream of $N_2$<br>4) add diethyl ether w/ stirring<br>5) add seeds$^a$, stir, RT, 10 days<br>6) vac. filter | Obs<br><br><br><br><br><br>OM<br>XRPD | 1) clear soln.<br>2) small amt. clear soln.<br>3) clear viscous oil<br>4) oil became white<br>5) clear liquid phase, white solids present<br>6) white solids<br>fines and aggregates, B/E<br>Pyroglutamic Material B + pyroglutamic acid |
| L-pyroglutamic acid | 1:1 | 1) add EtOH to 4a and acid solids w/sonication<br>2) alternatively add seeds$^a$ and aliquots diethyl ether multiple times w/stirring to ether/EtOH 6:1 ratio<br>3) stir, RT, 1 day<br>4) stir, 2-8° C., 11 days<br>5) SE<br>6) scrape solids down to oil, add diethyl ether w/ stirring<br>7) stir, RT, 1 day<br>8) decant liquid, dry solids briefly under $N_2$ | Obs/OM<br><br><br><br><br><br><br><br><br><br><br><br>OM (after step 8)<br>XRPD | 1) clear soln.<br>2) seeds always dissolved, always clear soln.<br>3) clear soln.<br>4) clear soln.<br>5) sticky oil, small amt. solids on upper walls (irregular plates, B/E)<br>6) clear soln., oil on bottom<br>7) clear liquid phase, off-white solids<br>8) off-white solids<br><br>fines and aggregates, B/E<br><br>Pyroglutamic Material A + Material B + acid |
| L-pyroglutamic acid | 2:1 | 1) add EtOH to 4a and acid solids w/sonication<br>2) filter<br>3) evaporate under $N_2$ stream<br>4) add seeds$^b$<br>5) add diethyl ether w/ stirring<br>6) stir, RT, 18 days<br>7) vac. filter | Obs<br><br><br><br><br><br><br>OM<br>XRPD | 1) clear soln., few floats<br>2) clear soln.<br>3) clear viscous oil<br>4) seeds remained<br>5) oil turned white, clear liquid phase<br>6) clear liquid phase, white solids<br>7) white solids<br>fines and aggregates, B/E<br>Pyroglutamic Material B + pyroglutamic acid |
| 2,3,5,6-tetramethyl-pyrazine (TMP) | 1:10<br><br><br><br>1:20 | 1) add EtOAc to 4a and coformer solids w/ sonication<br>2) RC (stir), RT, 2 days<br>3) add 10 mol eq. TMP<br>4) RC (stir), RT, 36 days | Obs | 1) clear soln.<br>2) clear soln.<br>3) undissolved solids present<br>4) clear soln. |
| L-tryptophan | 1:2 | 1) add EtOH to 4a and coformer solids w/stirring at ~73° C.<br>2) add water to EtOH/water 3:1<br>3) SC, ~73° C. to RT, stir at RT 1 day<br>4) vac. filter | Obs<br><br><br><br><br><br><br>OM<br>XRPD | 1) undissolved solids present<br>2) clear soln.<br>3) clear liquid phase, white solids<br>4) shiny white solids (like a pearl)<br><br>aggregates, B/E<br>L-tryptophan |

TABLE 1-continued

| Coformer | 4a/Coformer Molar Ratio | Conditions | Technique | Results |
|---|---|---|---|---|
| urea | 1:2 | 1) add EtOH to 4a and urea solids w/stirring at ~74° C.<br>2) SC, ~74° C. to RT, stir at RT 1 day<br>3) freezer, 3 days<br>4) add EtOAc w/stirring (EtOAc/EtOH 6:1)<br>5) stir, RT, 1 day<br>6) freezer, 7 days<br>7) decant liquid phase, dry solids briefly under $N_2$ | Obs<br><br><br><br><br><br><br><br><br><br>OM<br>XRPD | 1) clear soln.<br>2) clear soln.<br>3) slightly hazy suspension<br>4) slightly hazy suspension<br>5) clear liquid phase, small amt. solids<br>6) clear liquid phase, small amt. white solids<br>7) white solids<br><br>needles, B/E<br>urea |

[a,b]Various batches of seeds of uncharacterized crystalline material comprising 4a and pyroglutamic acid.

Example 4

Preparation and Characterization of 4a/L-Proline Form B

Equimolar amounts of amorphous 4a and L-proline (1:1) were mixed in methanol and were heated to about 68° C. The resulting solution was allowed to slowly cool to room temperature, at which point a white suspension had formed. The suspension was then stirred at room temperature for three days, after which Form B as a white solid was collected by filtration and dried.

Alternatively, amorphous 4a and L-proline in a 1:2 molar ratio were combined in ethanol and heated to about 82° C. to yield a white suspension. The suspension was held at 82° C. for about 5 minutes, allowed to slowly cool to room temperature, and then stirred at room temperature for three days. Form B was collected as a white solid by filtration and dried.

Form B is an anhydrous 1:2 4a/L-proline co-crystal. Form B was characterized by XRPD (with indexing), DSC, TGA, DVS, Raman spectroscopy, IR spectroscopy, proton NMR, HPLC and elemental analysis.

The XRPD pattern for Form B was successfully indexed (Table 2) and it indicated that Form B consists primarily or exclusively of a single crystalline phase (FIG. 1). The unit cell volume obtained from the indexing solution is consistent with an anhydrous 1:2 4a/L-proline co-crystal. Table 3 below presents unit cell parameters.

TABLE 2

Observed peaks for 4a/L-proline Form B

| °2θ | d space (Å) | Intensity (%) |
|---|---|---|
| 5.81 ± 0.20 | 15.204 ± 0.523 | 36 |
| 8.40 ± 0.20 | 10.512 ± 0.250 | 21 |
| 8.50 ± 0.20 | 10.396 ± 0.244 | 16 |
| 10.46 ± 0.20 | 8.454 ± 0.161 | 29 |
| 11.65 ± 0.20 | 7.590 ± 0.130 | 15 |
| 12.14 ± 0.20 | 7.286 ± 0.120 | 30 |
| 14.57 ± 0.20 | 6.076 ± 0.083 | 43 |
| 14.76 ± 0.20 | 5.998 ± 0.081 | 71 |
| 16.49 ± 0.20 | 5.371 ± 0.065 | 11 |
| 16.86 ± 0.20 | 5.253 ± 0.062 | 100 |
| 17.51 ± 0.20 | 5.061 ± 0.057 | 78 |
| 18.16 ± 0.20 | 4.881 ± 0.053 | 21 |
| 18.39 ± 0.20 | 4.819 ± 0.052 | 25 |
| 18.89 ± 0.20 | 4.694 ± 0.049 | 52 |
| 19.00 ± 0.20 | 4.667 ± 0.049 | 70 |
| 19.17 ± 0.20 | 4.627 ± 0.048 | 30 |
| 19.41 ± 0.20 | 4.570 ± 0.047 | 61 |
| 19.58 ± 0.20 | 4.530 ± 0.046 | 27 |
| 19.93 ± 0.20 | 4.452 ± 0.044 | 14 |
| 21.05 ± 0.20 | 4.217 ± 0.040 | 47 |
| 21.48 ± 0.20 | 4.134 ± 0.038 | 10 |
| 21.82 ± 0.20 | 4.070 ± 0.037 | 34 |
| 23.43 ± 0.20 | 3.794 ± 0.032 | 19 |
| 23.56 ± 0.20 | 3.774 ± 0.032 | 29 |
| 23.77 ± 0.20 | 3.740 ± 0.031 | 24 |
| 24.36 ± 0.20 | 3.651 ± 0.030 | 44 |
| 25.13 ± 0.20 | 3.541 ± 0.028 | 17 |
| 25.71 ± 0.20 | 3.462 ± 0.026 | 10 |
| 26.36 ± 0.20 | 3.378 ± 0.025 | 21 |
| 26.60 ± 0.20 | 3.348 ± 0.025 | 16 |
| 26.94 ± 0.20 | 3.306 ± 0.024 | 14 |
| 27.18 ± 0.20 | 3.278 ± 0.024 | 9 |
| 27.48 ± 0.20 | 3.243 ± 0.023 | 9 |
| 27.67 ± 0.20 | 3.221 ± 0.023 | 14 |
| 27.97 ± 0.20 | 3.188 ± 0.022 | 13 |
| 28.28 ± 0.20 | 3.153 ± 0.022 | 9 |
| 28.91 ± 0.20 | 3.086 ± 0.021 | 19 |
| 29.38 ± 0.20 | 3.037 ± 0.020 | 12 |
| 29.75 ± 0.20 | 3.001 ± 0.020 | 10 |
| 29.99 ± 0.20 | 2.977 ± 0.019 | 8 |

TABLE 3

Unit Cell Parameters for 4a/L-proline Form B

| Bravais Type | Primitive Monoclinic |
|---|---|
| a [Å] | 11.130 |
| b [Å] | 10.168 |
| c [Å] | 16.094 |
| α [deg] | 90 |
| β [deg] | 109.27 |
| γ [deg] | 90 |
| Volume [Å$^3$/cell] | 1,719.3 |
| Chiral Contents? | Chiral |
| Extinction Symbol | P 1 2$_1$ 1 |
| Space Group(s) | P2$_1$ (4) |

A sample of Form B isolated from a MeOH slurry was characterized by proton NMR and HPLC. The proton NMR data indicate a 1:2 4a/L-proline stoichiometry with no residual solvent detected. The purity of 4a in the sample was 99.7% as determined by HPLC.

Figure 2:
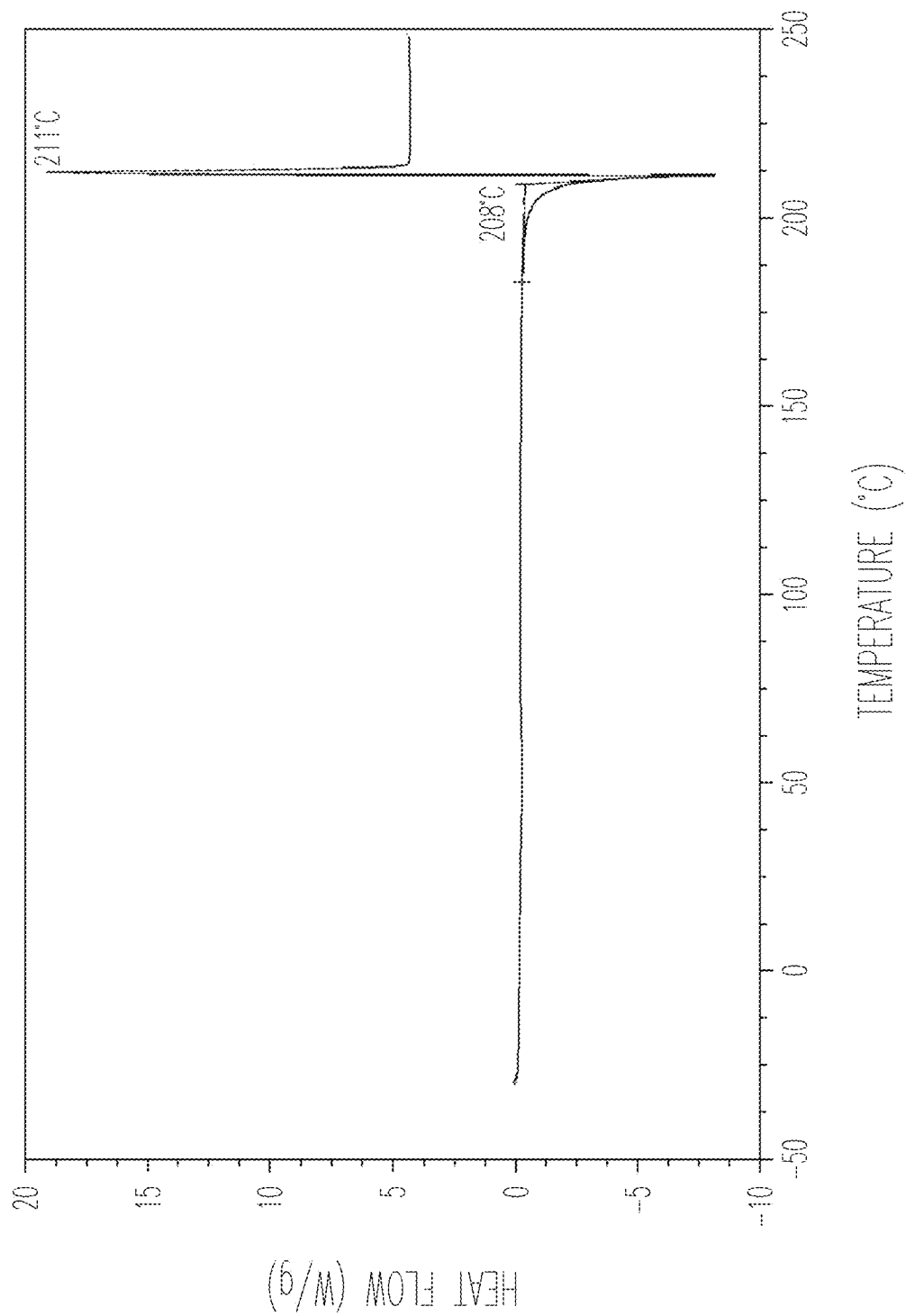
FIG. 2 is a differential scanning calorimetry (DSC) curve of Form B.
Figure 3:
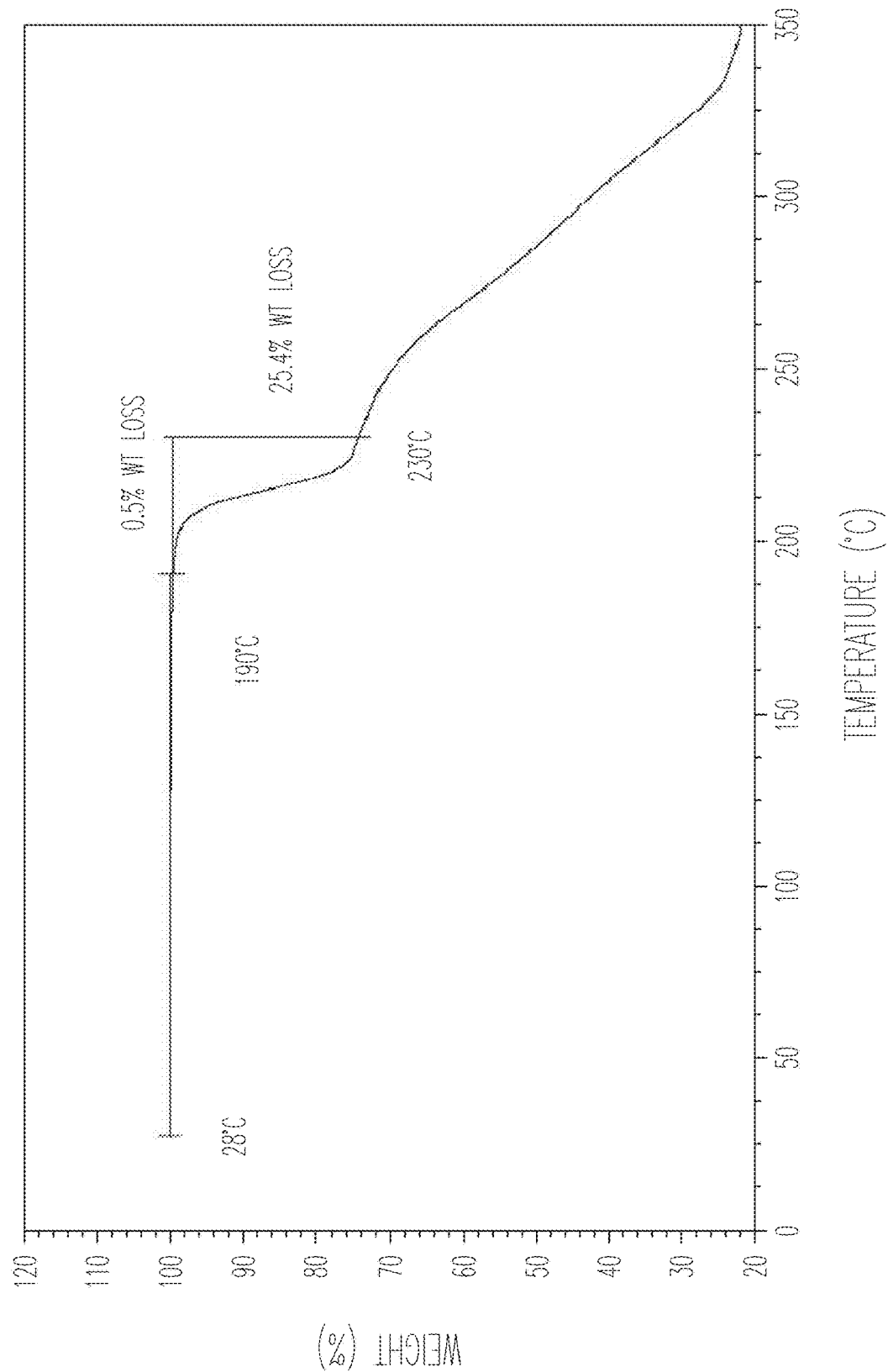
FIG. 3 is a thermal gravimetric analysis (TGA) curve of Form B.

DSC and TGA thermograms for Form B are presented in FIG. 2 and FIG. 3, respectively. The data are plotted separately since different samples were analyzed for each technique. The sample analyzed by TGA was isolated from a MeOH slurry, while the DSC sample resulted from a co-crystal formation experiment in MeOH. Virtually no weight loss is observed by TGA between ambient temperature and 190° C., consistent with an anhydrous/non-solvated material. The DSC is consistent with this as well, showing no notable thermal events until the onset of an endothermic event at 208° C., with an overlapping strong exothermic event. To be noted, the sample was observed to come out of the pan following this analysis, likely contributing to the magnitude of the exotherm. These events likely correspond with the melting/dissociation of the co-crystal. Similarly, a steep decrease in the TGA thermogram above 190° C. is likely attributed to volatilization of a portion of the L-proline component of the co-crystal, followed by likely decomposition.

To further confirm the co-crystal stoichiometry, Form B was analyzed by C, H, N, F, and O elemental analyses (Table 4). Comparison of the experimental percent composition values to theoretical values for a 1:1 and 1:2 co-crystal show that the sample is more closely consistent with a 1:2 co-crystal. This result is consistent with the other characterization data.

TABLE 4

Elemental Analysis of 4a/L-proline Form B

| Theoretical 1:1 co-crystal | Theoretical 1:2 co-crystal | Experimental Results |
|---|---|---|
| 61.9% C | 60.3% C | 59.78% C |
| 7.0% H | 7.1% H | 6.88% H |
| 5.0% N | 6.2% N | 6.28% N |
| 3.4% F | 2.8% F | 2.79% F |
| 22.7% O | 23.6% O | 25.12% O |

Figure 4:
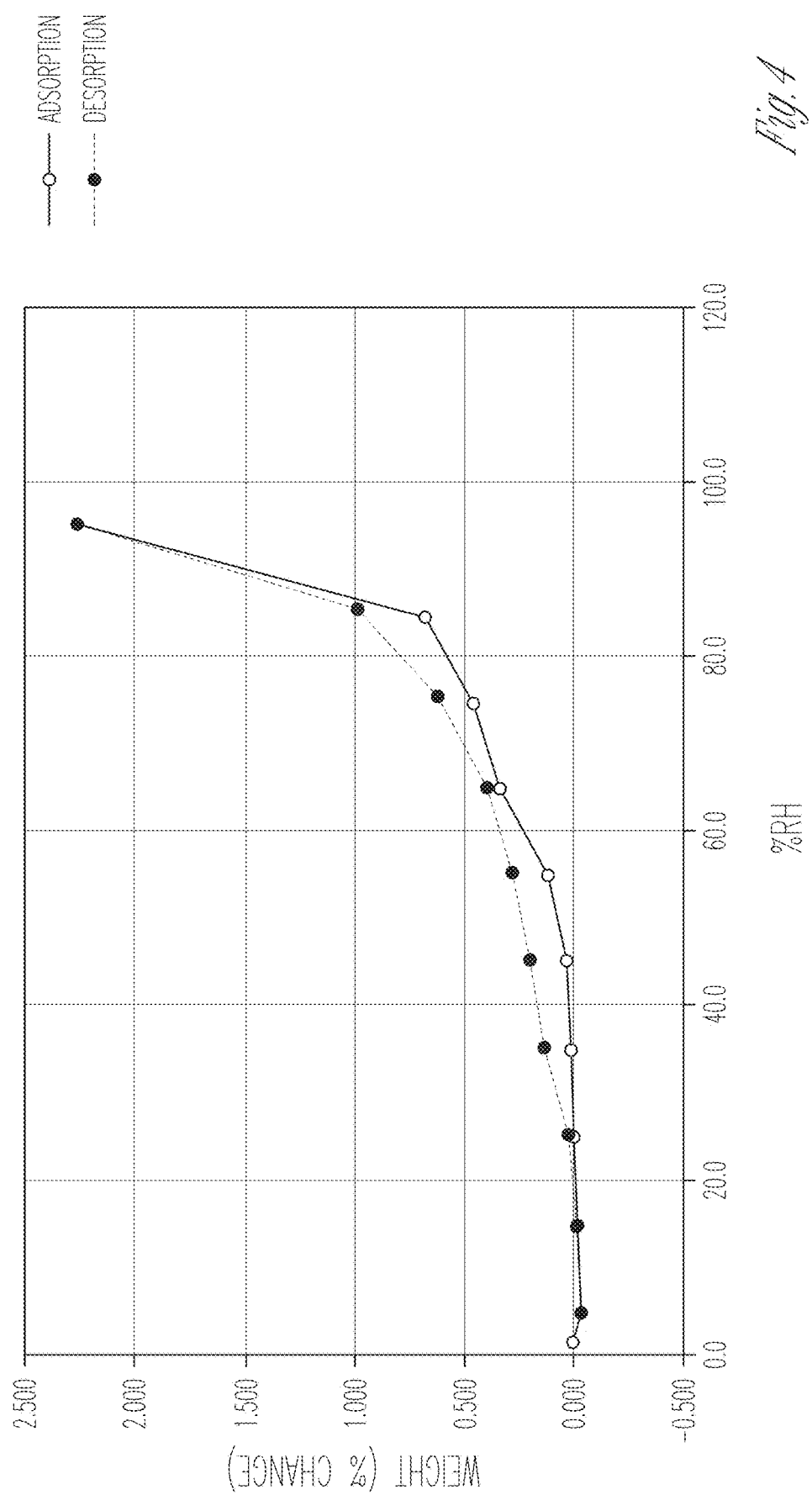
FIG. 4 is a dynamic vapor sorption (DVS) curve of Form B.

A dynamic vapor sorption (DVS) isotherm for Form B is shown in FIG. 4. Weight gain of 2.3 wt % was noted between 5% and 95% RH, with the majority of the sorption occurring above 50% RH. All of this weight was lost on desorption with minor hysteresis noted. The vapor sorption kinetic equilibration timed out on the sorption step between 85%-95% RH, indicating that the co-crystal could potentially pick up more moisture than what was measured if it was allowed a longer equilibration time. Analysis of the post-DVS material by XRPD showed no observable change in form.

Figure 5:
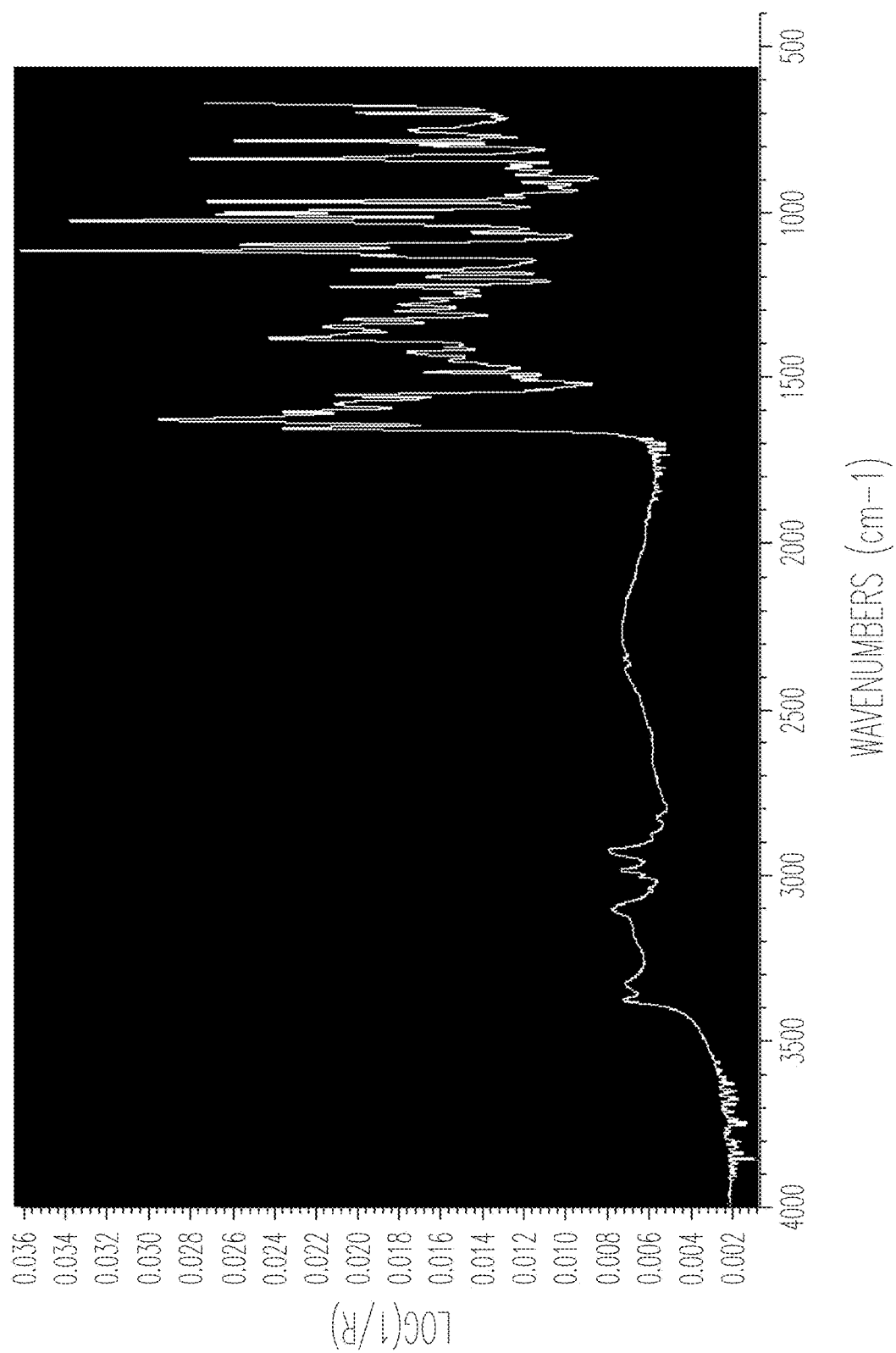
FIG. 5 is an infrared (IR) spectrum of Form B.
Figure 6:
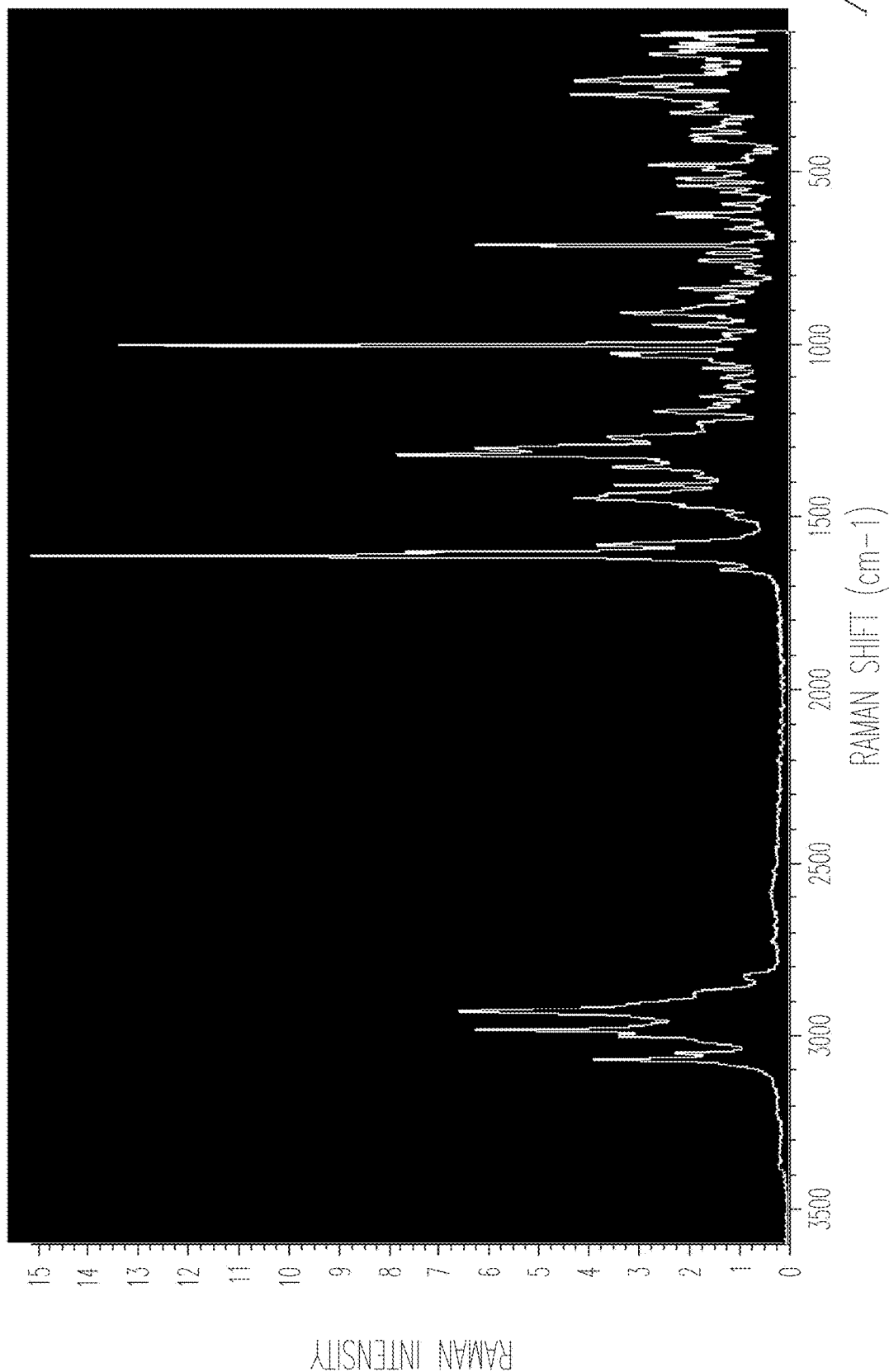
FIG. 6 is a Raman spectrum of Form B.

IR and Raman spectra were acquired for Form B and are presented in FIG. 5 and FIG. 6, respectively.

Example 5

Single Crystal X-Ray Structure Determination of 4a/L-Proline Form B

Data Collection

A colorless plate of 4a/L-proline Form B ($C_{34}H_{48}FN_3O_{10}$ [$C_{24}H_{30}FNO_6$, $2(C_5H_9NO_2)$]) having approximate dimensions of 0.70×0.45×0.30 mm, was mounted on a nylon loop in random orientation. Preliminary examination and data collection were performed with Cu Kα radiation (λ=1.54178 Å) on a Rigaku Rapid II diffractometer equipped with confocal optics. Refinements were performed using SHELX2013 (Sheldrick, G. M. *Acta Cryst.*, 2008, A64, 112).

Cell constants and an orientation matrix for data collection were obtained from least-squares refinement using the setting angles of 21646 reflections in the range 4°<θ<68°. The refined mosaicity from DENZO/SCALEPACK was 0.44° indicating good crystal quality (Otwinowski, Z.; Minor, W. *Methods Enzymol.* 1997, 276, 307). The space group was determined by the program XPREP (Bruker, XPREP in SHELXTL v. 6.12., Bruker AXS Inc., Madison, Wis., USA, 2002). From the systematic presence of the following conditions: 0k0 k=2n, and from subsequent least-squares refinement, the space group was determined to be $P2_1$ (no. 4).

The data were collected to a maximum diffraction angle (2θ) of 135.73°, at room temperature.

Data Reduction

Frames were integrated with HKL3000 (Otwinowski (1997)). A total of 21646 reflections were collected, of which 5936 were unique. Lorentz and polarization corrections were applied to the data. The linear absorption coefficient is 0.833 mm$^{-1}$ for Cu Kα radiation. An empirical absorption correction using SCALEPACK (Otwinowski (1997)) was applied. Transmission coefficients ranged from 0.128 to 0.779. A secondary extinction correction was applied (Sheldrick (2008)). The final coefficient, refined in least-squares, was 0.0157(11) (in absolute units). Intensities of equivalent reflections were averaged. The agreement factor for the averaging was 4.1% based on intensity.

Structure Solution and Refinement

The structure was solved by direct methods using SHELXT (Sheldrick (2008)). The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.0640P)^2+(0.5095P)]$, where $P=(F_o^2+2F_c^2)/3$.

Scattering factors were taken from the "International Tables for Crystallography" (International Tables for Crystallography, Vol. C, Kluwer Academic Publishers: Dordrecht, The Netherlands, 1992, Tables 4.2.6.8 and 6.1.1.4). Of the 5936 reflections used in the refinements, only the reflections with $F_o^2>2\sigma(F_o^2)$ were used in calculating the fit residual, R. A total of 5601 reflections were used in the calculation. The final cycle of refinement included 490 variable parameters and converged (largest parameter shift was <0.01 times its estimated standard deviation) with unweighted and weighted agreement factors of:

$$R = \sum |F_o - F_c| / \sum F_o = 0.0422$$

$$R_w = \sqrt{(\sum w(F_o^2 - F_c^2)^2 / \sum w(F_o^2)^2)} = 0.1141$$

The standard deviation of an observation of unit weight (goodness of fit) was 1.062. The highest peak in the final difference Fourier had a height of 0.187 e/Å$^3$. The minimum negative peak had a height of −0.193 e/Å$^3$.

Calculated X-Ray Powder Diffraction (XRPD) Pattern

A calculated XRPD pattern was generated for Cu radiation using Mercury (Macrae, C. F. Edgington, P. R. McCabe, P. Pidcock, E. Shields, G. P. Taylor, R. Towler M. and van de Streek, J.; *J. Appl. Cryst.*, 2006, 39, 453-457) and the atomic coordinates, space group, and unit cell parameters from the single crystal structure.

Atomic Displacement Ellipsoid and Packing Diagrams

The atomic displacement ellipsoid diagram was prepared using Mercury (Macrae (2006)). Atoms are represented by 50% probability anisotropic thermal ellipsoids. Packing diagrams and additional figures were generated with Mercury (Macrae (2006)). Hydrogen bonding is represented as dashed lines. Assessment of chiral centers was performed with PLATON (Spek, A. L. *PLATON. Molecular Graphics Program.* Utrecht University, Utrecht, The Netherlands, 2008. Spek, A. L, *J. Appl. Cryst.* 2003, 36, 7). Absolute configuration is evaluated using the specification of molecular chirality rules (Cahn, R. S.; Ingold, C; Prelog, V. Angew. *Chem. Intern. Ed. Eng.,* 1966, 5, 385; Prelog, V., Helmchen, G. *Angew. Chem. Intern. Ed. Eng.,* 1982, 21, 567).

Results

The monoclinic cell parameters and calculated volume are: a=11.1270(4) Å, b=10.1566(4) Å, c=16.0790(6) Å, $\beta$=109.309(2)° ($\alpha$=$\gamma$=90°), V=1714.91(11) Å$^3$. The formula weight of the asymmetric unit in the crystal structure of Form B is 677.75 g mol$^{-1}$ with Z=2, resulting in a calculated density of 1.313 g cm$^3$. The space group was determined to be P2$_1$ (no. 4). A summary of the crystal data and crystallographic data collection parameters are provided in Table 5.

TABLE 5

Crystal Data and Data Collection Parameters for 4a/L-proline Form B

| | |
|---|---|
| formula | C$_{34}$H$_{48}$FN$_3$O$_{10}$ |
| formula weight | 677.77 |
| space group | P2$_1$ (No. 4) |
| a, Å | 11.1270(4) |
| b, Å | 10.1566(4) |
| c, Å | 16.0790(6) |
| b, deg | 109.309(2) |
| V, Å$^3$ | 1714.91(11) |
| Z | 2 |
| d$_{calc}$, g cm$^{-3}$ | 1.312 |
| crystal dimensions, mm | 0.25 × 0.20 × 0.16 |
| temperature, K | 295 |
| radiation (wavelength, Å) | Cu K$_\alpha$ (1.54178) |
| monochromator | confocal optics |
| linear abs coef, mm$^{-1}$ | 0.833 |
| absorption correction applied | empirical[a] |
| transmission factors: min, max | 0.128, 0.779 |
| diffractometer | Rigaku RAPID-II |
| h, k, l range | −13 to 13 −12 to 12 −18 to 18 |
| 2q range, deg | 8.42-135.73 |
| mosaicity, deg | 0.44 |
| programs used | SHELXTL |
| F$_{000}$ | 724 |
| data collected | 21646 |
| unique data | 5936 |
| R$_{int}$ | 0.041 |
| data used in refinement | 5936 |
| cutoff used in R-factor calculations | F$_o^2$ > 2.0 s(F$_o^2$) |
| data with I > 2.0 s(I) | 5601 |
| refined extinction coef | 0.0157 |
| number of variables | 490 |
| largest shift/esd in final cycle | 0 |
| R(F$_o$) | 0.0422 |
| R$_w$(F$_o^2$) | 0.1141 |
| goodness of fit | 1.062 |
| absolute structure determination | Flack parameter[b] (−0.02(11)) Hooft parameter[c] (−0.02(5)) Friedel Coverage 92% |

[a]Otwinowski, Z.; Minor, W. Methods Enzymol. 1997, 276, 307.
[b]Flack, H. D. Acta Cryst., 1983 A39, 876.
[c]Hooft, R. W. W., Straver, L. H., and Spek, A. L. J. Appl. Cryst., 2008, 41, 96-103.

The space group and unit cell parameters are consistent with those obtained from XRPD analysis of Form B (see Table 3 above).

The quality of the structure obtained is high, as indicated by the fit residual, R of 0.0422 (4.22%). R-values in the range of 0.02 to 0.06 are quoted for the most reliably determined structures (Glusker, Jenny Pickworth; Trueblood, Kenneth N. *Crystal Structure Analysis: A Primer,* 2$^{nd}$ ed.; Oxford University press: New York, 1985; p. 87).

Figure 7:
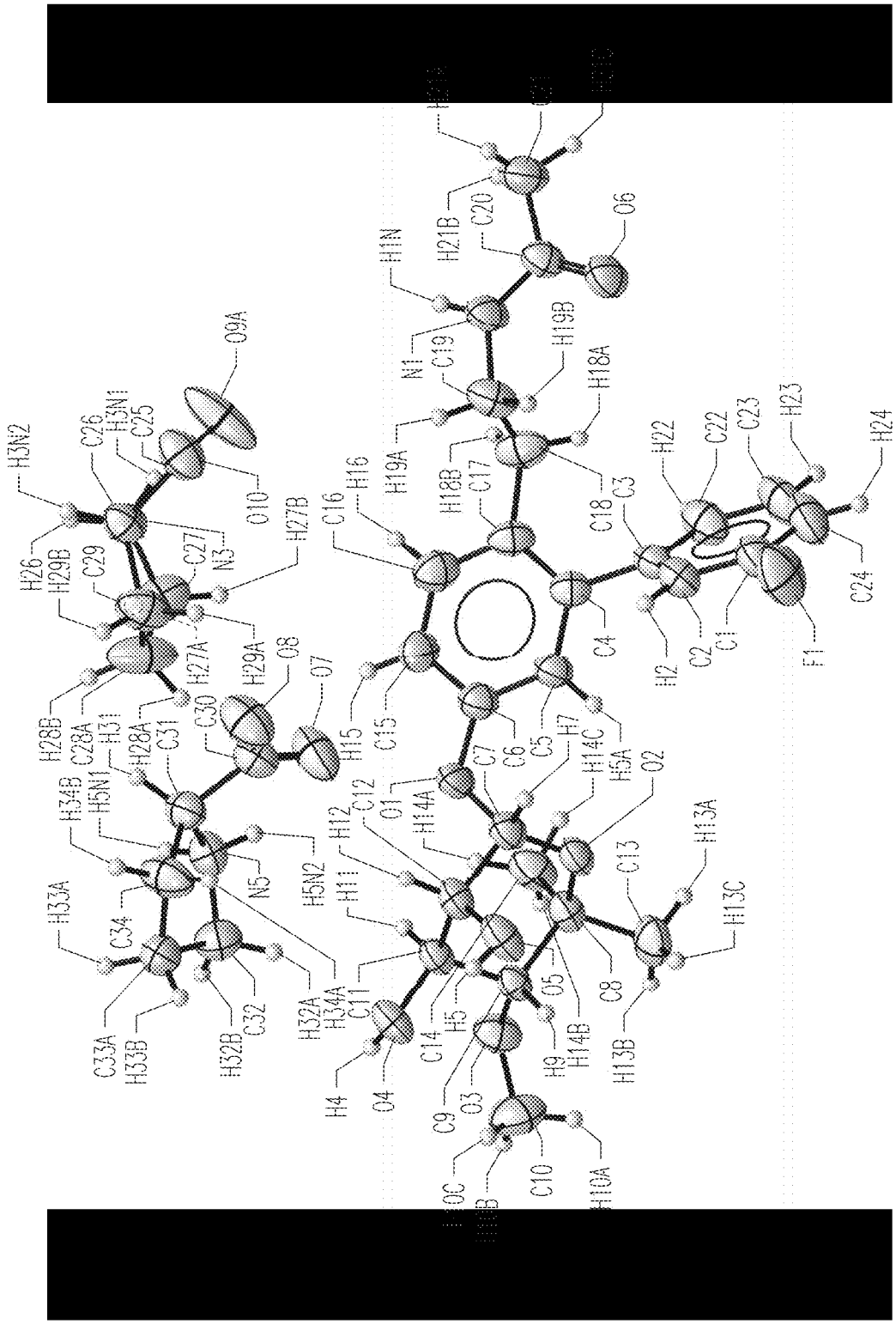
FIG. 7 is an atomic displacement ellipsoid drawing of Form B determined by single crystal X-ray crystallography.

An atomic displacement ellipsoid drawing of Form B is shown in FIG. 7. The molecule observed in the asymmetric unit of the single crystal structure is consistent with the proposed molecular structure of 4a. The asymmetric unit shown in FIG. 7 contains one 4a molecule and two L-proline molecules, consistent with a 1:2 4a: L-proline stoichiometry. Two protons were located and refined independently on both of the proline nitrogen atoms, indicating zwitterions. Both of the L-proline molecules are disordered over two positions, refining to 82/18% and 71/29% occupancies.

The absolute structure can be determined through an analysis of anomalous X-ray scattering by the crystal. A refined parameter x, known as the Flack parameter (Flack, H. D.; Bernardinelli, G., *Acta Cryst.* 1999, A55, 908; Flack, H. D.; Bernardinelli, G., *J. Appl. Cryst.* 2000, 33, 1143; Flack, H. D. *Acta Cryst.* 1983, A39, 876; Parsons, S., Flack, H. D., Wagner, T., *Acta Cryst.* 2013, B69, 249-259), encodes the relative abundance of the two components in an inversion twin. The structure contains a fraction 1-x of the model being refined, and x of its inverse. Provided that a low standard uncertainty is obtained, the Flack parameter should be close to 0 if the solved structure is correct, and close to 1 if the inverse model is correct. The measured Flack parameter for the structure of Form B shown in FIG. 7 is −0.02 with a standard uncertainty of 0.11, which indicates weak inversion-distinguishing power, and therefore no interpretation of the Flack parameter could be made. The error in the standard uncertainty prevents an assignment based solely on the Flack factor.

Refinement of the Flack parameter (x) does not result in a quantitative statement about the absolute structure assignment. However, an approach applying Bayesian statistics to Bijvoet differences can provide a series of probabilities for different hypotheses of the absolute structure (Hooft, R. W. W., Straver, L. H., and Spek, A. L. *J. Appl. Cryst.,* 2008, 41, 96-103; Bijvoet, J. M.; Peerdeman, A. F.; van Bommel A. J. *Nature* 1951, 168, 271). This analysis provides a Flack equivalent (Hooft) parameter in addition to probabilities that the absolute structure is either correct, incorrect or a racemic twin. For the current data set the Flack equivalent (Hooft) parameter was determined to be −0.02(5), the probability that the structure is correct is 1.000, the probability that the structure is incorrect is 0.9×10$^{-91}$ and the probability that the material is a racemic twin is 0.2×10$^{-24}$. Therefore, the absolute configuration of the model in FIG. 7 is correct. This structure contains four chiral centers on 4a located at C7, C9, C11, and C12 (FIG. 7) which bond in the R,R,S, and R configuration, respectively, and one chiral center on each of the proline molecules at C26 and C31 both bonding in the S configuration.

Figure 8:
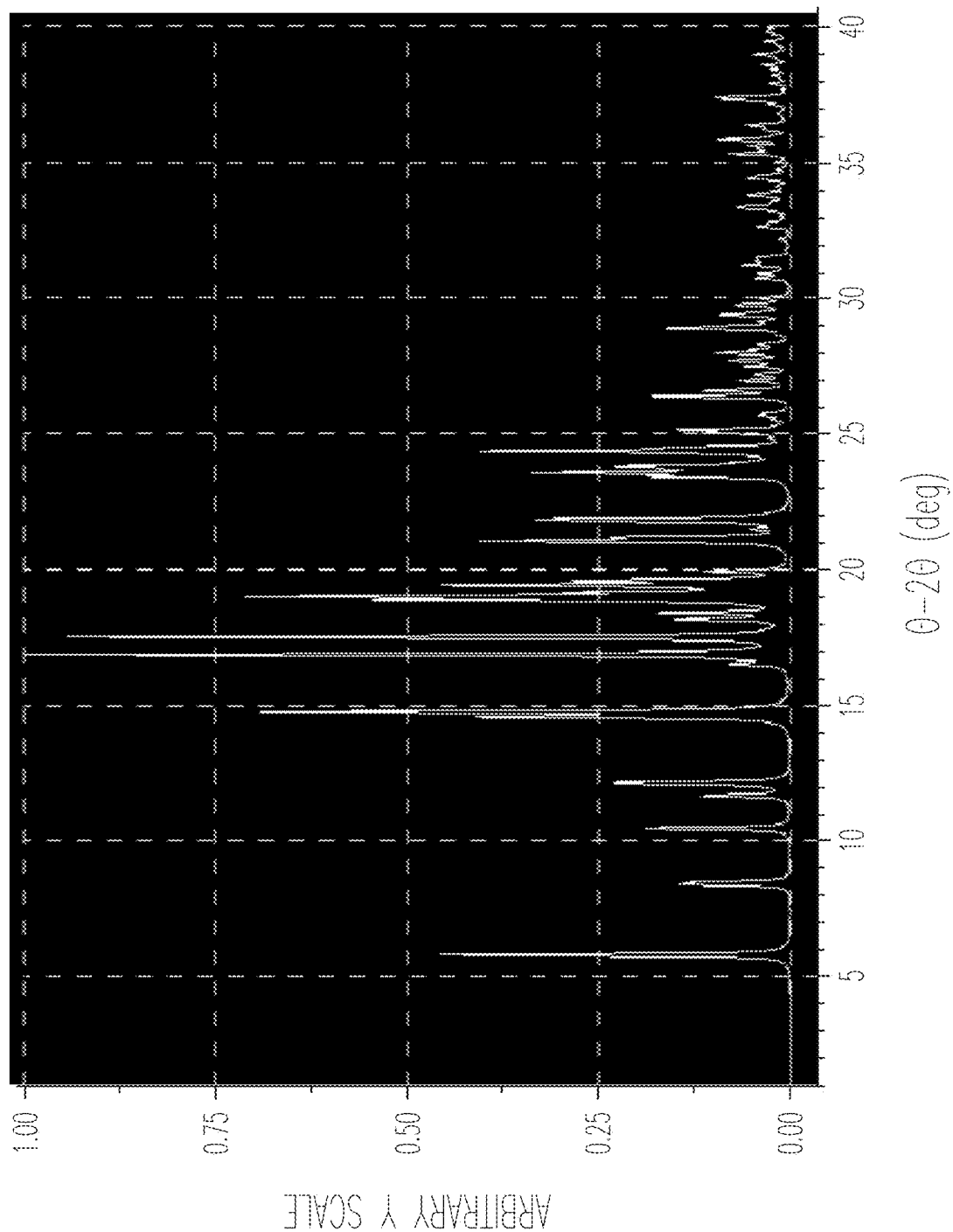
FIG. 8 is a calculated XRPD pattern of Form B based upon single crystal structure determination.
Figure 9:
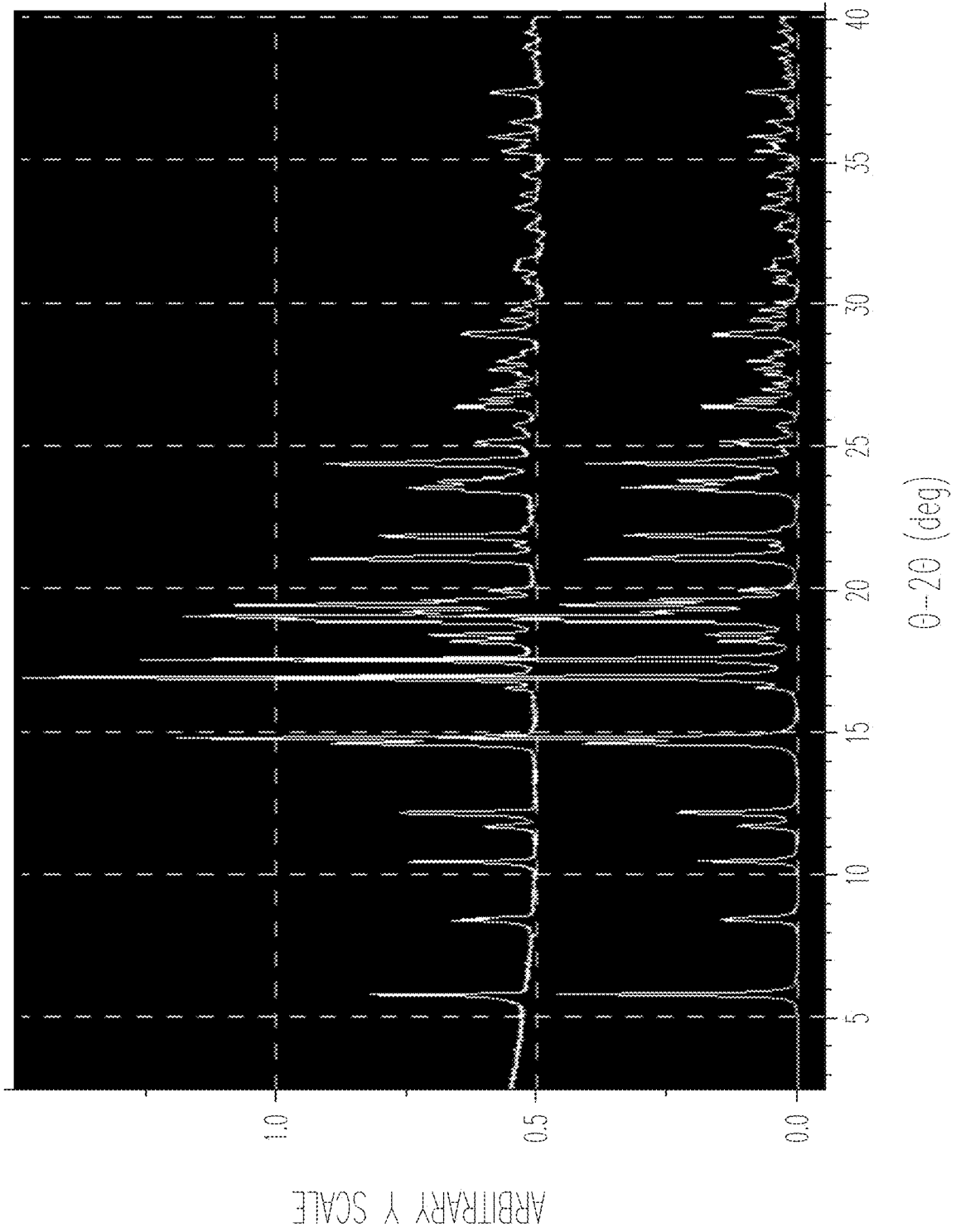
FIG. 9 shows a comparison of the calculated XRPD pattern of Form B (bottom trace) to the experimental XRPD pattern of Form B (top trace).

FIG. 8 shows a calculated XRPD pattern of Form B, generated from the single crystal structure. The previously indexed experimental XRPD pattern of Form B (Example 4) is shown above and is consistent with the calculated XRPD pattern (FIG. 9).

Example 6

Preparation and Characterization of 4a/L-Proline Form C

Equimolar amounts of amorphous 4a and L-proline (1:1) were slurried and then stirred in acetone at room temperature for 3 days. The slurry was filtered to collect Form C as a white solid.

Form C also was prepared by dissolving equimolar amounts of amorphous 4a and L-proline in EtOH. Acetone then was introduced to the solution by vapor diffusion (VD) to precipitate Form C.

The data indicated that Form C consists of a 1:1 co-crystal with 1 mole of acetone present in the crystal lattice, although the acetone does not participate in hydrogen bonding. The single crystal data provides confirmation of chemical and solid phase compositions.

An XRPD pattern for Form C (FIG. 10) was successfully indexed, and observed peaks are shown in Table 6.

TABLE 6

Observed peaks for 4a/L-proline Form C

| °2θ | d space (Å) | Intensity (%) |
|---|---|---|
| 8.73 ± 0.20 | 10.126 ± 0.232 | 67 |
| 10.51 ± 0.20 | 8.414 ± 0.160 | 46 |
| 11.83 ± 0.20 | 7.477 ± 0.126 | 32 |
| 12.10 ± 0.20 | 7.308 ± 0.120 | 62 |
| 12.26 ± 0.20 | 7.214 ± 0.117 | 36 |
| 12.44 ± 0.20 | 7.110 ± 0.114 | 31 |
| 14.64 ± 0.20 | 6.047 ± 0.082 | 97 |
| 15.14 ± 0.20 | 5.847 ± 0.077 | 50 |
| 16.13 ± 0.20 | 5.492 ± 0.068 | 13 |
| 17.53 ± 0.20 | 5.055 ± 0.057 | 100 |
| 18.26 ± 0.20 | 4.855 ± 0.053 | 62 |
| 18.91 ± 0.20 | 4.688 ± 0.049 | 71 |
| 19.36 ± 0.20 | 4.580 ± 0.047 | 74 |
| 19.56 ± 0.20 | 4.536 ± 0.046 | 56 |
| 20.17 ± 0.20 | 4.399 ± 0.043 | 20 |
| 20.97 ± 0.20 | 4.232 ± 0.040 | 24 |
| 21.15 ± 0.20 | 4.197 ± 0.039 | 22 |
| 21.33 ± 0.20 | 4.163 ± 0.039 | 54 |
| 21.55 ± 0.20 | 4.121 ± 0.038 | 29 |
| 22.40 ± 0.20 | 3.966 ± 0.035 | 14 |
| 23.18 ± 0.20 | 3.834 ± 0.033 | 29 |
| 23.71 ± 0.20 | 3.750 ± 0.031 | 20 |
| 24.02 ± 0.20 | 3.701 ± 0.030 | 33 |
| 24.34 ± 0.20 | 3.654 ± 0.030 | 25 |
| 24.73 ± 0.20 | 3.597 ± 0.029 | 40 |
| 25.87 ± 0.20 | 3.441 ± 0.026 | 23 |
| 26.54 ± 0.20 | 3.356 ± 0.025 | 17 |
| 26.71 ± 0.20 | 3.335 ± 0.025 | 15 |
| 27.09 ± 0.20 | 3.289 ± 0.024 | 12 |
| 27.38 ± 0.20 | 3.254 ± 0.023 | 16 |
| 27.86 ± 0.20 | 3.200 ± 0.023 | 8 |
| 28.40 ± 0.20 | 3.140 ± 0.022 | 12 |
| 28.73 ± 0.20 | 3.105 ± 0.021 | 11 |
| 29.05 ± 0.20 | 3.071 ± 0.021 | 10 |
| 29.45 ± 0.20 | 3.031 ± 0.020 | 23 |

Unit cell parameters from XRPD indexing are presented in Table 7 below:

TABLE 7

Unit Cell Parameters for 4a/L-proline Form C

| Bravais Type | Primitive Monoclinic |
|---|---|
| a [Å] | 10.992 |
| b [Å] | 10.275 |
| c [Å] | 15.362 |
| α [deg] | 90 |
| β [deg] | 108.07 |
| γ [deg] | 90 |
| Volume [Å³/cell] | 1,649.5 |
| Chiral Contents? | Chiral |
| Extinction Symbol | P 1 2₁ 1 |
| Space Group(s) | P2₁ (4) |

Figure 11:
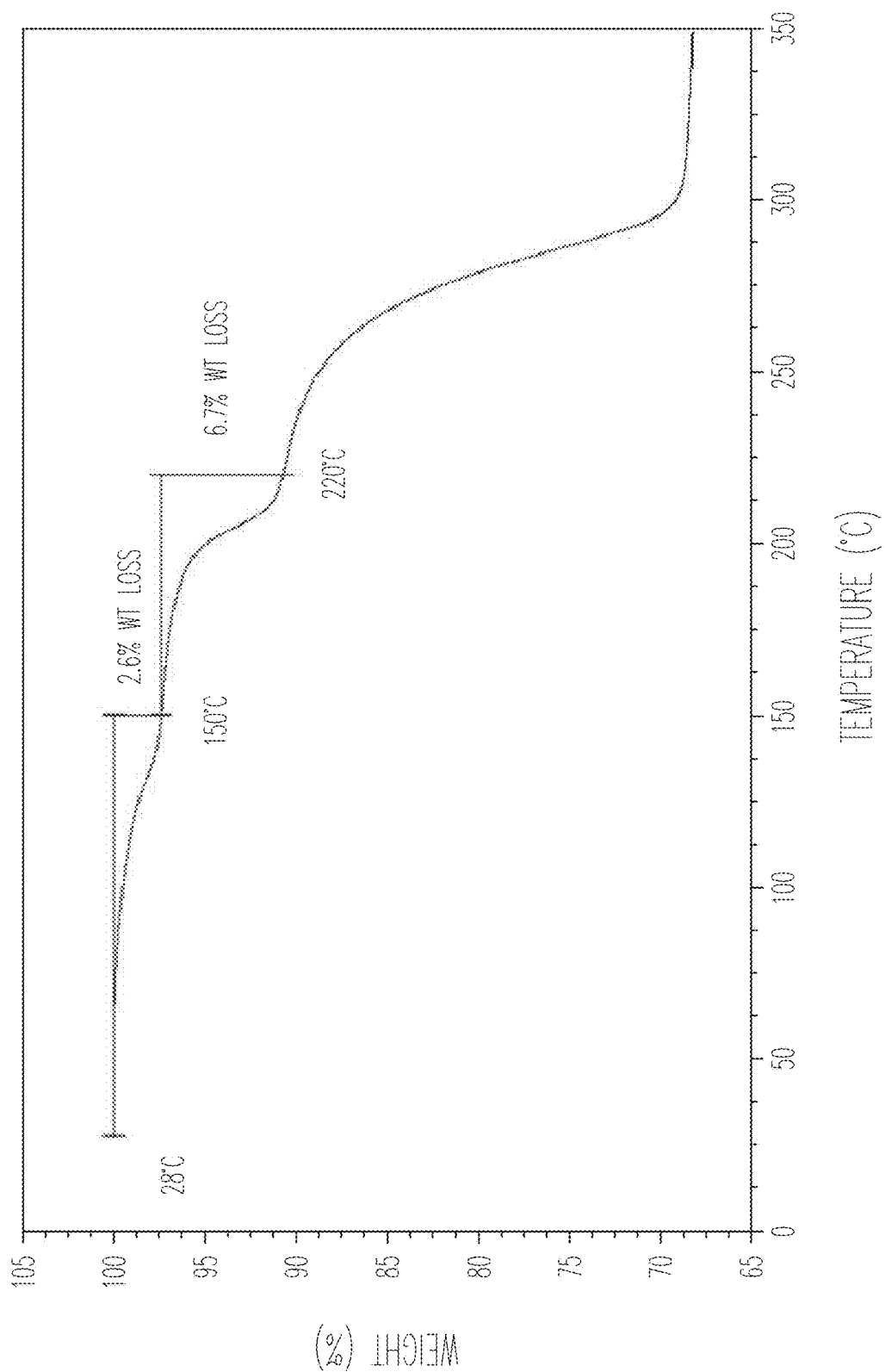
FIG. 11 is a thermal gravimetric analysis (TGA) curve of Form C.

A TGA thermogram for Form C exhibits stepwise weight loss, consistent with the finding that the material consists of an acetone solvate (FIG. 11). The acetone appears to volatilize in two separate steps. In the first step, 2.6% weight loss is observed between ~60 and 150° C. On the assumption that the volatile is acetone, the 2.6 wt % corresponds with 0.26 mole (or ~¼ of the total acetone per the single crystal structure). A second weight loss step between 150 and 220° C. corresponds with 6.7% weight loss, or 0.70 mol if acetone is assumed to be the only volatile.

Example 7

Single Crystal X-Ray Structure Determination of 4a/L-Proline Form C

A colorless plate of $C_{32}H_{45}FN_2O_9$ [$C_{24}H_{30}FNO_6$, $C_5H_9NO_2$, $C_3H_6O$] having approximate dimensions of 0.19×0.18×0.10 mm, was mounted on a fiber in random orientation. Preliminary examination and data collection were performed with Cu K$_α$ radiation (λ=1.54178 Å) on a Rigaku Rapid II diffractometer equipped with confocal optics. Refinements were performed using SHELX2013 (Sheldrick (2008)).

Cell constants and an orientation matrix for data collection were obtained from least-squares refinement using the setting angles of 12615 reflections in the range 4°<θ<59°. The refined mosaicity from DENZO/SCALEPACK was 0.25° indicating good crystal quality (Otwinowski (1997)). The space group was determined by the program XPREP (Bruker (2002)). From the systematic presence of the following conditions: 0k0 k=2n, and from subsequent least-squares refinement, the space group was determined to be P2₁ (no. 4).

The data were collected to a maximum diffraction angle (2θ) of 117.84° at room temperature.

Frames were integrated with HKL3000 (Bruker (2002)). A total of 12615 reflections were collected, of which 4368 were unique. Lorentz and polarization corrections were applied to the data. The linear absorption coefficient is 0.788 mm$^{-1}$ for Cu Kα radiation. An empirical absorption correction using SCALEPACK (Bruker (2002)) was applied. Transmission coefficients ranged from 0.060 to 0.924. A secondary extinction correction was applied (Sheldrick (2008)). The final coefficient, refined in least-squares, was 0.0049(7) (in absolute units). Intensities of equivalent reflections were averaged. The agreement factor for the averaging was 4.8% based on intensity.

Structure solution and refinement were performed in a manner analogous to Example 5 above. Of the 4368 reflections used in the refinements, only the reflections with $F_o^2 > 2σ(F_o^2)$ were used in calculating the fit residual, R. A total of 3518 reflections were used in the calculation. The final cycle of refinement included 417 variable parameters and converged (largest parameter shift was <0.01 times its estimated standard deviation) with unweighted and weighted agreement factors of:

$$R = \sum |F_o - F_c| / \sum F_o = 0.0535$$

$$R_w = \sqrt{(\sum w(F_o^2 - F_c^2)^2 / \sum w(F_o^2)^2)} = 0.1305$$

The standard deviation of an observation of unit weight (goodness of fit) was 1.078. The highest peak in the final difference Fourier had a height of 0.271 e/Å³. The minimum negative peak had a height of −0.167 e/Å³.

A calculated XRPD pattern and atomic displacement ellipsoid diagram were generated according to the procedure in Example 5.

The monoclinic cell parameters and calculated volume are: a=10.9962(6) Å, b=10.2721(6) Å, c=15.3197(9) Å, β=107.937(4)° (α=γ=90°), V=1646.32(17) Å$^3$. The formula weight of the asymmetric unit in the crystal structure of Form C is 620.70 g mol$^{-1}$ with Z=2, resulting in a calculated density of 1.252 g cm$^{-3}$. The space group was determined to be P2$_1$ (no. 4). A summary of the crystal data and crystallographic data collection parameters are provided in Table 8. The space group and unit cell parameters are in agreement with those obtained previously by XRPD indexing (Example 6).

TABLE 8

Crystal Data and Data Collection Parameters for 4a/L-proline Form C

| | |
|---|---|
| formula | C$_{32}$H$_{45}$FN$_2$O$_9$ |
| formula weight | 620.72 |
| space group | P2$_1$ (No. 4) |
| a, Å | 10.9962(6) |
| b, Å | 10.2721(6) |
| c, Å | 15.3197(9) |
| b, deg | 107.937(4) |
| V, Å$^3$ | 1646.32(16) |
| Z | 2 |
| d$_{calc}$, g cm$^{-3}$ | 1.252 |
| crystal dimensions, mm | 0.19 × 0.18 × 0.15 |
| temperature, K | 293 |
| radiation (wavelength, Å) | Cu K$_\alpha$ (1.54178) |
| monochromator | confocal optics |
| linear abs coef, mm$^{-1}$ | 0.788 |
| absorption correction applied | empirical$^a$ |
| transmission factors: min, max | 0.79, 0.89 |
| diffractometer | Rigaku RAPID-II |
| h, k, l range | −12 to 12 −11 to 11 −17 to 17 |
| 2q range, deg | 6.06-126.82 |
| mosaicity, deg | 0.25 |
| programs used | SHELXTL |
| F$_{000}$ | 664 |
| data collected | 12615 |
| unique data | 4368 |
| R$_{int}$ | 0.048 |
| data used in refinement | 4368 |
| cutoff used in R-factor calculations | F$_o^2$ > 2.0 s(F$_o^2$) |
| data with I > 2.0 s(I) | 3518 |
| refined extinction coef | 0.0049 |
| number of variables | 417 |
| largest shift/esd in final cycle | 0 |
| R(F$_o$) | 0.054 |
| R$_w$(F$_o^2$) | 0.131 |
| goodness of fit | 1.078 |
| absolute structure determination | Flack parameter$^b$ (0.08(14)) Hooft parameter$^c$ (0.09(9)) Friedel Coverage 86% |

$^a$Otwinowski (1997).
$^b$Flack (1983).
$^c$Hooft (2008).

Figure 12:
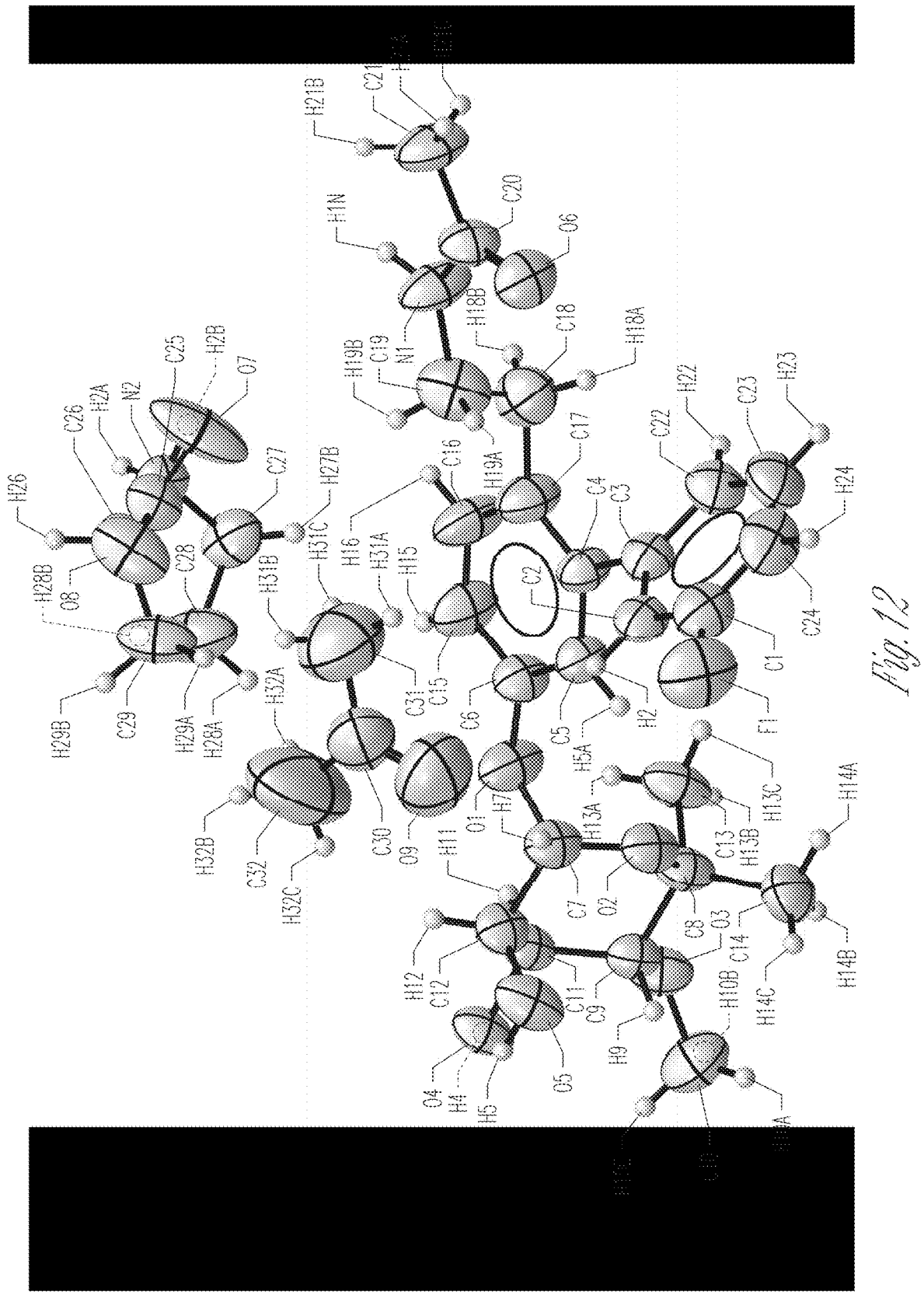
FIG. 12 is an atomic displacement ellipsoid drawing of Form C determined by single crystal X-ray crystallography.

An atomic displacement ellipsoid drawing of Form C is shown in FIG. 12. The molecule observed in the asymmetric unit of the single crystal structure is consistent with the proposed molecular structure of 4a/L-proline. The asymmetric unit shown in FIG. 12 contains one 4a molecule, one L-proline molecule, and one acetone molecule. Two protons were located and refined independently on the proline nitrogen atom, indicating a zwitterion.

Figure 10:
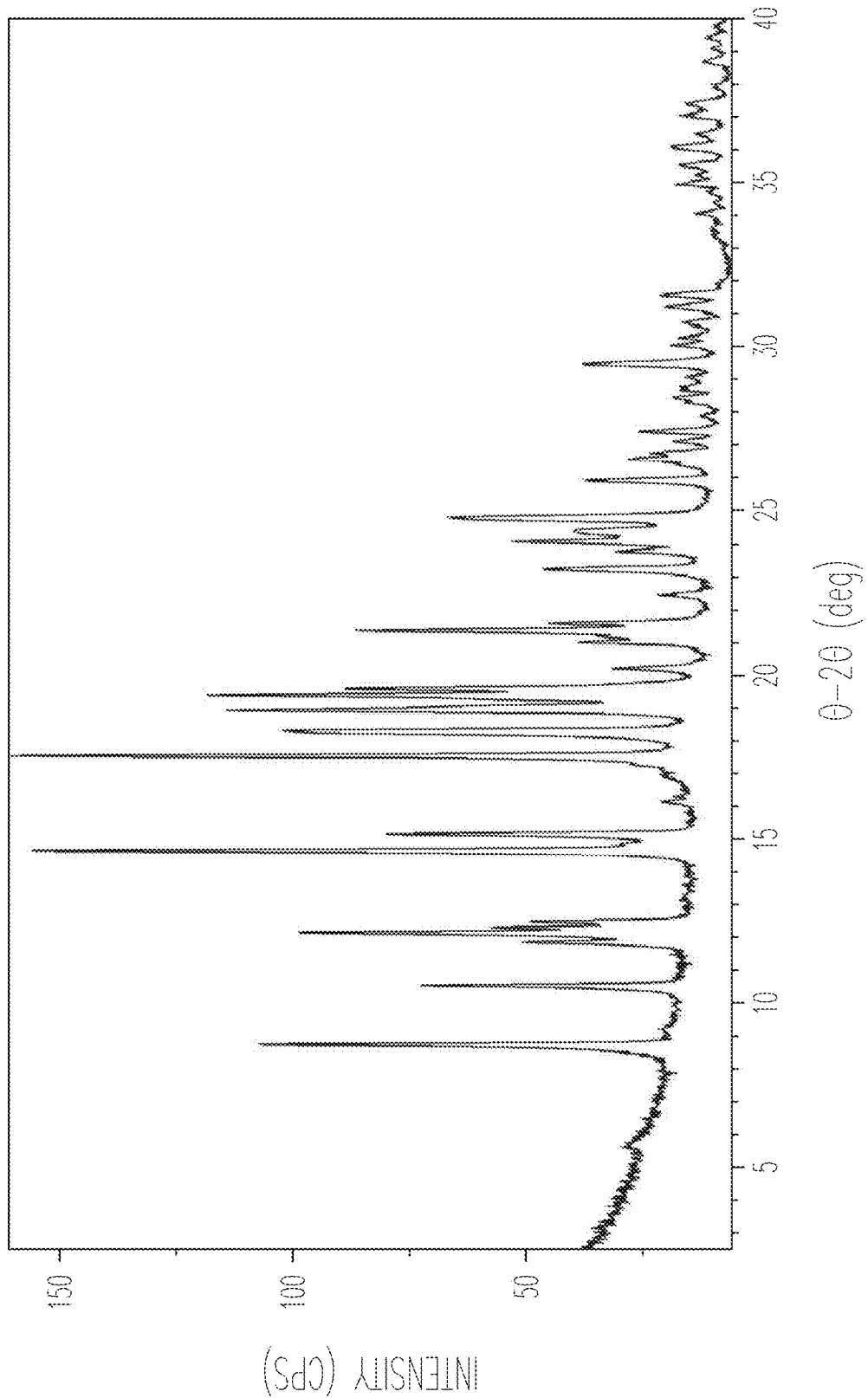
FIG. 10 presents an X-ray powder diffraction (XRPD) pattern of Form C.
Figure 13:
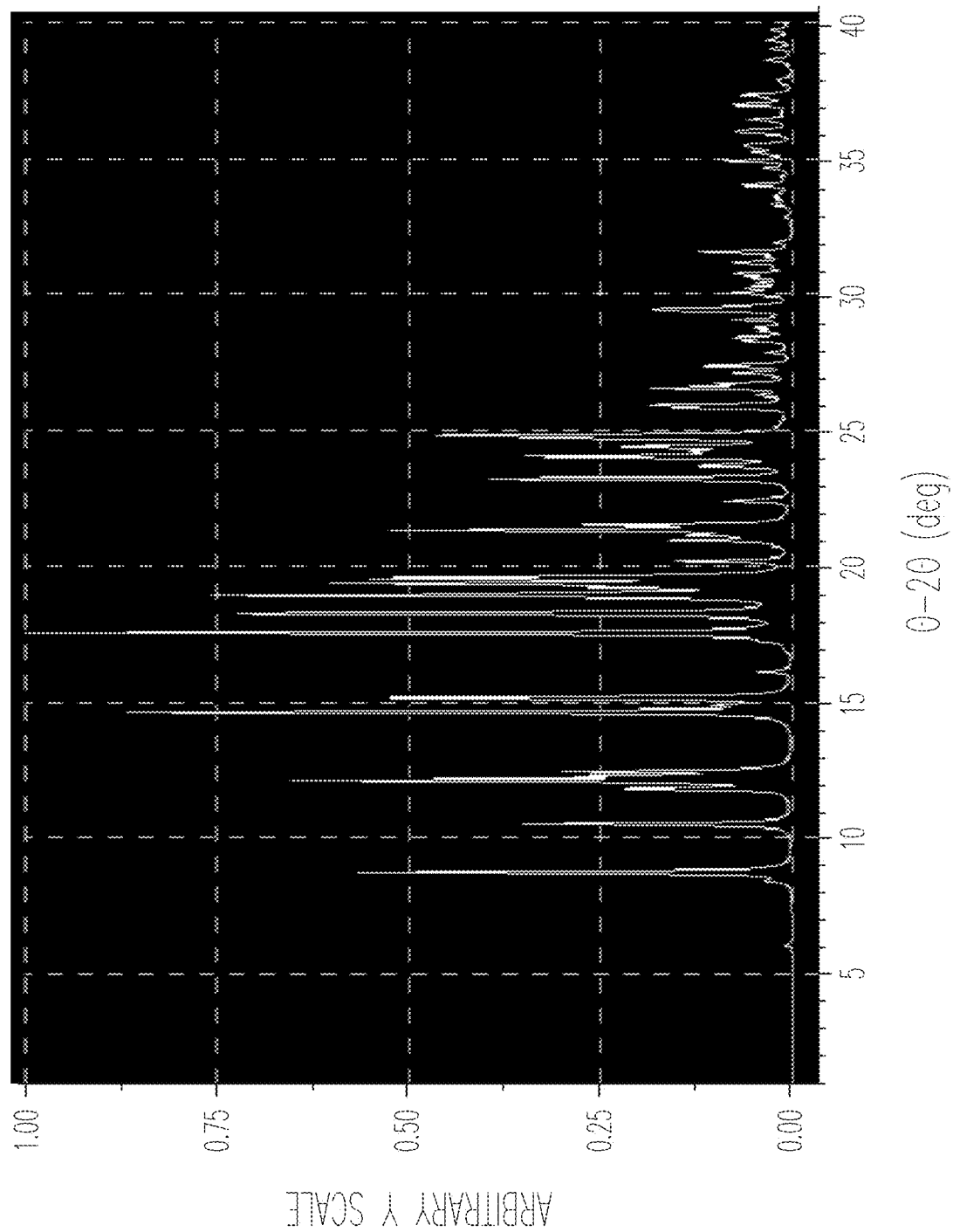
FIG. 13 is a calculated XRPD pattern of Form C based upon single crystal structure determination.

FIG. 13 shows a calculated XRPD pattern of Form C, generated from the single crystal structure. The experimental XRPD pattern of the bulk material from which the crystal was obtained is shown in FIG. 10 as described above. All peaks in the experimental patterns are represented in the calculated XRPD pattern, indicating the bulk material is likely a single phase. Differences in intensities between the calculated and experimental powder diffraction patterns often are due to preferred orientation. Preferred orientation is the tendency for crystals to align themselves with some degree of order. This preferred orientation of the sample can significantly affect peak intensities, but not peak positions, in the experimental powder diffraction pattern.

For the current data set the Flack equivalent (Hooft) parameter was determined in the manner described in Example 5, and it was determined to be 0.09(9), the probability that the structure is correct is 1.000, the probability that the structure is incorrect is 0.4×10$^{-21}$ and the probability that the material is a racemic twin is 0.4×10$^{-4}$.

Therefore, the absolute configuration of the model in FIG. 12 is likely correct. This structure contains four chiral centers on 4a located at C7, C9, C11, and C12 (FIG. 12) which bond in the R, R, S, R configuration, respectively and one chiral center on the proline located at C26 which bonds in the S configuration.

Example 8

Preparation and Characterization of 4a/L-Proline Form D

Equimolar amounts of amorphous 4a and L-proline were combined in acetonitrile to give a thin suspension, which was then heated to about 85° C. The suspension was cooled to about 71° C., seeded with a small quantity of material prepared in Example 1, and held at about 71° C. to about 15 minutes. The suspension was then allowed to slowly cool to room temperature, and then stirred for three days. The resulting white suspension was filtered to yield Form D, which was then dried.

Form D was also prepared by combining equimolar amounts of amorphous 4a and L-proline in EtOH, heating to about 82° C. and held at that temperature for about 15 minutes, cooling to about 76° C., seeding with a small quantity of material prepared in Example 1, slowly cooling to temperature, and stirring for three days. The resulting off-white slurry was filtered, and the collected quantity of Form D was dried under vacuum at ~48° C.

Figure 14:
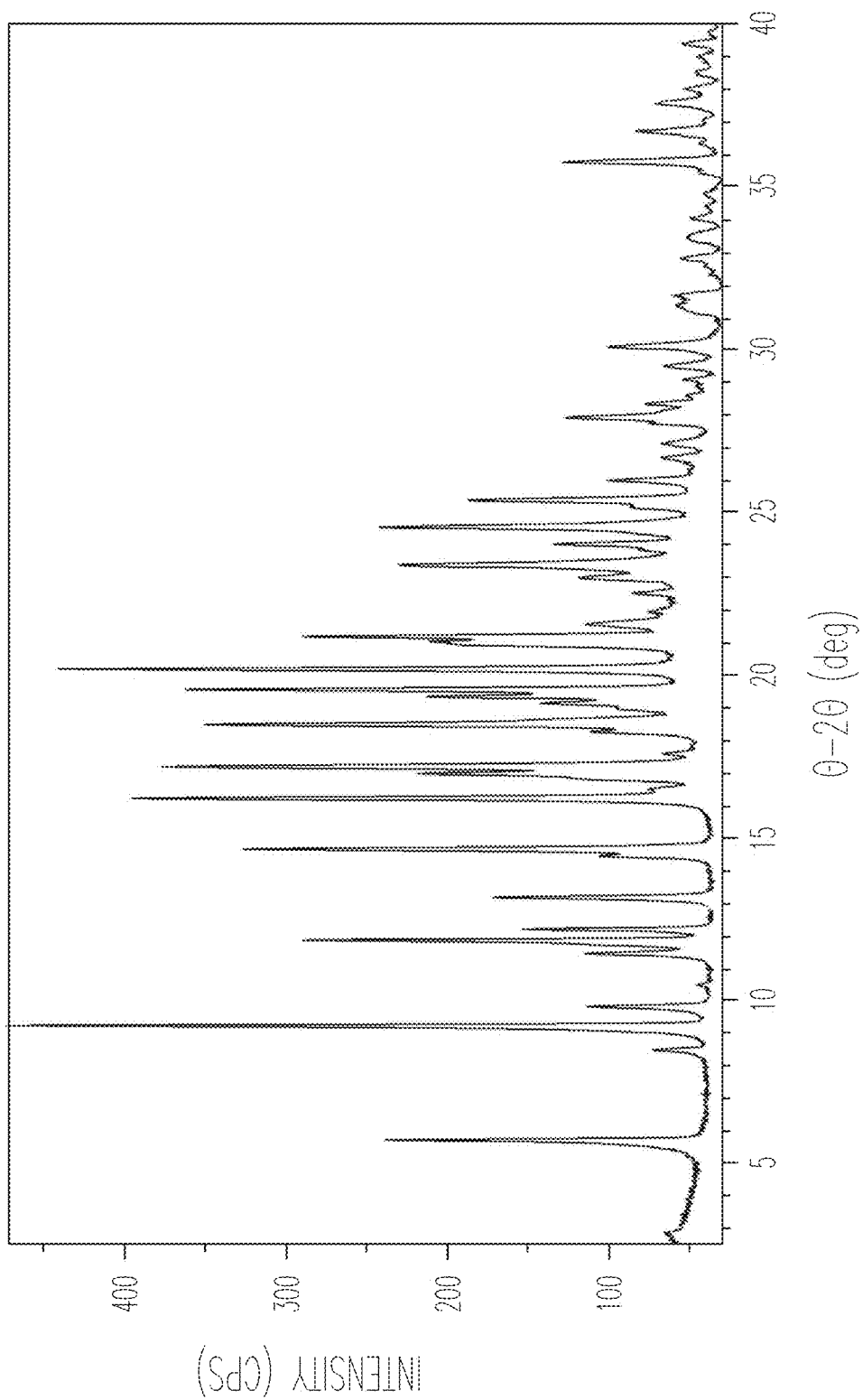
FIG. 14 presents an X-ray powder diffraction (XRPD) pattern of Form D.

Form D consists of an anhydrous/non-solvated 1:2 4a/L-proline co-crystal. An XRPD pattern for Form D was successfully indexed, indicating the material consists primarily or exclusively of a single crystalline phase (FIG. 14, Table 9). The unit cell volume (Table 10) obtained from the indexing solution is consistent with an anhydrous 1:2 4a/L-proline co-crystal.

TABLE 9

Observed peaks for 4a/L-proline Form D

| °2θ | d space (Å) | Intensity (%) |
|---|---|---|
| 2.82 ± 0.20 | 31.302 ± 2.219 | 13 |
| 5.68 ± 0.20 | 15.535 ± 0.546 | 50 |
| 8.45 ± 0.20 | 10.455 ± 0.247 | 16 |
| 9.20 ± 0.20 | 9.605 ± 0.208 | 100 |
| 9.78 ± 0.20 | 9.038 ± 0.184 | 24 |
| 10.46 ± 0.20 | 8.454 ± 0.161 | 10 |
| 11.42 ± 0.20 | 7.741 ± 0.135 | 25 |
| 11.83 ± 0.20 | 7.475 ± 0.126 | 62 |
| 12.17 ± 0.20 | 7.265 ± 0.119 | 33 |
| 13.15 ± 0.20 | 6.729 ± 0.102 | 37 |
| 14.42 ± 0.20 | 6.138 ± 0.085 | 23 |

TABLE 9-continued

Observed peaks for 4a/L-proline Form D

| °2θ | d space (Å) | Intensity (%) |
|---|---|---|
| 14.62 ± 0.20 | 6.054 ± 0.082 | 70 |
| 16.19 ± 0.20 | 5.470 ± 0.067 | 84 |
| 16.46 ± 0.20 | 5.382 ± 0.065 | 16 |
| 16.94 ± 0.20 | 5.231 ± 0.061 | 47 |
| 17.16 ± 0.20 | 5.163 ± 0.060 | 80 |
| 17.56 ± 0.20 | 5.047 ± 0.057 | 14 |
| 18.22 ± 0.20 | 4.864 ± 0.053 | 24 |
| 18.45 ± 0.20 | 4.804 ± 0.052 | 75 |
| 18.95 ± 0.20 | 4.680 ± 0.049 | 21 |
| 19.10 ± 0.20 | 4.643 ± 0.048 | 30 |
| 19.31 ± 0.20 | 4.593 ± 0.047 | 46 |
| 19.52 ± 0.20 | 4.544 ± 0.046 | 77 |
| 20.15 ± 0.20 | 4.403 ± 0.043 | 94 |
| 20.98 ± 0.20 | 4.230 ± 0.040 | 45 |
| 21.15 ± 0.20 | 4.196 ± 0.039 | 62 |
| 21.53 ± 0.20 | 4.124 ± 0.038 | 25 |
| 22.49 ± 0.20 | 3.951 ± 0.035 | 18 |
| 22.96 ± 0.20 | 3.870 ± 0.033 | 26 |
| 23.35 ± 0.20 | 3.807 ± 0.032 | 49 |
| 23.98 ± 0.20 | 3.707 ± 0.030 | 29 |
| 24.51 ± 0.20 | 3.629 ± 0.029 | 52 |
| 25.34 ± 0.20 | 3.512 ± 0.027 | 40 |
| 25.95 ± 0.20 | 3.431 ± 0.026 | 22 |
| 26.64 ± 0.20 | 3.343 ± 0.025 | 14 |
| 27.07 ± 0.20 | 3.291 ± 0.024 | 15 |
| 27.70 ± 0.20 | 3.218 ± 0.023 | 16 |
| 27.88 ± 0.20 | 3.198 ± 0.022 | 27 |
| 28.30 ± 0.20 | 3.151 ± 0.022 | 17 |
| 29.04 ± 0.20 | 3.072 ± 0.021 | 12 |
| 29.45 ± 0.20 | 3.030 ± 0.020 | 14 |

TABLE 10

Unit Cell Parameters for 4a/L-proline Form D

| Bravais Type | Primitive Orthorhombic |
|---|---|
| a [Å] | 10.092 |
| b [Å] | 11.112 |
| c [Å] | 30.974 |
| α [deg] | 90 |
| β [deg] | 90 |
| γ [deg] | 90 |
| Volume [Å³/cell] | 3,473.3 |
| Chiral Contents? | Chiral |
| Extinction Symbol | P 2₁ 2₁– |
| Space Group(s) | P2₁2₁ (18) |

Figure 15:
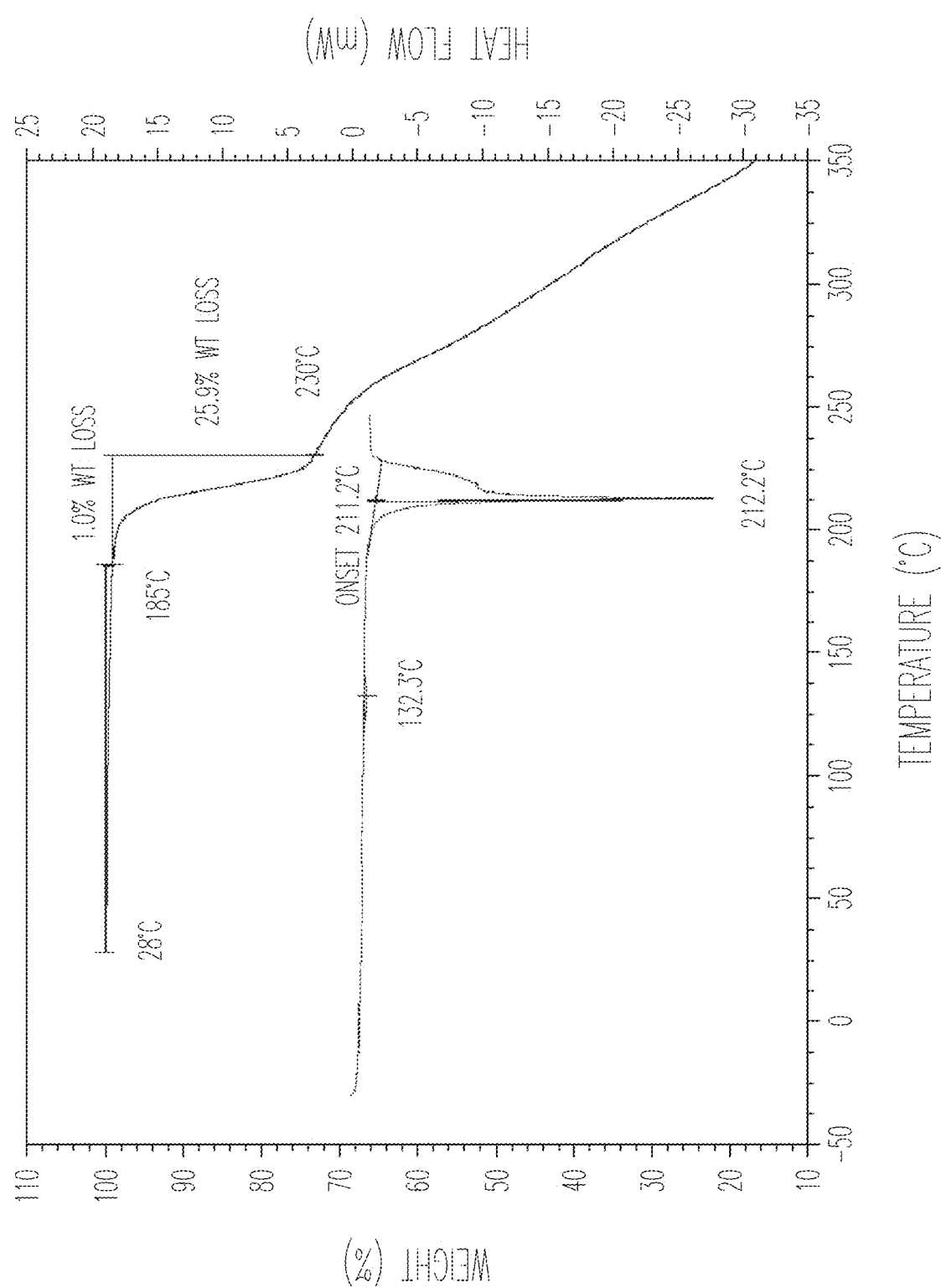
FIG. 15 shows DSC (bottom trace) and TGA (top trace) curves of Form D.

Form D was characterized by thermal techniques, proton NMR, HPLC, and DVS. An overlay of the DSC and TGA thermograms for the dried Form D is shown in FIG. 15. The insignificant weight loss by TGA up to 185° C. and lack of a broad desolvation endotherm by DSC are consistent with an anhydrous/non-solvated material. A small broad endotherm was observed at 132° C. (peak maximum). A sharp endotherm with onset at 211° C. corresponds with a steep stepwise weight loss of 26 wt % in the TGA thermogram, likely corresponding with simultaneous melting of the co-crystal and volatilization of L-proline.

Proton NMR data indicated a 1:2 4a/L-proline stoichiometry with 0.2 wt % residual EtOH detected. The purity of 4a in the sample was 99.6% by HPLC.

Figure 16:
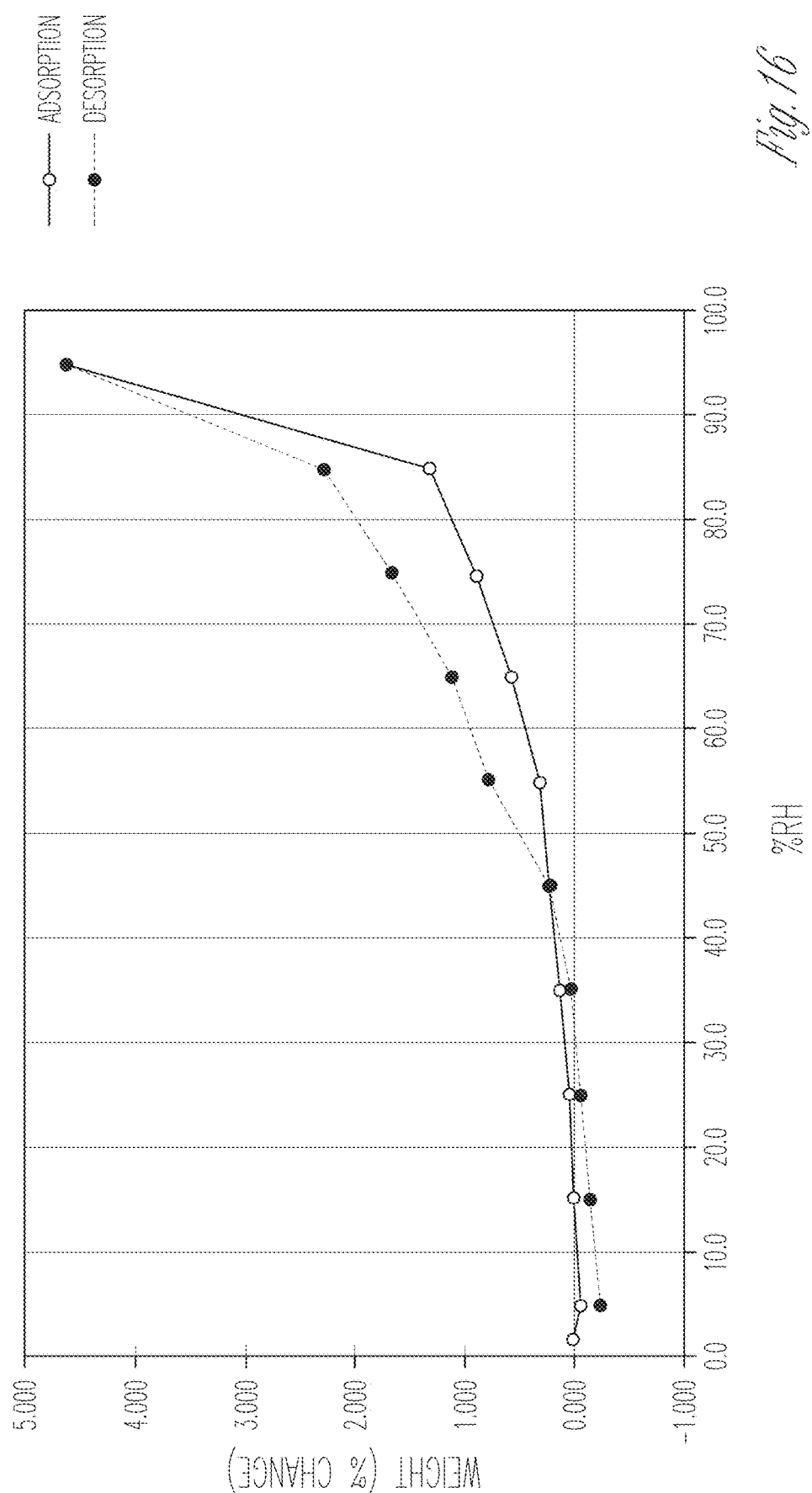
FIG. 16 is a dynamic vapor sorption (DVS) curve of Form D.

The DVS isotherm for Form D is shown in FIG. 16. The material exhibits significant hygroscopicity, particularly above 55% RH, with a weight gain of 4.7 wt % noted between 5% and 95% RH. All of this weight was lost on desorption, with minor hysteresis observed. To be noted, the vapor sorption kinetic equilibration timed out on the sorption step between 85%-95% RH, indicating that the co-crystal could potentially pick up more moisture than what was measured if it was allowed a longer equilibration time.

Example 9

Preparation and Characterization of 4a/L-Proline Form G

Amorphous 4a, pyrazine, and L-proline were combined in 1:20:1 molar ratios, respectively, by first dissolving pyrazine in methyl ethyl ketone and MeOH (90:10, v/v). The pyrazine solution was added to the 4a and L-proline mixture and stirred at room temperature for two days to give an opaque white suspension. Form G was isolated by vacuum filtering the suspension.

Form G consists of an MEK solvated 4a/L-proline co-crystal. Form G exhibited a unique crystalline pattern by XRPD (FIG. 17) that was indexed (Table 11).

TABLE 11

Observed peaks for 4a/L-proline Form G

| °2θ | d space (Å) | Intensity (%) |
|---|---|---|
| 8.66 ± 0.20 | 10.200 ± 0.235 | 50 |
| 10.42 ± 0.20 | 8.480 ± 0.162 | 47 |
| 11.85 ± 0.20 | 7.461 ± 0.125 | 43 |
| 12.09 ± 0.20 | 7.316 ± 0.121 | 27 |
| 12.20 ± 0.20 | 7.247 ± 0.118 | 39 |
| 14.62 ± 0.20 | 6.056 ± 0.082 | 100 |
| 14.93 ± 0.20 | 5.927 ± 0.079 | 45 |
| 16.14 ± 0.20 | 5.485 ± 0.068 | 7 |
| 17.40 ± 0.20 | 5.092 ± 0.058 | 85 |
| 17.85 ± 0.20 | 4.965 ± 0.055 | 53 |
| 18.22 ± 0.20 | 4.865 ± 0.053 | 27 |
| 18.31 ± 0.20 | 4.842 ± 0.052 | 25 |
| 18.79 ± 0.20 | 4.719 ± 0.050 | 64 |
| 19.28 ± 0.20 | 4.600 ± 0.047 | 85 |
| 19.43 ± 0.20 | 4.565 ± 0.047 | 46 |
| 19.81 ± 0.20 | 4.479 ± 0.045 | 22 |
| 20.43 ± 0.20 | 4.344 ± 0.042 | 6 |
| 20.94 ± 0.20 | 4.239 ± 0.040 | 23 |
| 21.14 ± 0.20 | 4.198 ± 0.039 | 47 |
| 21.59 ± 0.20 | 4.113 ± 0.038 | 24 |
| 22.15 ± 0.20 | 4.010 ± 0.036 | 12 |
| 22.66 ± 0.20 | 3.921 ± 0.034 | 25 |
| 23.79 ± 0.20 | 3.738 ± 0.031 | 37 |
| 24.28 ± 0.20 | 3.663 ± 0.030 | 34 |
| 24.56 ± 0.20 | 3.622 ± 0.029 | 23 |
| 24.77 ± 0.20 | 3.592 ± 0.029 | 10 |
| 25.42 ± 0.20 | 3.501 ± 0.027 | 13 |
| 25.94 ± 0.20 | 3.432 ± 0.026 | 15 |
| 26.07 ± 0.20 | 3.415 ± 0.026 | 15 |
| 26.62 ± 0.20 | 3.345 ± 0.025 | 12 |
| 26.80 ± 0.20 | 3.323 ± 0.024 | 10 |
| 27.33 ± 0.20 | 3.261 ± 0.023 | 13 |
| 27.89 ± 0.20 | 3.197 ± 0.022 | 7 |
| 28.18 ± 0.20 | 3.165 ± 0.022 | 10 |
| 28.59 ± 0.20 | 3.120 ± 0.021 | 15 |
| 29.08 ± 0.20 | 3.068 ± 0.021 | 11 |
| 29.54 ± 0.20 | 3.022 ± 0.020 | 18 |

The unit cell volume (Table 12) obtained from indexing the XRPD pattern is consistent with a 1:1 4a/L-proline co-crystal with up to 1 mole MEK or pyrazine present (MEK and pyrazine molecules are comparable in volume and cannot be distinguished by XRPD indexing). The unit cell parameters (Table 12) also indicate that Form G is isostructural to Forms B and C. Form G was confirmed to contain 4a, L-proline, MEK, and minor residual pyrazine in a ~1:1.2:0.6:0.1 molar ratio by proton NMR.

TABLE 12

Unit Cell Parameters for 4a/L-proline Form G

| Bravais Type | Primitive Monoclinic |
|---|---|
| a [Å] | 10.975 |
| b [Å] | 10.310 |
| c [Å] | 15.704 |
| α [deg] | 90 |
| β [deg] | 108.56 |
| γ [deg] | 90 |
| Volume [Å³/cell] | 1,684.5 |
| Chiral Contents? | Chiral |
| Extinction Symbol | P 1 2$_1$ 1 |
| Space Group(s) | P2$_1$ (4) |

The single crystal analyses of Forms B and C indicated that those forms are isostructural, with 4a and L-proline forming a channel that houses additional L-proline for Form B and acetone for Form C. Both the L-proline and the acetone molecules in the respective channels do not form hydrogen bonds with the molecules comprising the channel. As mentioned above, the space group and other unit cell parameters obtained for Form G indicated that it is isostructural to Forms B and C. Although other explanations are possible, considering what is known about the molecular packing for those forms and the non-stoichiometric equivalents of L-proline and MEK measured by proton NMR for Form G, it is highly probable that the channel in Form G can accommodate both L-proline and MEK in a non-stoichiometric (and possibly variable) ratio due to the ease of exchange created by the lack of hydrogen bonding within the channel.

Example 10

Purification of 4a by Co-Crystal Formation

A. Purification with L-Proline

Co-crystallization of 4 according to procedures above led to Form B and Form D, and thereby very effectively reduced the amount of β-anomer 4b. A typical batch of amorphous 4 consisted of 4a/4b in 93.2%/6.3% as determined by HPLC. After the co-crystal formation step in a typical experiment, the level of 4b was reduced from 6.3% to 2.4% (HPLC). The resultant 4a/L-proline co-crystal was recrystallized by mixing it with MeOH (2 volumes), and the mixture was heated at reflux for 3 h. The mixture was cooled to 0±3° C. over 2.5 h, and then stirred overnight. The resulting solid was collected by filtration. After recrystallization, the amount of 4b was further reduced to 1.2%, and the purity of 4a was improved to 98.7% (HPLC).

B. Purification with D-Proline

A separate quantity of amorphous compound 4 contained 89.3% 4a and 10.1% 4b as determined by HPLC. Compound 4 (300 mg, 0.670 mmol) and D-proline (77.3 mg, 0.671 mmol) in EtOH (2.4 mL) were heated in a 90° C. oil bath. After refluxing for 15 min, the resulting solution was cooled to room temperature in a vial, and kept for 24 h with the vial cap removed to let EtOH evaporate slowly at room temperature. The precipitated solid was collected by filtration, and dried in air to give 4a/D-proline co-crystal. The co-crystal contained 97.6% 4a and 2.1% 4b as determined by HPLC (150 mg, 40% yield as a white solid). $^1$H NMR analysis of the co-crystal indicated a 1:1 molar ratio of 4a and D-proline.

Example 11

Preparation and Characterization of 4a/D-Proline Co-Crystal

A mixture of compound 4a (100 mg, 0.223 mmol) and D-proline (25.8 mg, 0.224 mmol) in EtOH (0.8 mL) was heated in a 90° C. oil bath. After refluxing for 15 min, the solution was cooled to room temperature, and kept in a capped vial at room temperature for 24 h. The vial cap was then removed to let EtOH evaporate slowly at room temperature. After 24 h, the precipitated solid was collected by filtration and then dried in air to give 4a/D-proline co-crystal as a white solid (74 mg, 59% yield) in 99+% purity (HPLC). $^1$H NMR analysis of indicated that the co-crystal contains 1/1 ratio of compound 4a and D-Proline.

Figure 18:
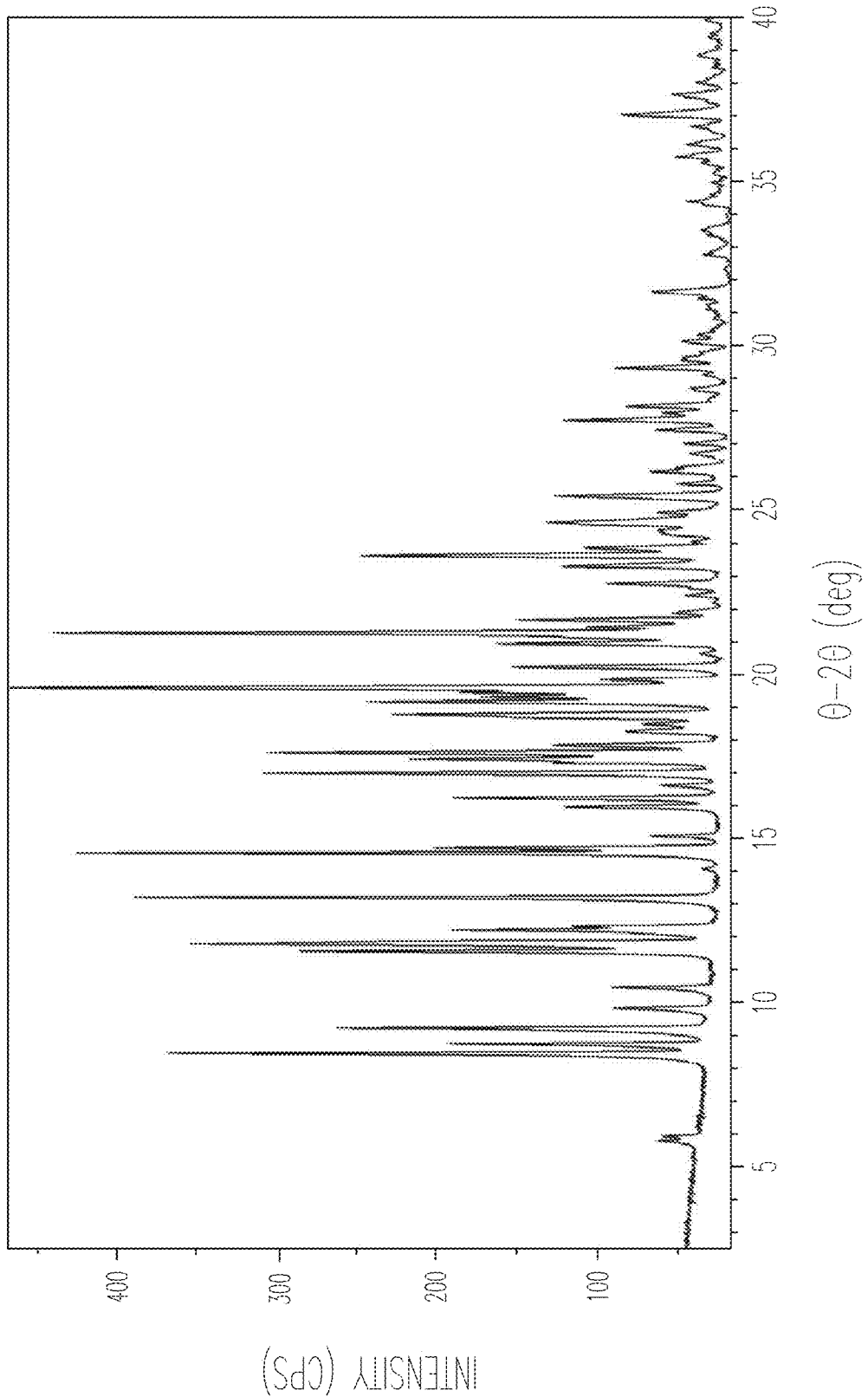
FIG. 18 presents an X-ray powder diffraction (XRPD) pattern of 4a/D-proline co-crystal.

The 4a/D-proline co-crystal was characterized by XRPD, DSC, TGA, and DVS. An XRPD pattern for the 4a/D-proline co-crystal was successfully indexed, indicating the material consists primarily or exclusively of a single crystalline phase (FIG. 18, Table 13).

TABLE 13

Observed peaks for 4a/D-proline

| °2θ | d space (Å) | Intensity (%) |
|---|---|---|
| 5.76 ± 0.20 | 15.323 ± 0.531 | 14 |
| 5.90 ± 0.20 | 14.964 ± 0.507 | 13 |
| 8.45 ± 0.20 | 10.453 ± 0.247 | 79 |
| 8.74 ± 0.20 | 10.113 ± 0.231 | 42 |
| 9.22 ± 0.20 | 9.579 ± 0.207 | 57 |
| 9.81 ± 0.20 | 9.007 ± 0.183 | 20 |
| 10.44 ± 0.20 | 8.470 ± 0.162 | 19 |
| 11.55 ± 0.20 | 7.653 ± 0.132 | 62 |
| 11.77 ± 0.20 | 7.511 ± 0.127 | 75 |
| 12.19 ± 0.20 | 7.256 ± 0.119 | 41 |
| 12.30 ± 0.20 | 7.189 ± 0.116 | 25 |
| 13.18 ± 0.20 | 6.713 ± 0.101 | 83 |
| 14.04 ± 0.20 | 6.303 ± 0.089 | 7 |
| 14.52 ± 0.20 | 6.094 ± 0.083 | 92 |
| 14.68 ± 0.20 | 6.028 ± 0.082 | 44 |
| 15.04 ± 0.20 | 5.886 ± 0.078 | 15 |
| 15.93 ± 0.20 | 5.559 ± 0.069 | 26 |
| 16.19 ± 0.20 | 5.470 ± 0.067 | 40 |
| 16.57 ± 0.20 | 5.345 ± 0.064 | 13 |
| 16.95 ± 0.20 | 5.226 ± 0.061 | 66 |
| 17.27 ± 0.20 | 5.131 ± 0.059 | 28 |
| 17.38 ± 0.20 | 5.099 ± 0.058 | 48 |
| 17.56 ± 0.20 | 5.045 ± 0.057 | 66 |
| 17.80 ± 0.20 | 4.980 ± 0.056 | 28 |
| 18.22 ± 0.20 | 4.865 ± 0.053 | 18 |
| 18.43 ± 0.20 | 4.810 ± 0.052 | 16 |
| 18.73 ± 0.20 | 4.735 ± 0.050 | 49 |
| 19.12 ± 0.20 | 4.639 ± 0.048 | 53 |
| 19.26 ± 0.20 | 4.604 ± 0.047 | 36 |
| 19.40 ± 0.20 | 4.573 ± 0.047 | 40 |
| 19.54 ± 0.20 | 4.539 ± 0.046 | 100 |
| 19.78 ± 0.20 | 4.485 ± 0.045 | 21 |
| 20.19 ± 0.20 | 4.394 ± 0.043 | 33 |
| 20.60 ± 0.20 | 4.308 ± 0.041 | 8 |
| 20.91 ± 0.20 | 4.245 ± 0.040 | 35 |
| 21.23 ± 0.20 | 4.183 ± 0.039 | 96 |
| 21.41 ± 0.20 | 4.146 ± 0.038 | 23 |
| 21.62 ± 0.20 | 4.107 ± 0.038 | 32 |
| 21.84 ± 0.20 | 4.066 ± 0.037 | 11 |
| 22.15 ± 0.20 | 4.009 ± 0.036 | 6 |
| 22.37 ± 0.20 | 3.972 ± 0.035 | 10 |
| 22.59 ± 0.20 | 3.934 ± 0.034 | 9 |
| 22.73 ± 0.20 | 3.910 ± 0.034 | 20 |
| 23.25 ± 0.20 | 3.823 ± 0.032 | 26 |
| 23.57 ± 0.20 | 3.771 ± 0.032 | 53 |
| 23.80 ± 0.20 | 3.736 ± 0.031 | 23 |
| 23.99 ± 0.20 | 3.706 ± 0.030 | 9 |
| 24.23 ± 0.20 | 3.670 ± 0.030 | 13 |

TABLE 13-continued

Observed peaks for 4a/D-proline

| °2θ | d space (Å) | Intensity (%) |
|---|---|---|
| 24.32 ± 0.20 | 3.657 ± 0.030 | 13 |
| 24.58 ± 0.20 | 3.619 ± 0.029 | 28 |
| 24.88 ± 0.20 | 3.575 ± 0.028 | 14 |
| 25.38 ± 0.20 | 3.506 ± 0.027 | 27 |
| 25.76 ± 0.20 | 3.456 ± 0.026 | 10 |
| 26.11 ± 0.20 | 3.410 ± 0.026 | 15 |
| 26.25 ± 0.20 | 3.392 ± 0.025 | 11 |
| 26.56 ± 0.20 | 3.354 ± 0.025 | 6 |
| 26.71 ± 0.20 | 3.335 ± 0.025 | 9 |
| 27.01 ± 0.20 | 3.299 ± 0.024 | 10 |
| 27.41 ± 0.20 | 3.251 ± 0.023 | 14 |
| 27.71 ± 0.20 | 3.216 ± 0.023 | 26 |
| 27.93 ± 0.20 | 3.192 ± 0.022 | 13 |
| 28.14 ± 0.20 | 3.168 ± 0.022 | 17 |
| 28.68 ± 0.20 | 3.110 ± 0.021 | 9 |
| 29.09 ± 0.20 | 3.067 ± 0.021 | 7 |
| 29.30 ± 0.20 | 3.045 ± 0.020 | 19 |

Figure 19:
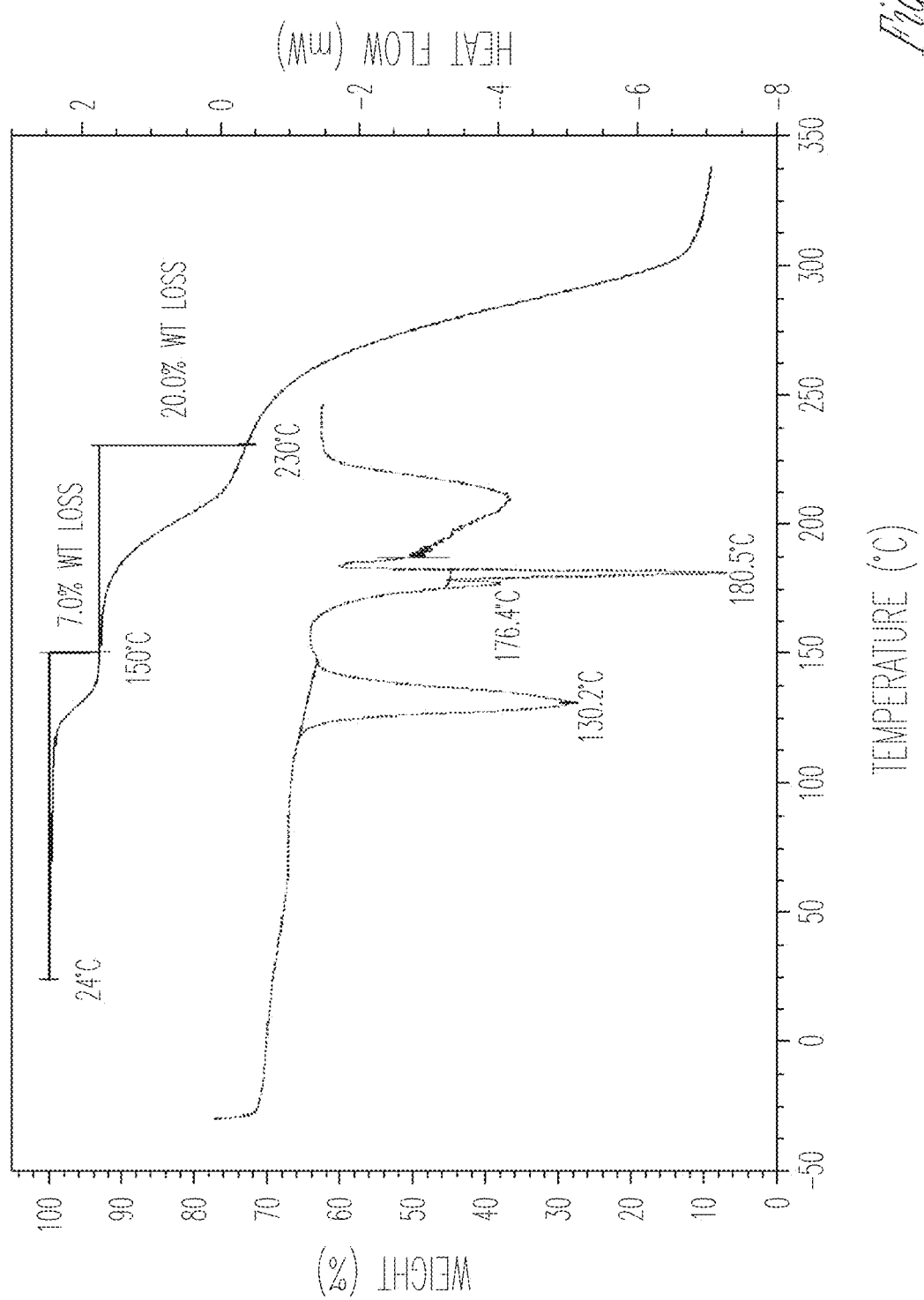
FIG. 19 shows DSC (bottom trace) and TGA (top trace) curves of 4a/D-proline co-crystal.

A DSC/TGA overlay for the material is shown in FIG. 19. The TGA thermogram for the 4a/D-proline co-crystal exhibited two distinct weight loss steps, the first occurring between ~100° C. and 150-160° C. (7.0% weight loss), and the second between 150 and 230° C. (20.0% weight loss). A broad endotherm was observed by DSC with a peak maximum at 130° C., which coordinates with the first TGA weight loss step, possibly attributed to the loss of bound solvent/water. Overlapping endothermic events were observed above ~170° C., likely due to concurrent melting/volatilization of the D-proline component of the co-crystal. A steep drop in the TGA thermogram above ~250° C. likely corresponds with decomposition.

Figure 20:
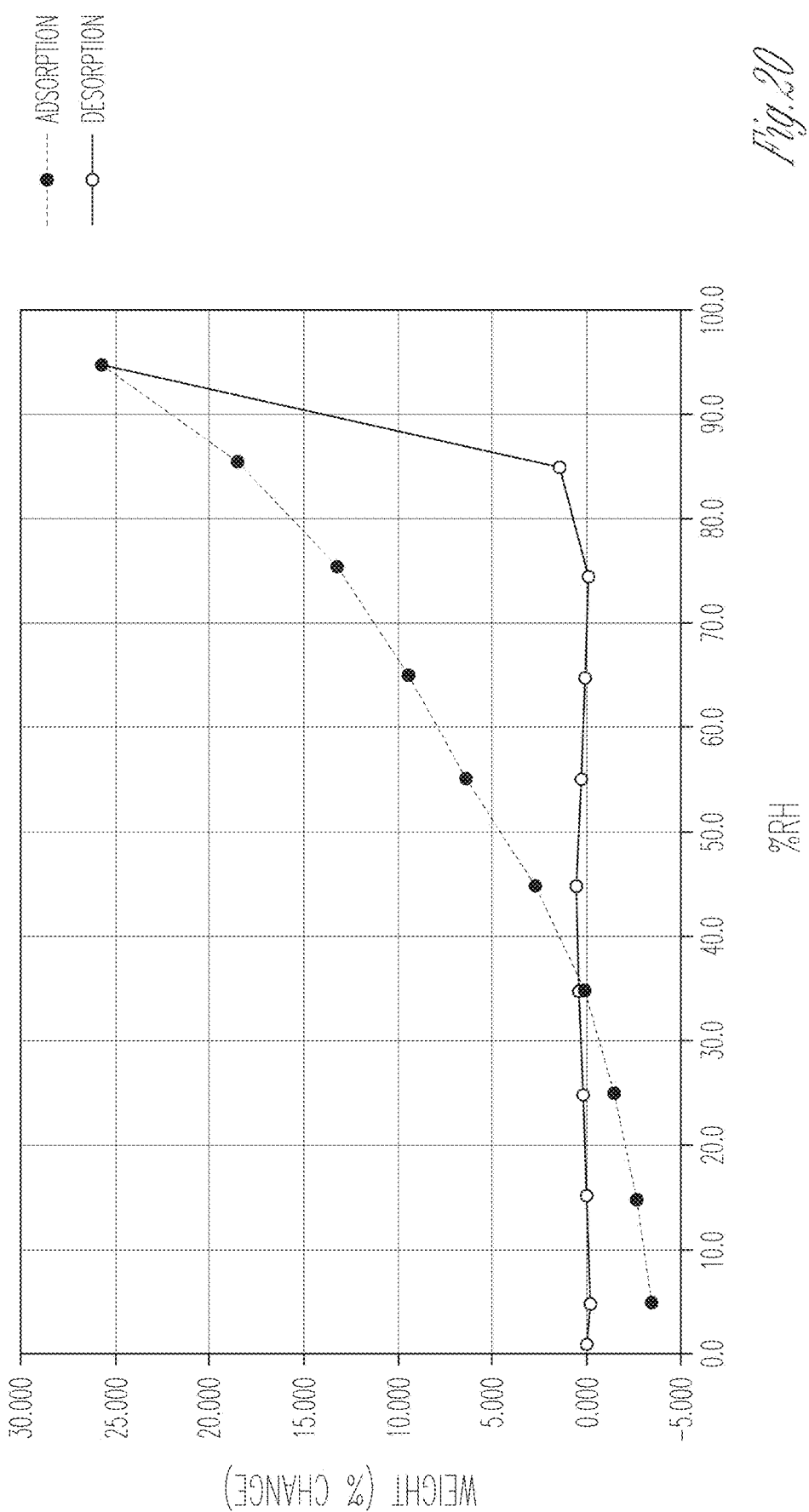
FIG. 20 is a dynamic vapor sorption (DVS) curve of 4a/D-proline co-crystal.

A DVS isotherm for the D-proline co-crystal is presented in FIG. 20. Upon sorption, the co-crystal gained 26 wt % between 5% and 95% RH, with the vast majority of weight gain occurring between 85% and 95% RH. The kinetic equilibration timed out during this step, indicating that the co-crystal could potentially pick up more moisture than what was measured if it was allowed a longer equilibration time. Upon desorption, the co-crystal exhibited relatively steady weight loss between 95% and 5% RH and lost more weight than was gained during sorption (29 wt %), indicating that the material likely contained solvent/water at the start of the analysis. To be noted, the post-DVS sample of the D-proline co-crystal was observed to be stuck to the pan and could not be recovered, indicating partial deliquescence during the experiment.

Example 12

Comparative Administration of 4a/L-Proline Material A and Amorphous 4a to Mice

This example evaluated the systemic exposure to 4a after oral administration of a suspension formulation of Material A as prepared in Example 1 compared to a suspension formulation of amorphous 4a in male C57BL/6 mice.

Amorphous 4a or Material A was formulated in 0.5% CMC with 5% DMSO (taking into account the presence of proline on a weight basis) and administered by oral gavage to 35 male C57BL/6 mice at 1000 mg/kg using a dosing volume of 15 mL/kg. Blood samples for plasma isolation were collected at 0.25, 0.5, 1, 2, 4, 8, and 24 hours post-dose, using a separate group (n=5/group/time point) of mice for each time point, as summarized in Table 14 below. Plasma samples were analyzed for concentrations of 4a by LC/MS/MS methodology as described below.

TABLE 14

Summary of Mouse Study

| Group | Test Article | N | Dose Route | Vehicle | Dose Level (mg/kg) | Dose Volume (mL/kg) | Blood Collection Times (hr) |
|---|---|---|---|---|---|---|---|
| 1 | Amorphous 4a | 35 | PO | 0.5% CMC/ 5% DMSO in sterile water | 1000 | 15 | 0.25, 0.5, 1, 2, 4, 8, & 24 |
| 2 | Material A | 35 | PO | 0.5% CMC/ 5% DMSO in sterile water | 1000 | 15 | 0.25, 0.5, 1, 2, 4, 8, & 24 |

Reagents and Supplies: All reagents and supplies were of high quality and of LC/MS grade when appropriate and obtained from standard commercial suppliers.

Plasma Sample Preparation: 4a was extracted from $K_3$EDTA-fortified plasma samples using a protein precipitation method. In a well of a polypropylene microplate (96-well), 20 µL of a 2.5-ng/mL $D_3$-4a (internal standard, IS) solution prepared in acetonitrile/$H_2O$ (1:1) was added, followed by addition of 20 µL of plasma sample. The plate was sealed with sealing tape (Phenomenex, AH0-7362) and gently mixed with a vortex-mixer for 1 minute. The solution was pipetted into a well of a polypropylene plate (96-well, 2 mL, Phenomenex, AH0-7194) that contained 500 µL of methanol. The plate was sealed and vortex-mixed for 5 minutes followed by centrifugation at 3000×g for 3 minutes at room temperature. A 300-µL aliquot of the supernatant was transferred to a new well that contained 300 µL of deionized water. After gentle mixing, the plate was sealed and placed in an LC autosampler maintained at 12° C., and a 10-µL aliquot was injected into an LC/MS/MS system for quantitative analysis of 4a.

Chromatography and Mass Spectrometry Conditions: Liquid chromatographic separation of 4a was achieved by a reversed-phase analytical column with mobile phase solution containing $H_2O$, acetonitrile, and formic acid. The chromatographed analyte was detected by a Waters Xevo TQ-S triple quadrupole mass spectrometer operating in multiple-reaction-monitoring (MRM) mode. Chromatographed peak areas for quality control samples, calibration standards, and study samples were integrated using MassLynx software V4.1 (Waters Corp.).

Pharmacokinetic Analysis: Pharmacokinetic parameter estimates were obtained from non-compartmental analysis of the mean 4a plasma concentration-time data for each dose group using WinNonlin™ software version 6.3 (Pharsight Corp., Cary, N.C.). The area under the plasma concentration-time curve from time zero to the time (t) of the last measurable concentration of 4a ($AUC_{(0-t)}$) was determined using the linear log trapezoidal rule. The time of the last measurable concentration was defined as the time after which 4a concentrations were below the limit of quantitation (BLQ) in the majority of animals for each dose group.

Figure 21:
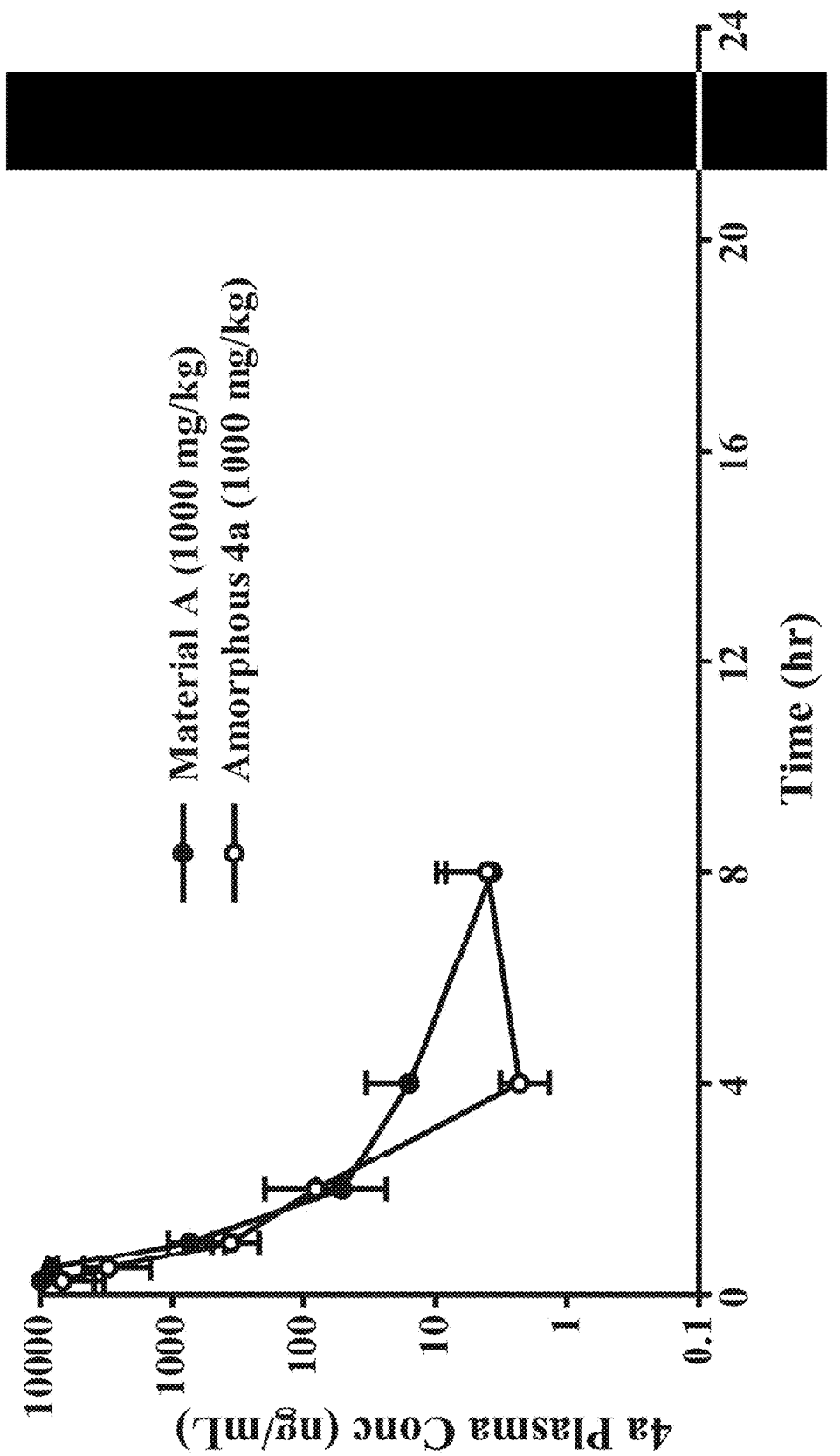
FIG. 21 shows mean plasma concentrations of 4a in mice following administration of a single oral dose of Material A (●) and amorphous 4a (○).

Results: Mean (±SD) 4a plasma concentration-time data after a single oral gavage administration of Material A and amorphous 4a are presented in Table 15 below and displayed in FIG. 21. Pharmacokinetic parameter estimates for 4a are presented in Table 16.

TABLE 15

Mean (±SD) Plasma Concentrations of 4a in Mice Following Administration of a Single Oral Dose of Material A and Amorphous 4a

| Time (hr) | 4a Plasma Concentration (ng/mL) | |
| --- | --- | --- |
|  | Material A | Amorphous 4a |
| 0.25 | 9770 ± 6480 | 6760 ± 2840 |
| 0.5 | 8090 ± 690 | 3060 ± 1600 |
| 1 | 733 ± 336 | 359 ± 140 |
| 2 | 51.4 ± 27.7 | 80.7 ± 116 |
| 4 | 15.8 ± 17.9 | 2.28 ± 0.92 |
| 8 | 3.68 ± 6.12 | 4.01 ± 4.34 |
| 24 | BLQ[a] | BLQ[a] |

[a]All samples in group were BLQ.

TABLE 16

Plasma Pharmacokinetic Parameter Estimates after a Single Oral Administration to Mice

| Group | Dose (mg/kg) | $T_{max}$ (hr) | $C_{max}$ (ng/mL) | $AUC_{(0-t)}$ (hr*ng/mL) |
| --- | --- | --- | --- | --- |
| Material A | 1000 | 0.25 | 9770 | 5330 |
| Amorphous 4a | 1000 | 0.25 | 6760 | 2880 |

Example 13

Comparative Administration of 4a/L-Proline Material A and Amorphous 4a to Monkeys This example evaluated the systemic exposure of Material A as prepared in Example 1 and amorphous 4a formulations, respectively, in male cynomolgus monkeys after a single oral gavage administration at 30 mg/kg using 0.5% carboxymethylcellulose (CMC) in sterile water as vehicle (5 mL/kg) or at 50 mg (regardless of body weight) in a loose-filled capsule as summarized in Table 17 below.

TABLE 17

Summary of Monkey Study

| Group | Test Article | N | Dose Route | Vehicle | Dose Level | Dose Volume (mL/kg) | Blood Collection Times (hr) |
| --- | --- | --- | --- | --- | --- | --- | --- |
| 1 | Material A | 3 | PO | 0.5% CMC in sterile water | 30 mg/kg | 5 | 0.25, 0.5, 1, 2, 4, 8, 12, and 24 |
| 2 | Amorphous 4a | 3 | PO | 0.5% CMC in sterile water | 30 mg/kg | 5 | 0.25, 0.5, 1, 2, 4, 8, 12, and 24 |
| 3 | Material A | 3 | PO | Gelatin Capsule (size 00) | 50 mg[a] | NA[b] | 0.25, 0.5, 1, 2, 4, 8, 12, and 24 |
| 4 | Amorphous 4a | 3 | PO | Gelatin Capsule (size 00) | 50 mg[a] | NA[b] | 0.25, 0.5, 1, 2, 4, 8, 12, and 24 |

[a]Dose administered regardless of body weight
[b]NA, Not applicable

Dosing of Material A accounted for the presence of proline on a weight basis. Blood samples for plasma isolation were collected at 0.25, 0.5, 1, 2, 4, 8, 12, and 24 hours post-dose from each monkey. Plasma samples were analyzed for concentrations of 4a by LC/MS/MS methodology, and pharmacokinetic analysis was carried out, as described in Example 12 above.

Figure 22:
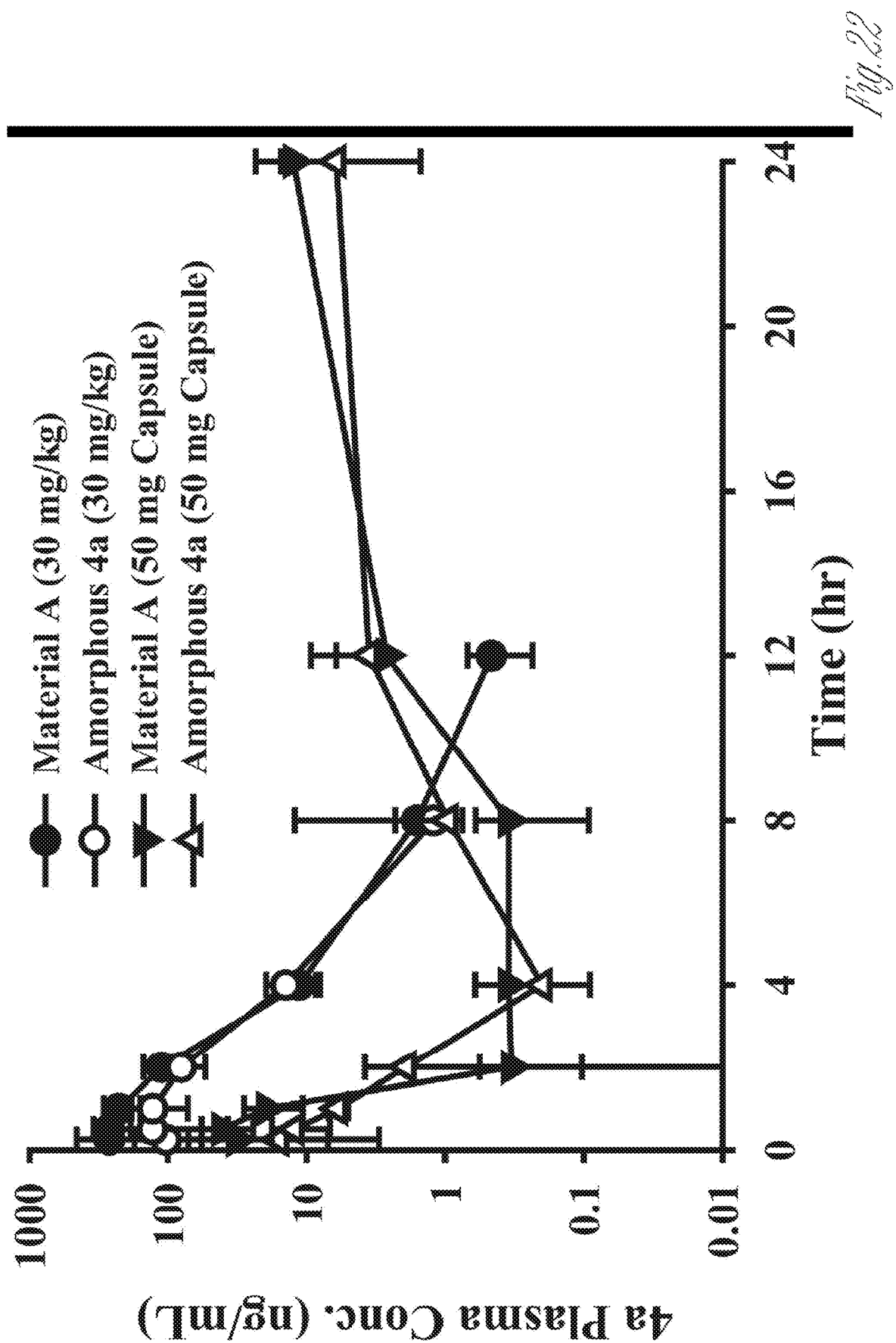
FIG. 22 shows mean plasma concentrations of 4a in monkeys following administration of a single oral dose of Material A (●) and amorphous 4a (○) by oral gavage, and of Material A (▼) and amorphous 4a (Δ) in loose-filled capsules.

Results: Mean (±SD) plasma concentrations after a single oral gavage (30 mg/kg, 5 mL/kg) or after capsule dosing (50 mg) are presented in Table 18 below and displayed in FIG. 22. Pharmacokinetic parameter estimates are presented in Table 19.

TABLE 18

Mean (±SD) 4a Plasma Concentrations in Monkeys Following Oral Administration of Material A or Amorphous 4a as a Suspension or Capsule 4a Plasma Concentration (ng/mL)

| Time (hr) | Oral Gavage (30 mg/kg) | | Capsule (50 mg) | |
| --- | --- | --- | --- | --- |
|  | Material A | Amorphous 4a | Material A | Amorphous 4a |
| 0.25 | 264 ± 193 | 103 ± 71 | 32.1 ± 25.1 | 15.9 ± 12.9 |
| 0.5 | 265 ± 79 | 129 ± 92 | 40.8 ± 16.4 | 12.3 ± 5.5 |
| 1 | 225 ± 67 | 128 ± 56 | 19.6 ± 8.9 | 5.97 ± 0.95 |
| 2 | 111 ± 39 | 80.2 ± 26.4 | 0.333 ± 0.230[a] | 1.90 ± 1.89 |
| 4 | 11.3 ± 3.3 | 14.1 ± 5.5 | 0.349 ± 0.259[a] | 0.200[b] |
| 8 | 1.60 ± 0.70 | 1.20 ± 0.45 | 0.348 ± 0.256[a] | 0.951 ± 1.30[a] |
| 12 | 0.463 ± 0.228[c] | BLQ[d] | 2.64 ± 3.48[c] | 3.53 ± 5.78[a] |
| 24 | BLQ[e] | BLQ[d] | 12.5 ± 11.0[c] | 6.11 ± 9.23[c] |

[a]2 of 3 values for intermediate time point (i.e., between 2 time points with quantifiable values) were below the limit of quantitation (BLQ) and included in the mean as ½ the lower limit of quantitation (LLOQ) (i.e., 0.200 ng/mL)
[b]All values for intermediate time point (i.e., between 2 time points with quantifiable values) were BLQ and reported as ½ the LLOQ (i.e., 0.200 ng/mL)
[c]1 of 3 values was BLQ and assigned a value of ½ the LLOQ (i.e., 0.200 ng/mL) to calculate mean and standard deviation
[d]Mean reported as BLQ because 2 of 3 samples were BLQ
[e]All values were BLQ

TABLE 19

Mean (±SD) Pharmacokinetic Data in Monkeys Following Administration of 4a by Oral Gavage of a Suspension or Capsule

| Group | $T_{max}$ (hr)[a] | $C_{max}$ (ng/mL) | $AUC_{(0-t)}$ (hr*ng/mL) |
|---|---|---|---|
| Material A (30 mg/kg) | 0.25 | 309 ± 117 | 491 ± 120 |
| Amorphous 4a (30 mg/kg) | 0.5 | 160 ± 78 | 307 ± 96 |
| Material A (50 mg capsule) | 0.25 | 51.0 ± 7.6 | 110 ± 85 |
| Amorphous 4a (50 mg capsule) | 0.25 | 19.7 ± 9.4 | 81.6 ± 105 |

[a]Data presented as median

Both capsule formulations (but not the oral suspension formulations) produced 4a plasma concentrations that were below or near the lower limit of quantitation (i.e., 0.400 ng/mL) at 4 and 8 hours post-dose but demonstrated a secondary peak of exposure at 24 hours with mean (±SD) 4a concentrations of 12.5±11.0 and 6.11±9.23 ng/mL for the Material A and amorphous 4a formulations, respectively.

We claim:

1. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline (1:2), characterized by an X-ray powder diffractogram comprising the following peaks: 14.76, 16.86, 19.00, and 21.05 °2θ±0.20 °2θ as determined on a diffractometer using Cu-Kα radiation at a wavelength of 1.54178 Å.

2. The co-crystal according to claim 1, wherein the X-ray powder diffractogram further comprises peaks at 12.14, 17.51, 18.89, and 19.41 °2θ±0.20 °2θ.

3. The co-crystal according to claim 1, wherein the X-ray powder diffractogram is substantially as shown in FIG. 1.

4. The co-crystal according to claim 1, characterized by a differential scanning calorimetry (DSC) thermogram comprising an exotherm at about 211° C.

5. The co-crystal according to claim 4, wherein the DSC thermogram is substantially as shown in FIG. 2.

6. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline (1:2), characterized by an X-ray powder diffractogram comprising the following peaks: 9.20, 16.19, 18.45, and 24.51 °2θ±0.20 °2θ as determined on a diffractometer using Cu-Kα radiation at a wavelength of 1.54178 Å.

7. The co-crystal according to claim 6, wherein the X-ray powder diffractogram further comprises peaks at 11.83, 17.16, 20.15, and 25.34 °2θ±0.2 °2θ.

8. The co-crystal according to claim 6, wherein the X-ray powder diffractogram is substantially as shown in FIG. 14.

9. The co-crystal according to claim 6, characterized by a differential scanning calorimetry (DSC) thermogram comprising an endotherm having an onset temperature of about 211.2° C.

10. The co-crystal according to claim 9, wherein the DSC thermogram is substantially as shown in FIG. 15.

11. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline acetone solvate (1:1:1), characterized by an X-ray powder diffractogram comprising the following peaks: 14.64, 17.53, 18.91, and 21.33 °2θ±0.20 °2θ as determined on a diffractometer using Cu-Kα radiation at a wavelength of 1.54178 Å.

12. The co-crystal according to claim 11, wherein the X-ray powder diffractogram further comprises peaks at 12.10, 15.14, 18.26, and 19.56 °2θ±0.2 °2θ.

13. The co-crystal according to claim 11, wherein the X-ray powder diffractogram is substantially as shown in FIG. 10.

14. The co-crystal according to claim 11, characterized by a thermogravimetric analysis (TGA) thermogram comprising weight loss steps that conclude at about 150° C. and about 220° C.

15. The co-crystal according to claim 14, wherein the TGA thermogram is substantially as shown in FIG. 11.

16. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide, L-proline, methyl ethyl ketone, and pyrazine in a molar ratio of about 1:12:0.6:0.1, characterized by an X-ray powder diffractogram comprising the following peaks: 10.42, 14.62, 19.28, and 21.14 °2θ±0.20 °2θ as determined on a diffractometer using Cu-Kα radiation at a wavelength of 1.54178 Å.

17. The co-crystal according to claim 16, wherein the X-ray powder diffractogram further comprises peaks at 11.85, 14.93, 17.40, and 19.28 °2θ±0.2 °2θ.

Figure 17:
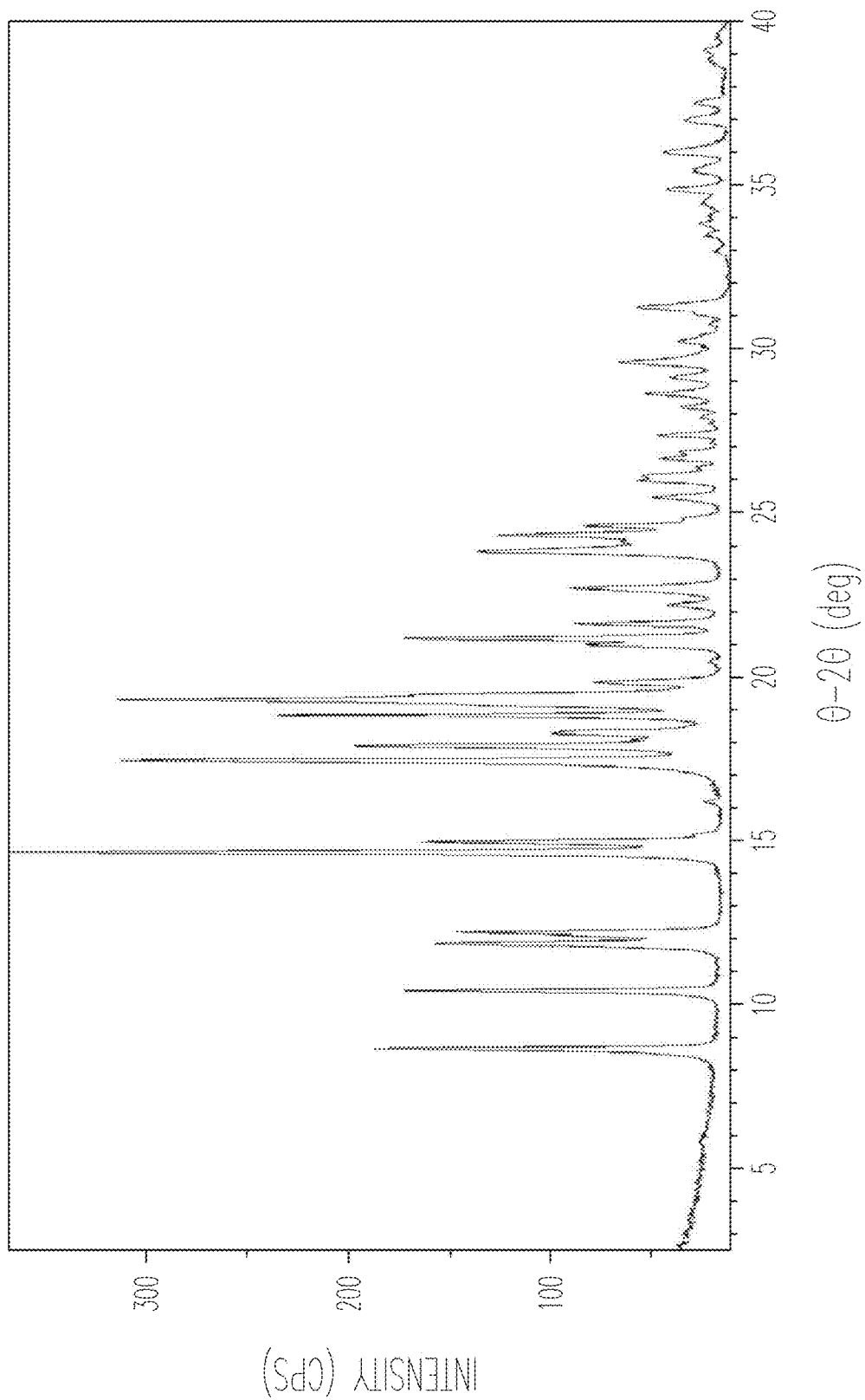
FIG. 17 presents an X-ray powder diffraction (XRPD) pattern of Form G.

18. The co-crystal according to claim 16, wherein the X-ray powder diffractogram is substantially as shown in FIG. 17.

19. The co-crystal according to claim 16, characterized by unit cell dimensions as follows: a=10.975 Å, b=10.310 Å, c=15.704 Å, α=90°, β=108.56°, and γ=90°.

20. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and D-proline (1:1), characterized by an X-ray powder diffractogram comprising the following peaks: 11.77, 14.52, 19.54, and 21.23 °2θ±0.20 °2θ as determined on a diffractometer using Cu-K$_{α1}$ radiation at a wavelength of 1.5405929 Å.

21. The co-crystal according to claim 20, wherein the X-ray powder diffractogram further comprises peaks at 8.45, 13.18, 16.95, and 19.12 °2θ±0.2 °2θ.

22. The co-crystal according to claim 20, wherein the X-ray powder diffractogram is substantially as shown in FIG. 18.

23. The co-crystal according to claim 20, characterized by a differential scanning calorimetry (DSC) thermogram comprising an endotherm at about 130° C.

24. The co-crystal according to claim 23, wherein the DSC thermogram is substantially as shown in FIG. 19.

25. A co-crystal of N-(2-(5-(((2R,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide and L-proline (1:1), characterized by an X-ray powder diffractogram comprising the following peaks: 8.52, 16.33, 19.50, and 21.22 °2θ±0.20 °2θ as determined on a diffractometer using Cu-K$_{α1}$ radiation at a wavelength of 1.5405929 Å.

26. The co-crystal according to claim 25, wherein the X-ray powder diffractogram further comprises peaks at 9.19, 13.22, 14.75, and 17.57 °2θ±0.2 °2θ.

Figure 23:
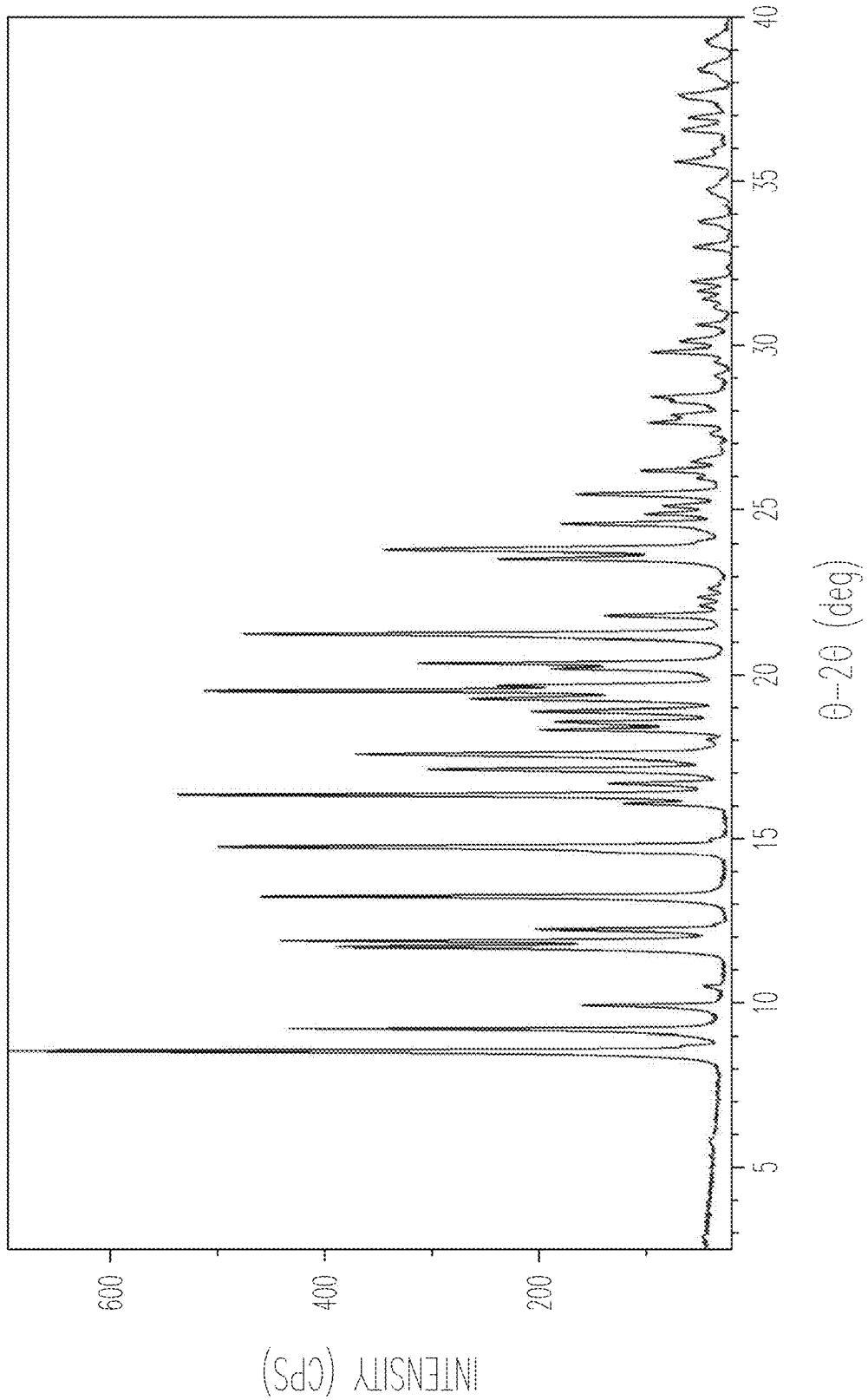
FIG. 23 presents an X-ray powder diffraction (XRPD) pattern of 4a/L-proline co-crystal Material A.

27. The co-crystal according to claim 25, wherein the X-ray powder diffractogram is substantially as shown in FIG. 23.

28. The co-crystal according to claim 25, characterized by unit cell dimensions as follows: a=10.126 Å, b=11.021 Å, c=30.259 Å, α=90°, β=90°, and γ=90°.

29. The co-crystal according to claim 25, characterized by a differential scanning calorimetry (DSC) thermogram comprising an endotherm at about 145° C.

30. The co-crystal according to claim 29, wherein the DSC thermogram is substantially as shown in FIG. 24.

31. A pharmaceutical composition comprising a co-crystal according to any one of claims 1, 6, 11, 16, 20, and 25 and a pharmaceutically acceptable solid carrier.

32. A method for inhibiting heat shock protein 90 (Hsp90) in a subject, comprising administering to the subject a therapeutically effective amount of a co-crystal according to any one of claims 1, 6, 11, 16, 20, and 25.

33. A method for treating or preventing a neurodegenerative disorder in a subject suffering therefrom, comprising administering to the subject a therapeutically effective amount of a co-crystal according to any one of claims 1, 6, 11, 16, 20, and 25.

34. The method according to claim 33, wherein the neurodegenerative disorder is diabetic peripheral neuropathy.

35. A method for preventing or reducing the likelihood of diabetic peripheral neuropathy from developing in a subject, comprising administering to the subject a therapeutically effective amount of a co-crystal according to any one of claims 1, 6, 11, 16, 20, and 25, wherein the subject suffers from Type 1 or Type 2 diabetes.

36. A method of increasing the concentration of N-(2-(5-(((2R,3R,4S,5R)-3,4-dihydroxy-5-methoxy-6,6-dimethyl-tetra-hydro-2H-pyran-2-yl)oxy)-3'-fluoro-[1,1'-biphenyl]-2-yl)ethyl)-acetamide (4a) relative to N-(2-(5-(((2S,3R,4S,5R)-3,4-dihydroxy-5-methoxy-6,6-dimethyltetra-hydro-2H-pyran-2-yl)oxy)-3'-fluoro-[1,1'-biphenyl]-2-yl)ethyl)-acetamide (4b) in a starting composition comprising 4a and 4b, comprising contacting the starting composition with proline in a solvent, and subjecting the starting composition, proline, and solvent to crystallization conditions, whereby a co-crystal of 4a and proline is produced, wherein the bulk co-crystal exhibits a concentration of 4a that is higher than in the starting composition comprising 4a and 4b.

37. The method according to claim 36, wherein the proline is L-proline.

38. The method according to claim 36, wherein the proline is D-proline.

39. The method according to claim 36, wherein the method further comprises heating the starting composition, proline, and solvent.

40. The method according to claim 36, wherein the concentration of 4a is determined by HPLC.

41. The method according to claim 36, wherein the concentration of 4a in the bulk co-crystal of 4a and proline is about 3 to about 20% (w/w) higher than in the starting composition.

42. The method according to claim 36, wherein the concentration of 4a in the bulk co-crystal of 4a and proline is about 5 to about 15% (w/w) higher than in the starting composition.

43. The method according to claim 36, wherein the concentration of 4a in the bulk co-crystal of 4a and proline increases by about 5%, about 10%, or about 15% (w/w).

* * * * *